United States Patent
Kai et al.

(10) Patent No.: US 9,260,433 B2
(45) Date of Patent: Feb. 16, 2016

(54) ORGANIC ELECTROLUMINESCENT DEVICE

(75) Inventors: Takahiro Kai, Kitakyushu (JP); Toshihiro Yamamoto, Kitakyushu (JP); Masaki Komori, Kitakyushu (JP); Megumi Matsumoto, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 906 days.

(21) Appl. No.: 13/512,883

(22) PCT Filed: Nov. 18, 2010

(86) PCT No.: PCT/JP2010/070536
§ 371 (c)(1),
(2), (4) Date: May 30, 2012

(87) PCT Pub. No.: WO2011/080972
PCT Pub. Date: Jul. 7, 2011

(65) Prior Publication Data
US 2012/0235133 A1    Sep. 20, 2012

(30) Foreign Application Priority Data
Dec. 28, 2009 (JP) .................. 2009-297903

(51) Int. Cl.
| | | |
|---|---|---|
| H01L 51/50 | (2006.01) | |
| C07D 487/04 | (2006.01) | |
| C09K 11/06 | (2006.01) | |
| H01L 51/00 | (2006.01) | |
| H05B 33/14 | (2006.01) | |

(52) U.S. Cl.
CPC .............. *C07D 487/04* (2013.01); *C09K 11/06* (2013.01); *H01L 51/0072* (2013.01); *H05B 33/14* (2013.01); *C09K 2211/1007* (2013.01); *C09K 2211/1029* (2013.01); *C09K 2211/1044* (2013.01); *C09K 2211/1074* (2013.01); *C09K 2211/1088* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 2009/0302742 A1 | 12/2009 | Komori et al. | |
| 2010/0148161 A1* | 6/2010 | Kai et al. | ......... 257/40 |
| 2010/0148162 A1 | 6/2010 | Komori et al. | |

FOREIGN PATENT DOCUMENTS

| | | |
|---|---|---|
| WO | WO-2007/063754 A1 | 6/2007 |
| WO | WO-2008/146839 A1 | 12/2008 |
| WO | WO-2008/149691 A1 | 12/2008 |
| WO | WO-2009/136596 A1 | 11/2009 |

OTHER PUBLICATIONS

International Search Report for the Application No. PCT/JP2010/070536 mailed Jan. 25, 2011.

* cited by examiner

*Primary Examiner* — Gregory Clark
(74) *Attorney, Agent, or Firm* — Cheng Law Group, PLLC

(57) ABSTRACT

Disclosed is an organic electroluminescent device (organic EL device) which is improved in luminous efficiency, sufficiently secures driving stability, and has a simple configuration. The organic EL device of this invention comprises a light-emitting layer between an anode and a cathode piled one upon another on a substrate and the light-emitting layer contains a phosphorescent dopant and an unsymmetrical indolocarbazole compound as a host material. The unsymmetrical indolocarbazole compound has a structure in which two or more groups having an indolocarbazole structure are linked together by a linking group and at least one of the groups has an isomeric indolocarbazole skeleton different from those of the other groups. Examples of the unsymmetrical indolocarbazole compound include compounds represented by the following formula (2) wherein A is a substituent, each of $R_1$ to $R_3$ is a hydrogen atom or a substituent, and L is a linking group composed of an aromatic group.

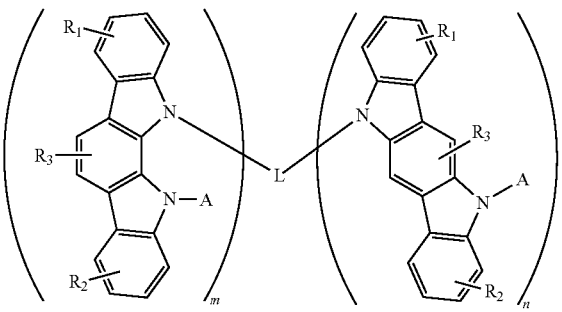

(2)

6 Claims, 1 Drawing Sheet

ORGANIC ELECTROLUMINESCENT DEVICE

TECHNICAL FIELD

This invention relates to an organic electroluminescent device containing an indolocarbazole compound and, more particularly, to a thin film type device which emits light upon application of an electric field to a light-emitting layer composed of an organic compound.

BACKGROUND TECHNOLOGY

An organic electroluminescent device (hereinafter referred to as organic EL device) in the simplest structure is generally constituted of a light-emitting layer and a pair of counter electrodes holding the light-emitting layer between them. The organic EL device functions by utilizing the following phenomenon; upon application of an electric field between the electrodes, electrons are injected from the cathode and holes are injected from the anode and they recombine in the light-emitting layer with emission of light.

In recent years, organic thin films have been utilized in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (Alq3) are disposed in thin film between the electrodes. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

Further, in an effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others have utilized fluorescence. The use of phosphorescence, that is, emission of light from the triplet excited state, is expected to enhance the luminous efficiency three to four times that of the conventional devices using fluorescence (emission of light from the singlet excited state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as stated in patent document 1, a large number of researches are conducted on phosphorescent dopant materials with the objective of enhancing the luminous efficiency and extending the life while giving priority to utilization of organic metal complexes such as iridium complexes.

PRIOR ART TECHNICAL DOCUMENTS

Patent Documents

Patent document 1: JP 2003-515897 A
Patent document 2: JP 2001-313178 A
Patent document 3: JP Hei 11-162650 A
Patent document 4: JP Hei 11-176578 A
Patent document 5: WO 2007-063754

In order to obtain high luminous efficiency, a host material to be used together with the aforementioned dopant material becomes important. Of the host materials proposed thus far, a typical example is 4,4'-bis(9-carbazolyl)biphenyl (hereinafter referred to as CBP), a carbazole compound presented in patent document 2. Since CBP is characterized by having a good hole transfer property but a poor electron transfer property, the use of CBP as a host material for tris(2-phenylpyridine)iridium complex (hereinafter referred to as Ir(ppy)$_3$), a typical phosphorescent green light emitter, disturbs the balanced injection of charges and causes excessive holes to flow out to the side of the electron-transporting layer. The result is a reduction in the luminous efficiency of Ir(ppy)$_3$.

As described above, in order for an organic EL device to perform at high luminous efficiency, the device needs a host material which has high excited triplet energy and is well balanced in injection/transport characteristics of electric charges (holes and electrons). Meanwhile, compounds which are electrochemically stable, highly resistant to heat, and excellently stable in the amorphous state are desired and further improvements are demanded.

Patent document 3 discloses the indolocarbazole compound illustrated below as a hole-transporting material.

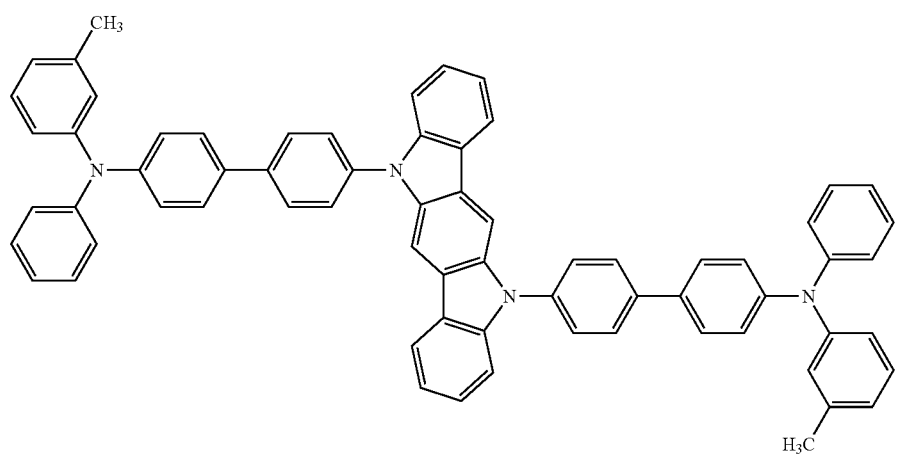 [SMILES: Cc1cccc(N(c2ccccc2)c2ccc(-c3ccc(-n4c5ccccc5c5cc6c(cc54)c4ccccc4n6-c4ccc(-c5ccc(N(c6ccccc6)c6cccc(C)c6)cc5)cc4)cc3)cc2)c1]

Patent document 4 discloses the indolocarbazole compound illustrated below as a hole-transporting material.

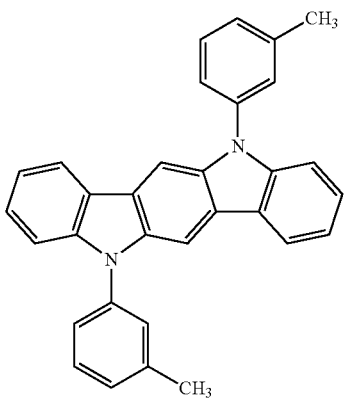 [SMILES: Cc1cccc(-n2c3ccccc3c3cc4c(cc32)c2ccccc2n4-c2cccc(C)c2)c1]

These patent documents recommend the use of the compounds having an indolocarbazole skeleton as hole-transporting materials. However, such use is demonstrated only in fluorescent light-emitting devices in the examples of the documents and it cannot be said that the use as materials for phosphorescent light-emitting devices is disclosed.

Patent document 5 discloses the indolocarbazole compound illustrated below as a host material and further discloses that the use of this compound in an organic EL device improves the luminous efficiency and provides high driving stability.

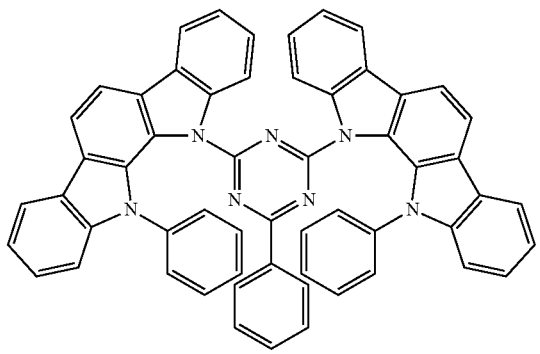 [SMILES: c1ccc(-c2nc(-n3c4ccccc4c4ccc5c6ccccc6n(-c6ccccc6)c5c43)nc(-n3c4ccccc4c4ccc5c6ccccc6n(-c6ccccc6)c5c43)n2)cc1]

SUMMARY OF THE INVENTION

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device which exhibits such high luminous efficiency and driving stability as to be practically useful and to provide a compound suitable therefor.

The inventors of this invention have conducted intensive studies, found that the use of a compound having an indolocarbazole skeleton of a specified structure enables an organic EL device to display excellent characteristics, and completed this invention.

This invention relates to an organic electroluminescent device comprising an anode, organic layers comprising a phosphorescent light-emitting layer, and a cathode piled one upon another on a substrate wherein at least one organic layer selected from the group consisting of a phosphorescent light-emitting layer, a hole-transporting layer, an electron-transporting layer, and a hole-blocking layer contains an indolocarbazole compound represented by general formula (1).

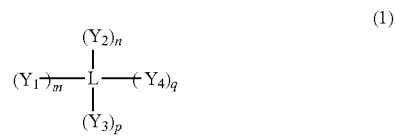

(1)

In general formula (1), L is an (m+n+p+q)-valent aromatic hydrocarbon group of 6 to 50 carbon atoms or an (m+n+p+q)-valent aromatic heterocyclic group of 3 to 50 carbon atoms; each of $Y_1$ to $Y_4$ is represented by any one of formulas (1a-1) to (1a-6) and at least one group is different from others; m is an integer of 1 to 3, n is an integer of 1 to 3, p is an integer of 0 to 3, q is an integer of 0 to 3, and m+n+p+q is an integer of 2 to 6.

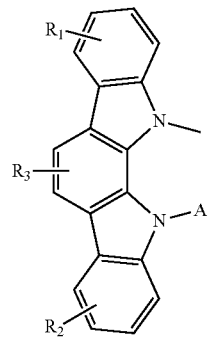

(1a-1)

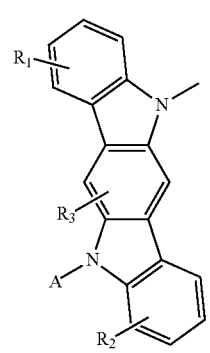

(1a-2)

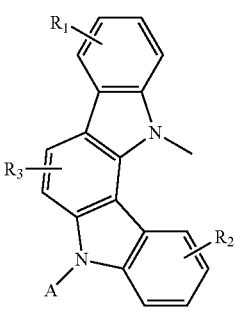

(1a-3)

(1a-4)

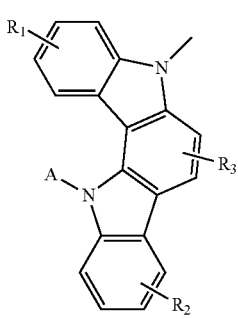

(1a-5)

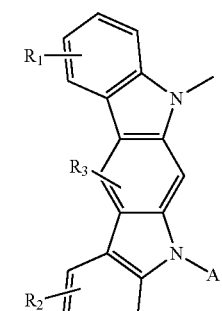

(1a-6)

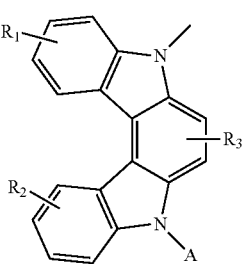

In formulas (1a-1) to (1a-6), each A is independently an alkyl group of 1 to 10 carbon atoms, a cycloalkyl group of 3 to 11 carbon atoms, an aromatic hydrocarbon group of 6 to 50 carbon atoms, or an aromatic heterocyclic group of 3 to 50 carbon atoms; each of $R_1$ to $R_3$ is independently a hydrogen atom, an alkyl group of 1 to 10 carbon atoms, a cycloalkyl group of 3 to 11 carbon atoms, an aromatic hydrocarbon group of 6 to 12 carbon atoms, or an aromatic heterocyclic group of 3 to 11 carbon atoms; however, in formulas (1a-1), (1a-2), (1a-4), and (1a-6), $R_3$ may form a fused ring together with the six-membered ring to which $R_3$ is linked.

Preferred among the indolocarbazole compounds represented by general formula (1) are indolocarbazole compounds represented by the following general formulas (2) to (7).

(3)

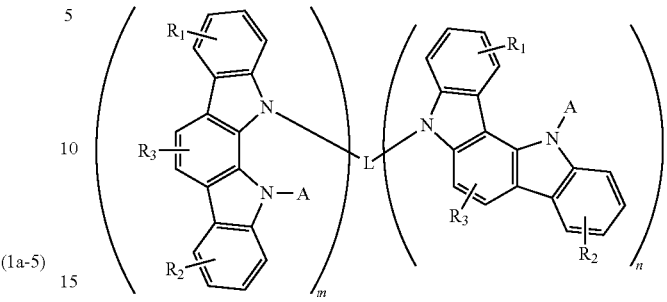

(4)

(5)

(6)

(2)

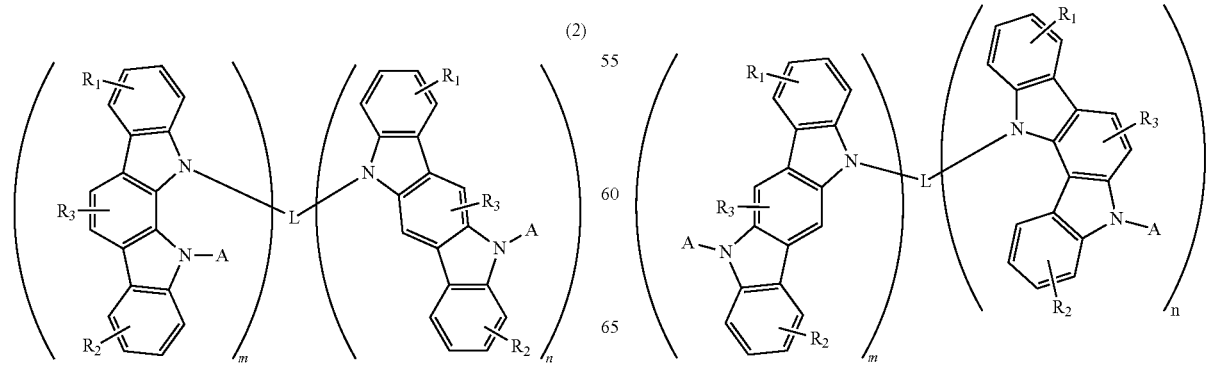

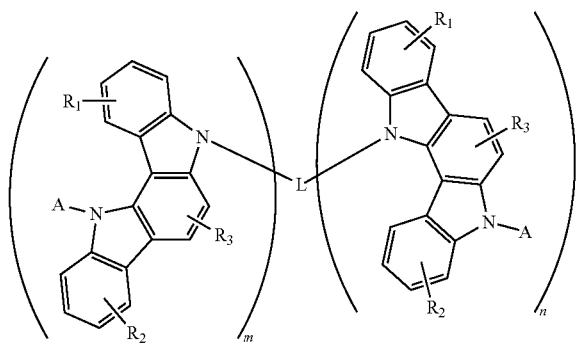

(7)

In general formulas (2) to (7), L, A, $R_1$ to $R_3$, m, and n have the same meaning as those in general formula (1) and formulas (1a-1) to (1a-6).

In the indolocarbazole compounds represented by general formulas (2) to (7), it is more preferable that m and n are respectively 1.

Moreover, it is preferable that the aforementioned organic electroluminescent device comprises a light-emitting layer containing the aforementioned indolocarbazole compound and a phosphorescent dopant.

PREFERRED EMBODIMENTS OF THE INVENTION

Figure 1:
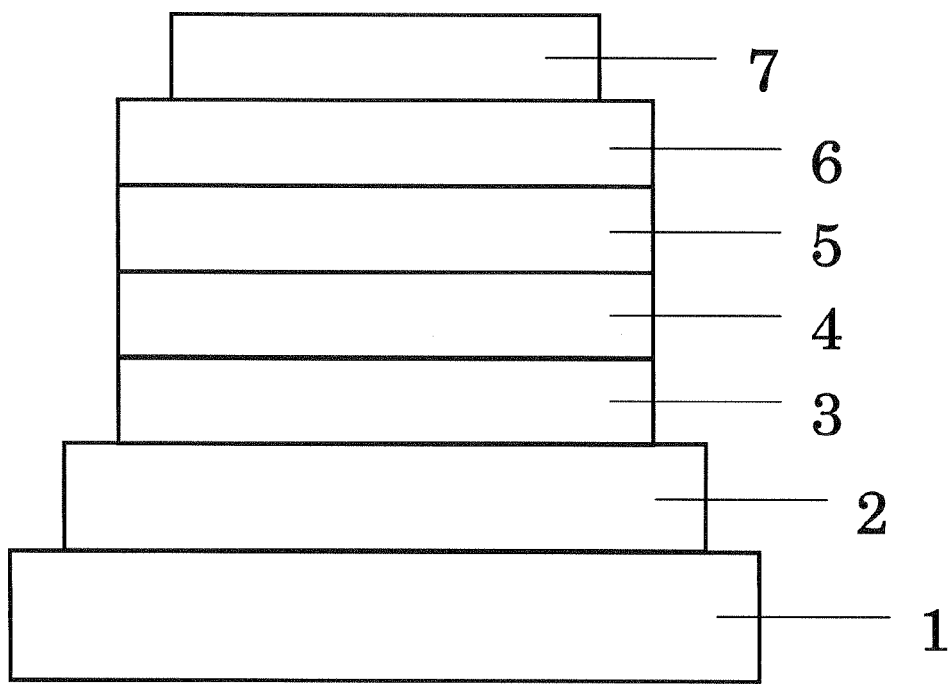
FIG. 1 shows an example of the structure of an organic EL device.

The indolocarbazole compound to be used in the organic electroluminescent device of this invention is an indolocarbazole compound represented by the aforementioned general formula (1). In general formula (1), L is an aromatic hydrocarbon group of 6 to 50 carbon atoms or an aromatic heterocyclic group of 3 to 50 carbon atoms and it is an (m+n+p+q)-valent group; each of $Y_1$ to $Y_4$ is represented by any one of formulas (1a-1) to (1a-6); m is an integer of 1 to 3, n is an integer of 1 to 3, p is an integer of 0 to 3, q is an integer of 0 to 3, and m+n+p+q is an integer of 2 to 6.

Each of $Y_1$ to $Y_4$ is a monovalent group which has an indolocarbazole skeleton substituted with $R_1$, $R_2$, $R_3$, and A and is linked to L via a nitrogen atom in the skeleton. The indolocarbazole skeleton is formed by fusion of 5 rings and there occur isomeric skeletons differing from one another in the position of fusion. The groups $Y_1$ to $Y_4$ are represented by formulas (1a-1) to (1a-6) and they are different from one another. At least two of $Y_1$ to $Y_4$ exist as groups different from each other. It is conceivable that a molecular structure formed by linking two or more different isomeric indolocarbazole skeletons by a specified linking group or by linking identical isomeric skeletons in an unsymmetrical manner has produced the aforementioned excellent effect.

In general formula (1), L is an aromatic hydrocarbon group of 6 to 50 carbon atoms or an aromatic heterocyclic group of 3 to 50 carbon atoms. Specific examples of L include (m+n+p+q)-valent groups formed by removing (m+n+p+q) hydrogen atoms from benzene, naphthalene, fluorene, anthracene, phenanthrene, fluoranthene, pyrene, chrysene, pyridine, pyrimidine, triazine, quinoline, isoquinoline, quinoxaline, naphthyridine, carbazole, and acridine or from atomatic compounds in which a plurality of these aromatic rings are linked together. Preferable examples include (m+n+p+q)-valent groups formed by removing (m+n+p+q) hydrogen atoms from benzene, pyridine, pyrimidine, triazine, naphthalene, and carbazole or from aromatic compounds in which a plurality of these aromatic rings are linked together. In the case where a plurality of the aforementioned aromatic rings are linked together, the aromatic rings may be identical with or different from one another. Specific examples of the groups formed by removing hydrogen atoms from the aforementioned aromatic compounds in which a plurality of aromatic rings are linked together include (m+n+p+q)-valent groups formed from biphenyl, terphenyl, bipyridine, bipyrimidine, bitriazine, bistriazylbenzene, binaphthalene, phenylpyridine, diphenylpyridine, diphenylpyrimidine, diphenyltriazine, phenylcarbazole, and pyridylcarbazole. The position of linkage of $Y_1$, $Y_2$, $Y_3$, or $Y_4$ to L is not limited and it may be on a terminal ring or a ring in the middle. The aforementioned aromatic hydrocarbon group or aromatic heterocyclic group may have a substituent; when a substituent is present, preferable examples thereof include an alkyl group of 1 to 4 carbon atoms, a cycloalkyl group of 3 to 6 carbon atoms, an alkoxyl group of 1 to 2 carbon atoms, an acetyl group, and a diarylamino group of 6 to 24 carbon atoms.

When the groups derived from aromatic compounds in which a plurality of aromatic rings are linked together are divalent, such divalent groups are represented, for example, by the following formulas (11) to (13).

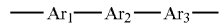

(11)

(12)

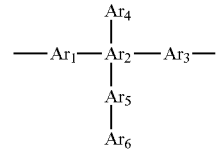

(13)

(In formulas (11) to (13), each of $Ar_1$ to $Ar_6$ is an unsubstituted monocyclic or fused aromatic ring.)

In the case where L, A, $R_1$, $R_2$, or $R_3$ has a substituent, the total number of such a substituent is 1 to 10, preferably 1 to 6, more preferably 1 to 4. In the case where L, A, $R_1$, $R_2$, or $R_3$ has two substituents or more, the substituents may be identical with or different from one another. In counting the number of carbon atoms in L, A, $R_1$, $R_2$, or $R_3$ when it has a substituent, the number of carbon atoms in the substituent is included.

In general formula (1), $Y_1$ to $Y_4$ are respectively represented by formulas (1a-1) to (1a-6). In formulas (1a-1) to (1a-6), each of $R_1$, $R_2$, and $R_3$ is independently a hydrogen atom, an alkyl group of 1 to 10 carbon atoms, a cycloalkyl group of 3 to 11 carbon atoms, an aromatic hydrocarbon group of 6 to 12 carbon atoms, or an aromatic heterocyclic group of 3 to 11 carbon atoms; preferably a hydrogen atom, an alkyl group of 1 to 4 carbon atoms, a cycloalkyl group of 3 to 6 carbon atoms, a phenyl group, a naphthyl group, a carbazolyl group, a quinolyl group, or an isoquinolyl group; more preferably a hydrogen atom, a phenyl group, or a carbazolyl group.

In formulas (1a-1), (1a-2), (1a-4), and (1a-6), $R_3$ may form a fused ring together with the six-membered ring in the center constituting the indolocarbazole skeleton. When $R_3$ is fused to the aforementioned six-membered ring, $R_3$ may be a fused ring. In this case, $R_3$ is preferably an indole ring and the fusion thereof results in the formation of a diindolocarbazole compound. Here, the said indole ring may have a substituent. In the case where $R_3$ is a group fusible to the aforementioned six-membered ring, the ring remaining after removal of the aforementioned six-membered ring from the finished fused ring may be a pyrrole ring, a furan ring, a thiophene ring, an indole ring, a benzofuran ring, a benzothiophene ring, a benzene ring, or a naphthalene ring. These rings may have a substituent. An indole ring optionally having a substituent is preferred and, in this particular case, such an indole ring forms a carbazole ring with the aforementioned six-membered ring. The fusion of $R_3$ to the aforementioned six-membered ring occurs when the carbon atom adjacent to the position of linkage of $R_3$ to the six-membered ring has a replaceable hydrogen atom.

Each A is a monovalent group and is independently an alkyl group of 1 to 10 carbon atoms, a cycloalkyl group of 3 to 11 carbon atoms, an aromatic hydrocarbon group of 6 to 50 carbon atoms, or an aromatic heterocyclic group of 3 to 50 carbon atoms. Preferable examples of A include monovalent groups formed by removing a hydrogen atom from benzene, naphthalene, fluorene, anthracene, phenanthrene, fluoranthene, pyrene, chrysene, pyridine, pyrimidine, triazine, quinoline, isoquinoline, quinoxaline, naphthyridine, carbazole, and acridine or from aromatic compounds in which a plurality of these compounds are linked together. More preferable examples include monovalent groups formed by removing a hydrogen atom from benzene, pyridine, pyrimidine, triazine, naphthalene, and carbazole or from aromatic compounds in which a plurality of these compounds are linked together. In the case where a plurality of aromatic compounds are linked together, these compounds may be identical with or different from one another. Specific examples of groups formed by removing a hydrogen atom from aromatic compounds in which a plurality of compounds are linked together include monovalent groups formed from biphenyl, terphenyl, bipyridine, bipyrimidine, bitriazine, bistriazylbenzene, phenylpyridine, diphenylpyridine, diphenylpyrimidine, diphenyltriazine, phenylcarbazole, and pyridylcarbazole. The aforementioned alkyl group, cycloalkyl group, aromatic hydrocarbon group, or aromatic heterocyclic group may have a substituent. In the case where any of the groups has a substituent, preferable examples of such a substituent include an alkyl group of 1 to 4 carbon atoms, an alkoxyl group of 1 to 2 carbon atoms, an acetyl group, an aryl group of 6 to 18 carbon atoms, and a heteroaryl group of 3 to 17 carbon atoms. More preferable examples include a phenyl group, a naphthyl group, a carbazolyl group, a quinolyl group, and an isoquinolyl group. The position of linkage of A to N in formulas (1a-1) to (1a-6) is not limited.

In general formula (1), m is an integer of 1 to 3, preferably 1 to 2, more preferably 1.

In general formula (1), n is an integer of 1 to 3, preferably 1 to 2, more preferably 1.

In general formula (1), p is an integer of 0 to 3, preferably 0 to 2, more preferably 0 or 1.

In general formula (1), q is an integer of 0 to 3, preferably 0 to 2, more preferably 0 or 1.

In general formula (1), the sum of m, n, p, and q is an integer of 2 to 6, preferably 2 to 4, more preferably 2 or 3.

Preferred among the indolocarbazole compounds represented by general formula (1) are indolocarbazole compounds represented by the aforementioned general formulas (2) to (7).

In general formulas (1) to (7) and formulas (1a-1) to (1a-6), it is to be understood that the same symbols and formulas have the same meaning unless otherwise specified. In general formulas (2) to (7), each of m and n is preferably 1 or 2, more preferably 1.

The indolocarbazole compounds represented by general formulas (1) to (7) can be synthesized by selecting raw materials according to the structure of the target compounds and employing known techniques.

For example, the indolocarbazole skeleton of the indolocarbazole compound represented by formula (1a-1) may be synthesized by the reaction shown below with reference to a synthetic example described in Synlett., 2005, No. 1, pp 42-48.

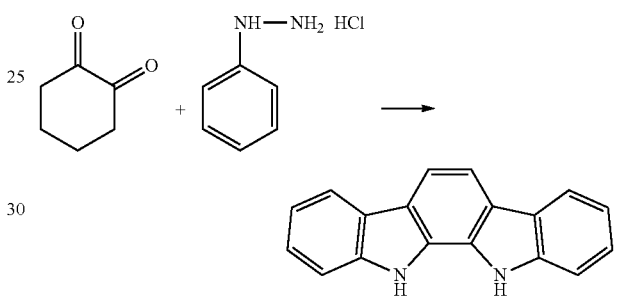

Further, the indolocarbazole skeleton represented by general formula (1a-2) may be synthesized by the reaction shown below with reference to a synthetic example described in Archiv der Pharmazie (Weinheim, Germany), 1987, 320 (3), pp 280-282.

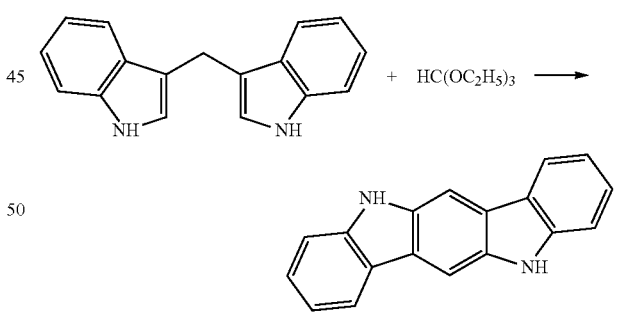

Still further, the indolocarbazole skeletons represented by general formulas (1a-3) and (1a-4) may be synthesized by the reactions shown below with reference to synthetic examples described in The Journal of Organic Chemistry, 2007, 72 (15), 5886 and Tetrahedron, 1999, 55, p 2371.

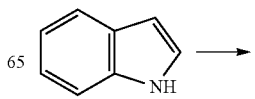

11

-continued

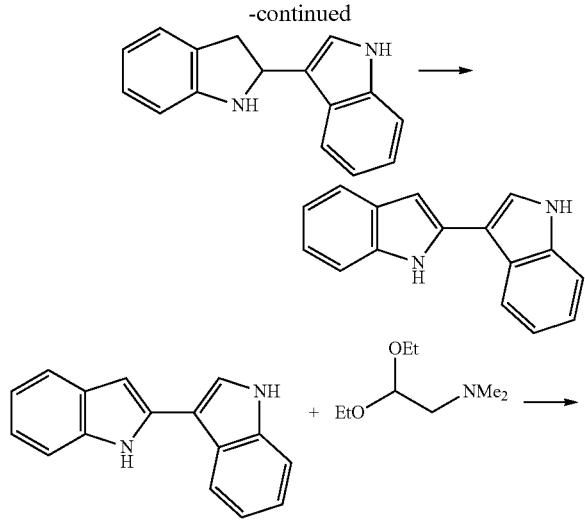

12

-continued

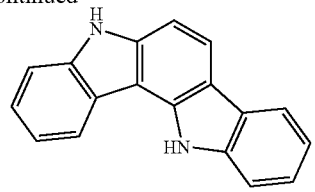

The indolocarbazole compounds prepared by the aforementioned reactions are submitted to a coupling reaction in the usual manner wherein the hydrogen atoms linked to the nitrogen atoms of the carbazole compound are replaced by the corresponding aromatic groups to yield a group of compounds represented by general formula (1) or by general formulas (2) to (7).

Specific examples of the indolocarbazole compounds represented by general formula (1) are illustrated below. However, the indolocarbazole compounds to be used in the organic electroluminescent devices of this invention are not limited thereto.

1-1

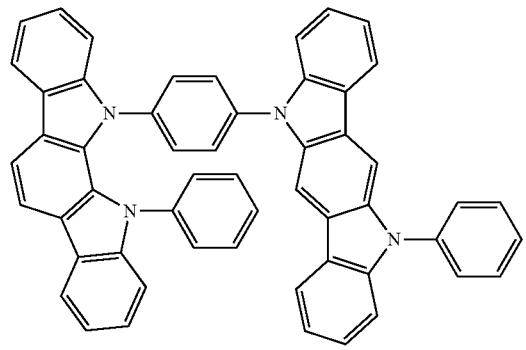

1-2

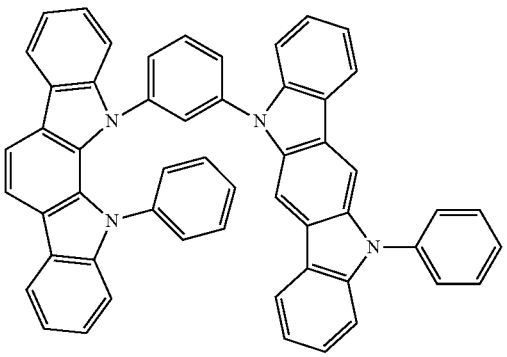

1-3

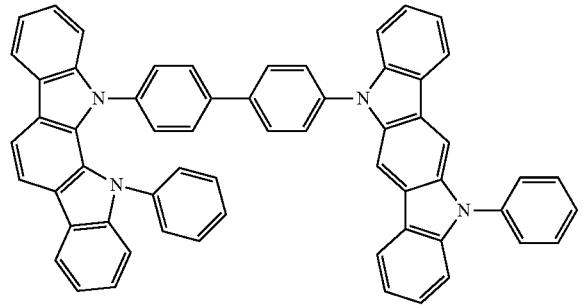

1-4

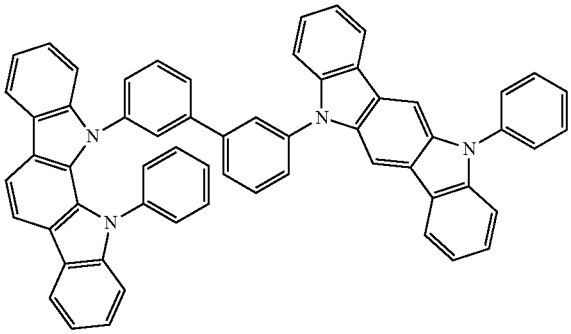

1-5

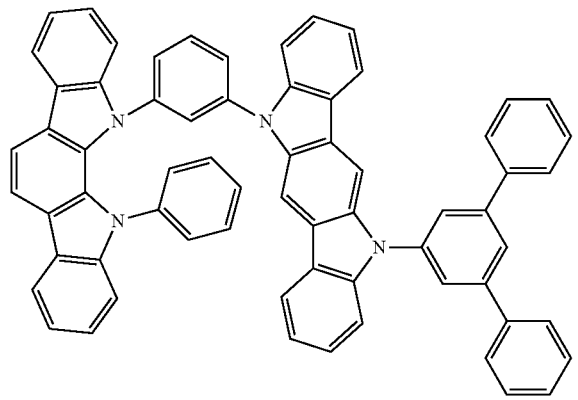

1-6

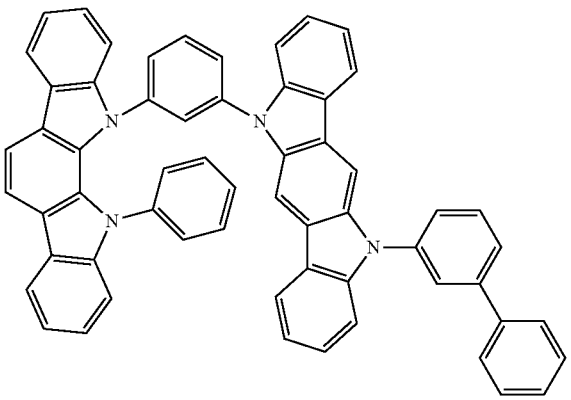

-continued
1-7
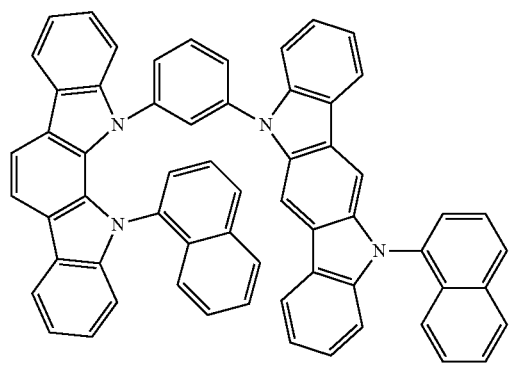
1-8
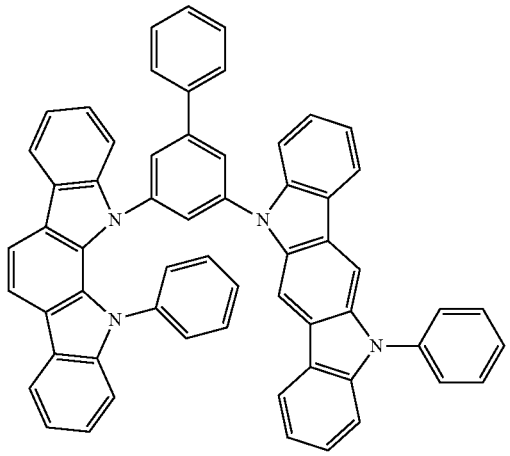
1-9
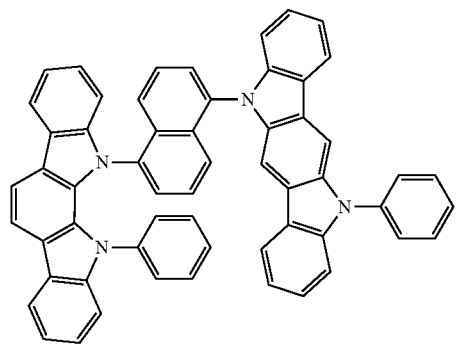
1-10
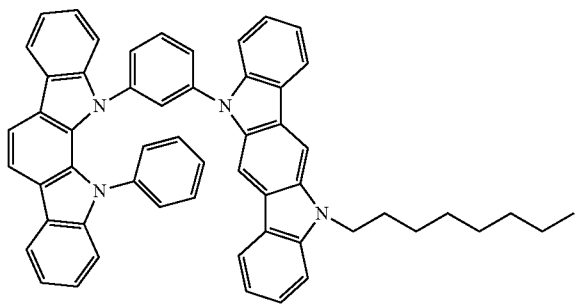
1-11
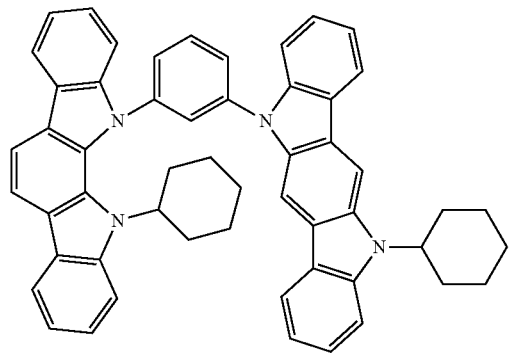
1-12
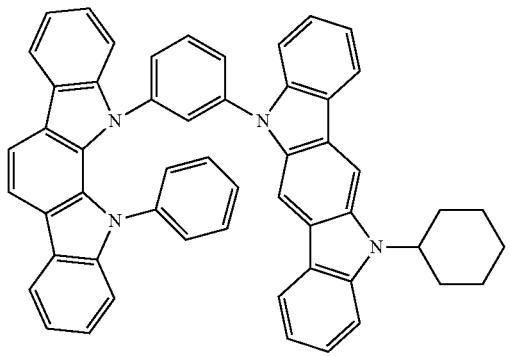
1-13
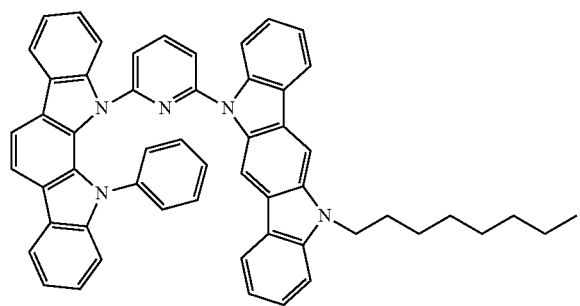
1-14
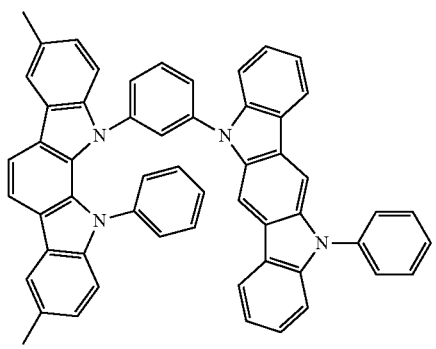

-continued
1-15
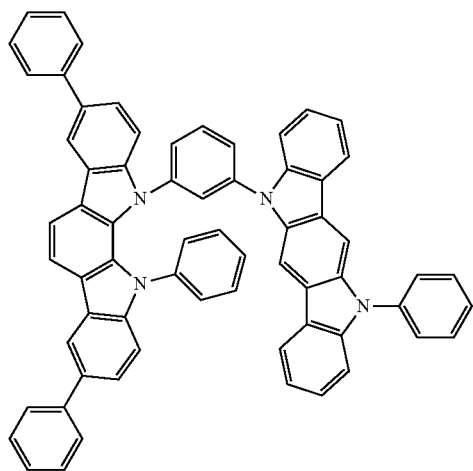
1-16
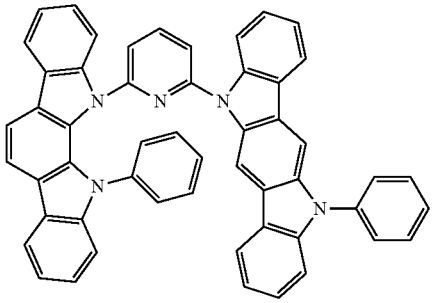
1-17
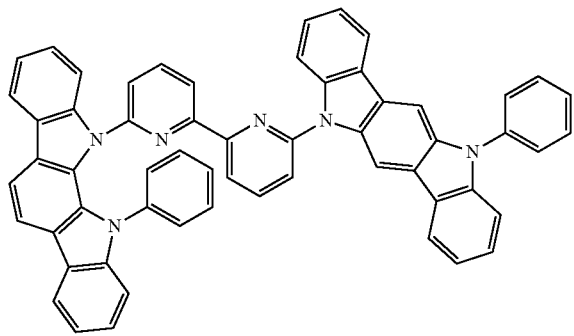
1-18
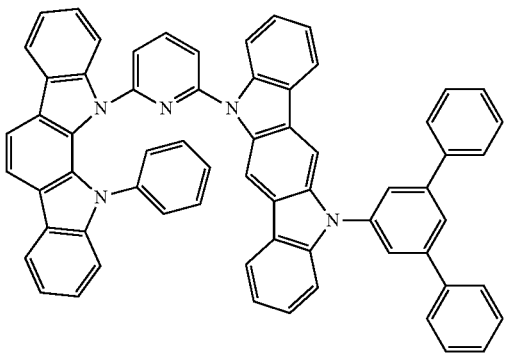
1-19
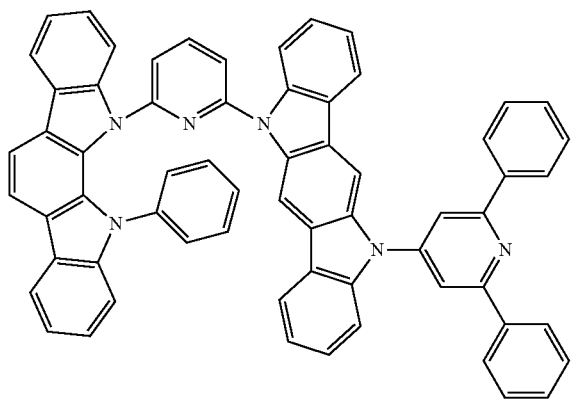
1-20
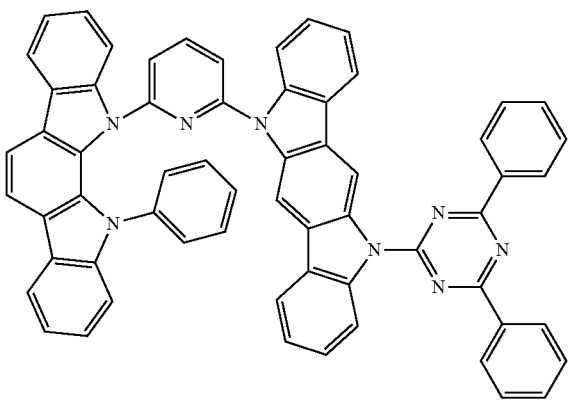

1-21 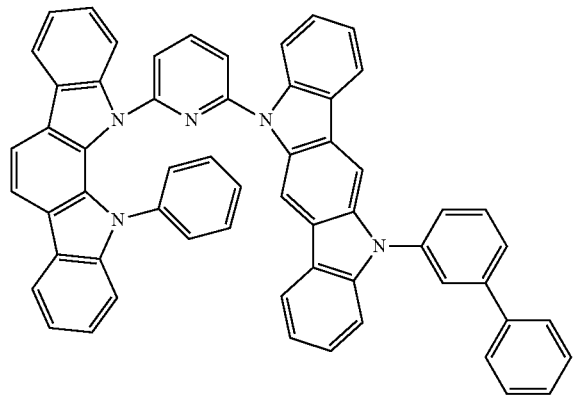
1-22 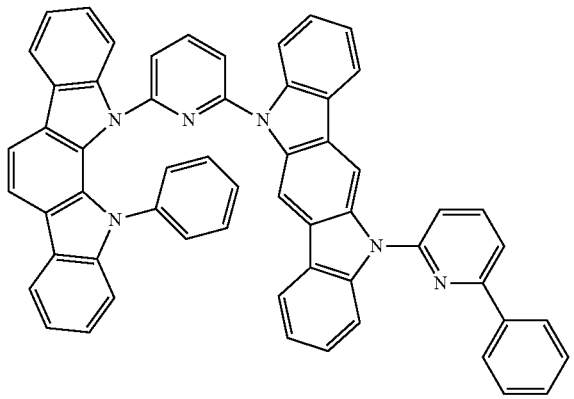
1-23 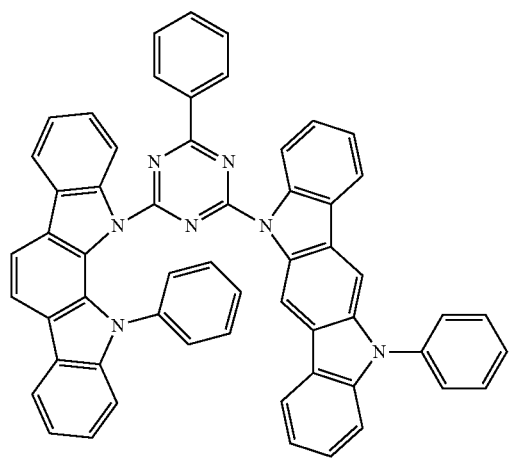
1-24 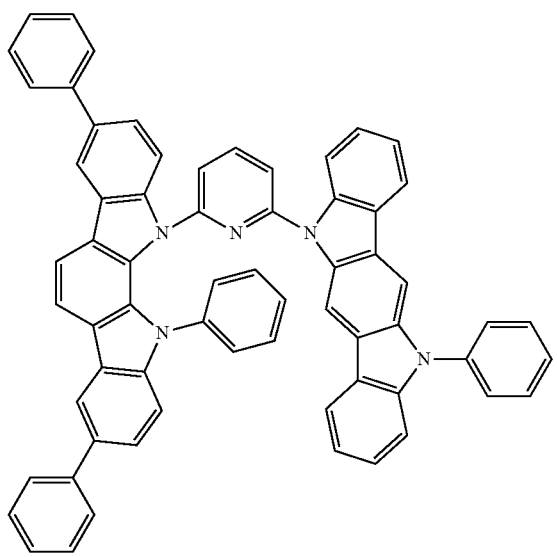
1-25 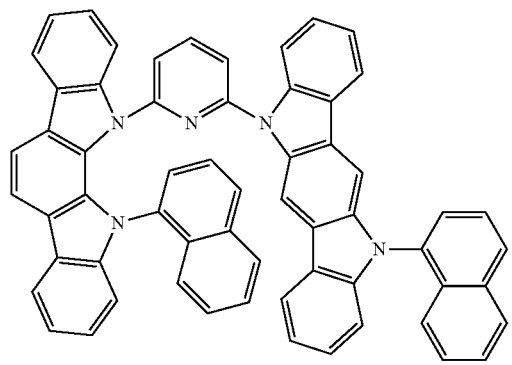
1-26 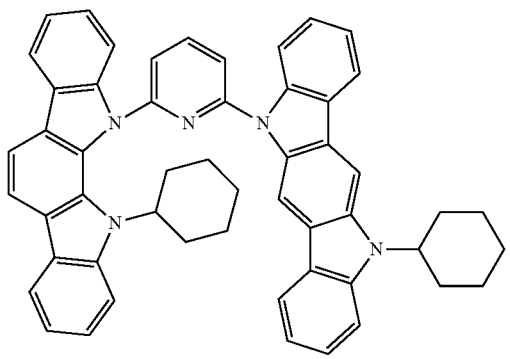

-continued
1-27
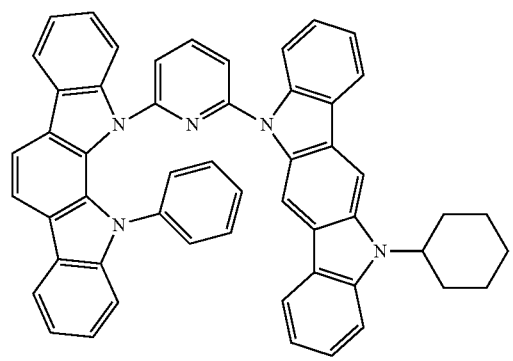
1-28
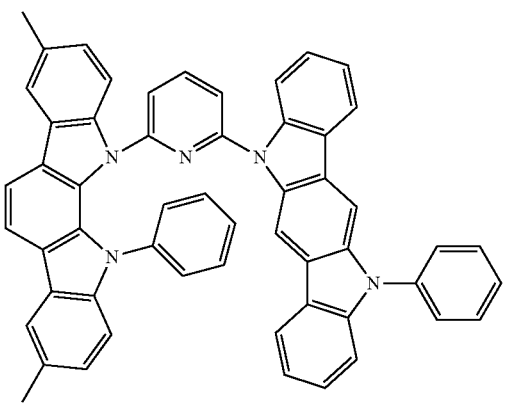
1-29
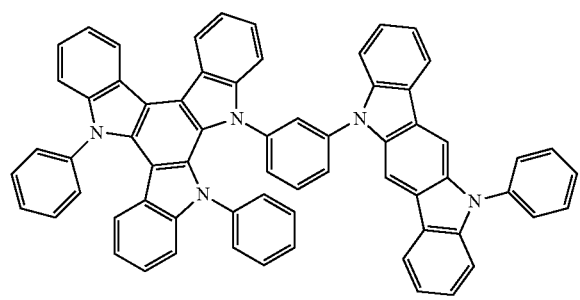
1-30
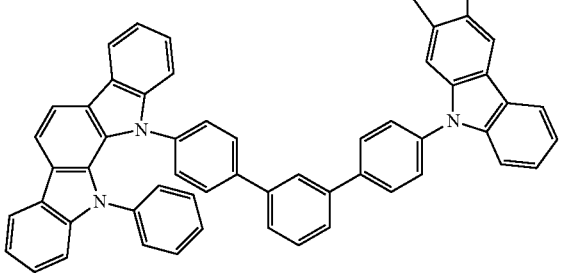
1-31
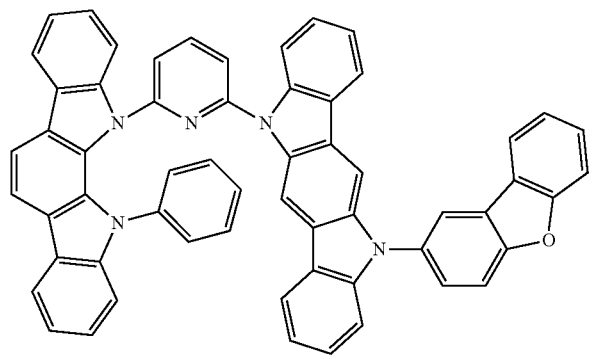
1-32
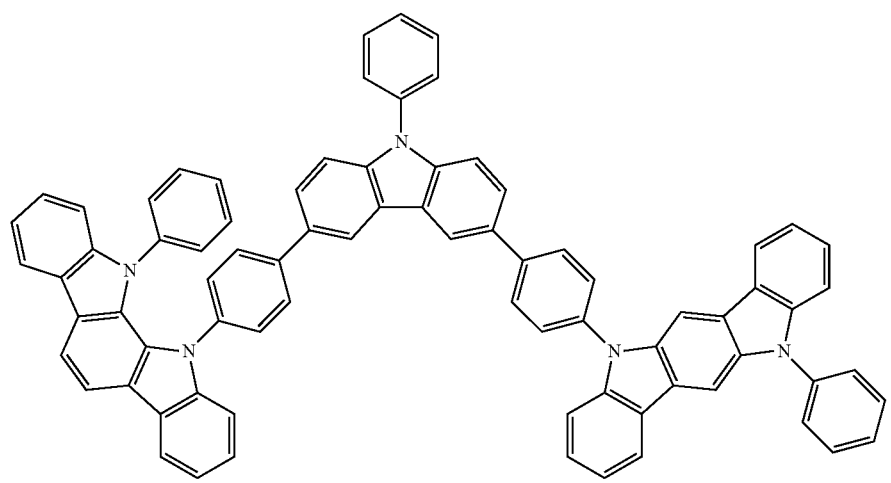

-continued
1-33
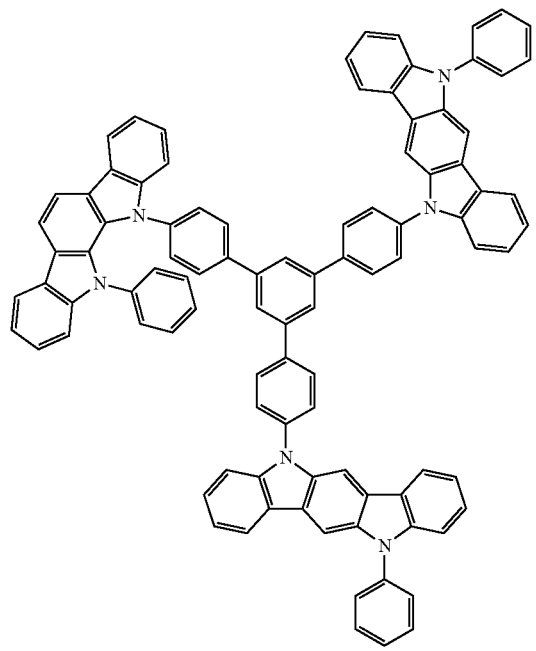
1-34
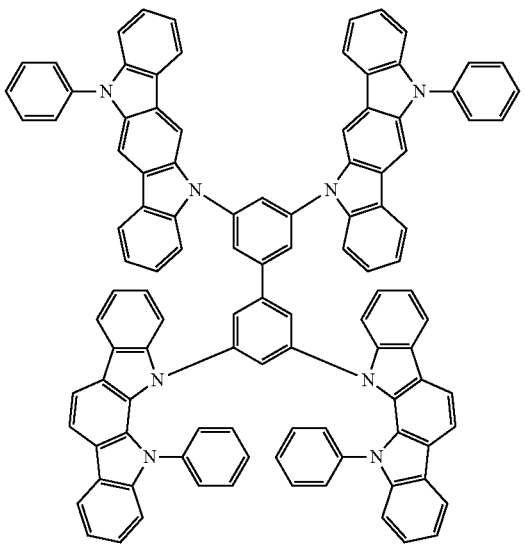
2-1
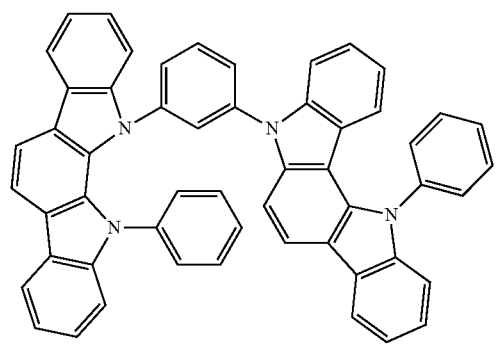
2-2
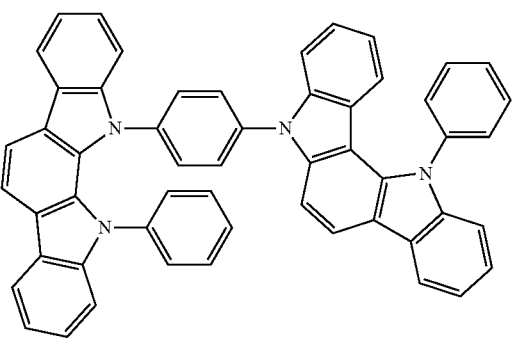
2-3
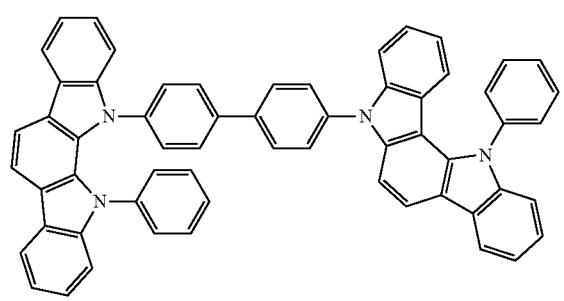
2-4
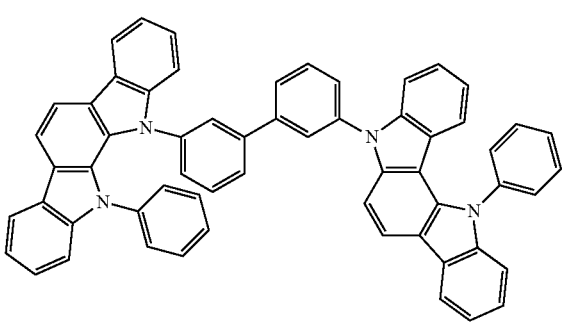

-continued
2-5
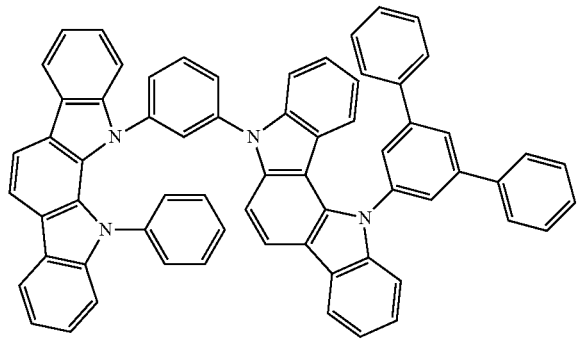
2-6
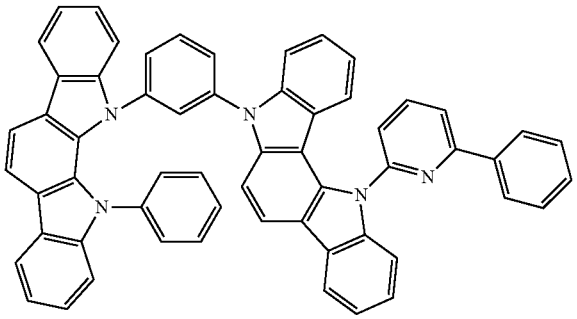
2-7
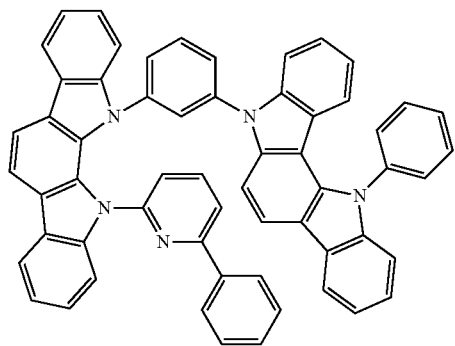
2-8
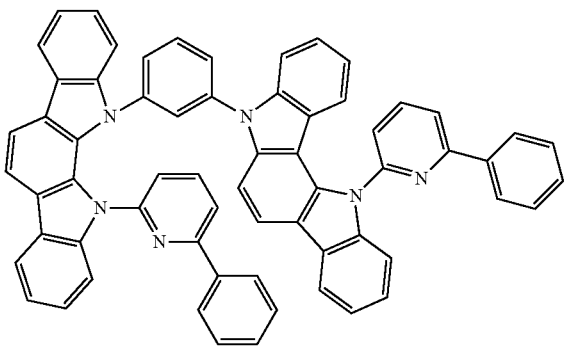
2-9
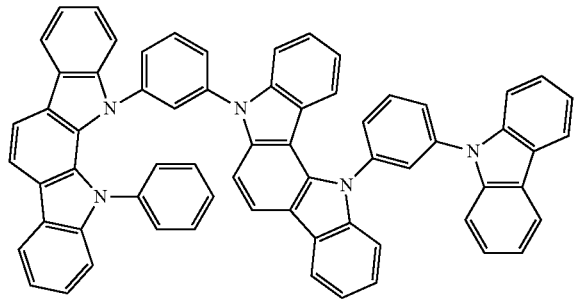
2-10
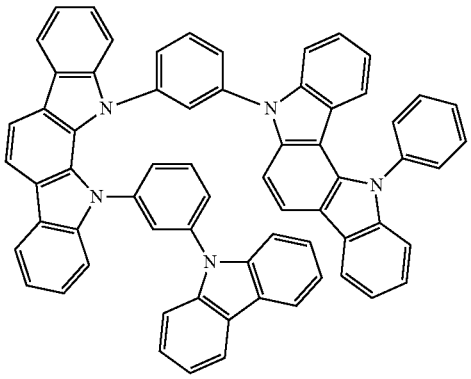
2-11
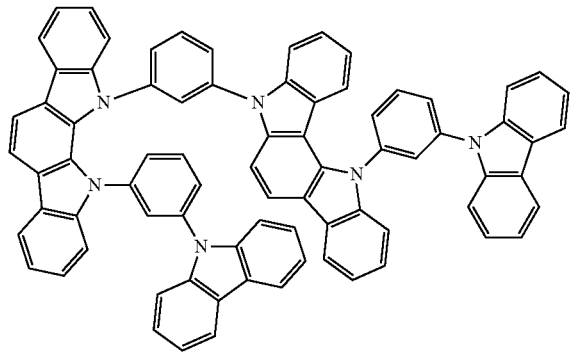
2-12
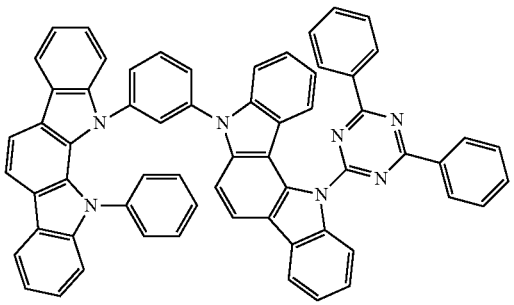

-continued
2-13
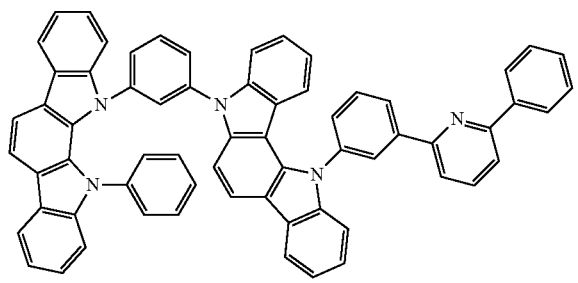
2-14
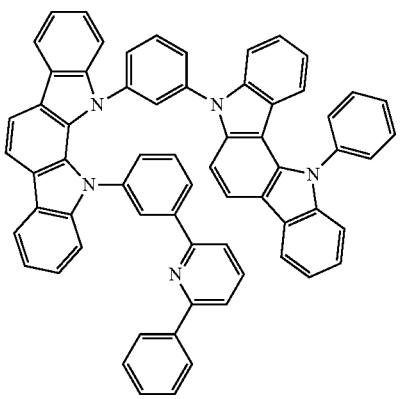
2-15
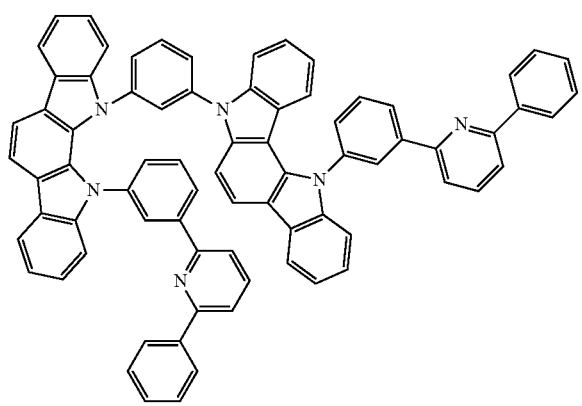
2-16
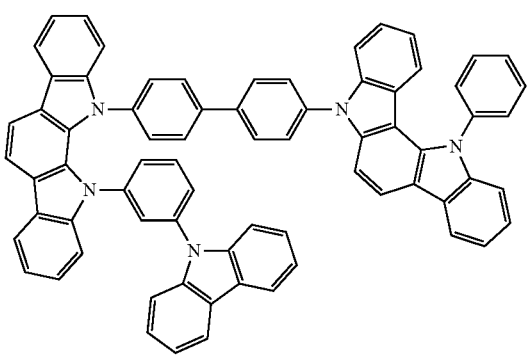
2-17
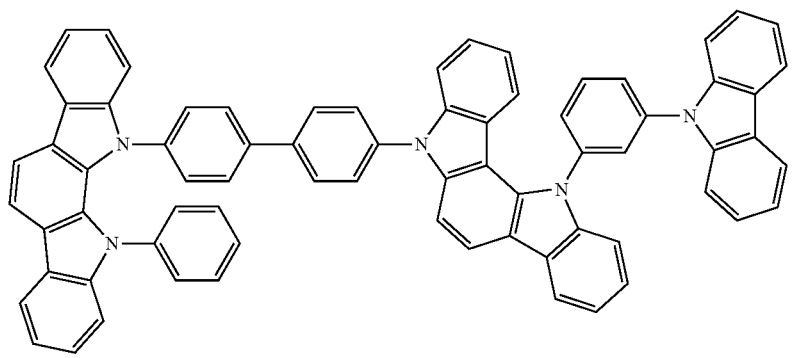
2-18
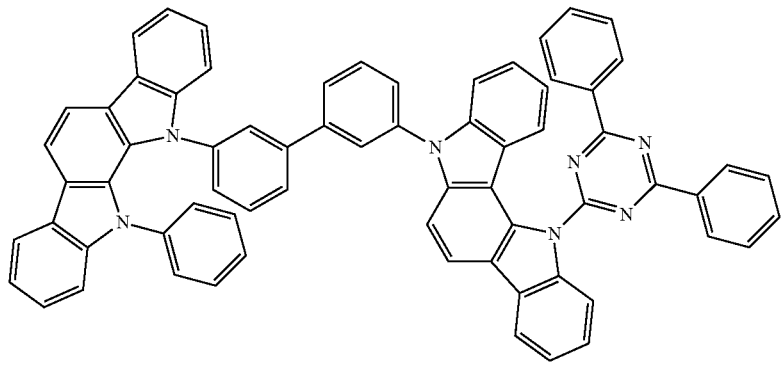

2-19
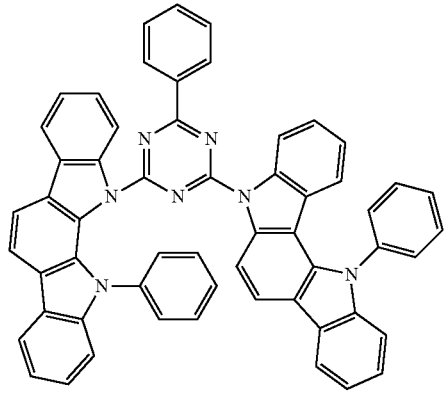
2-20
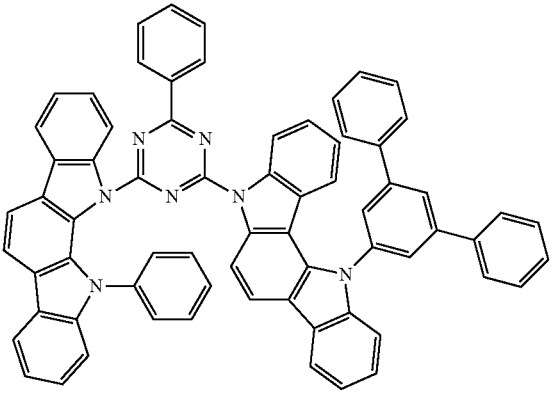
2-21
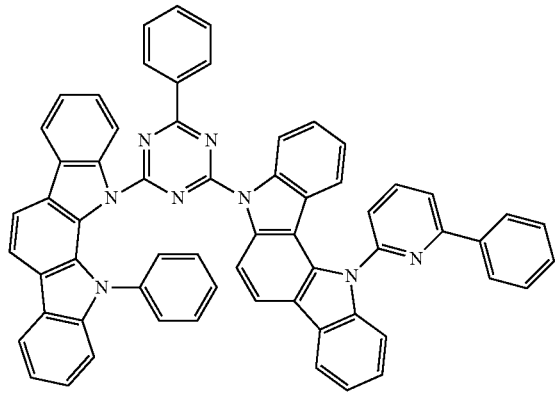
2-22
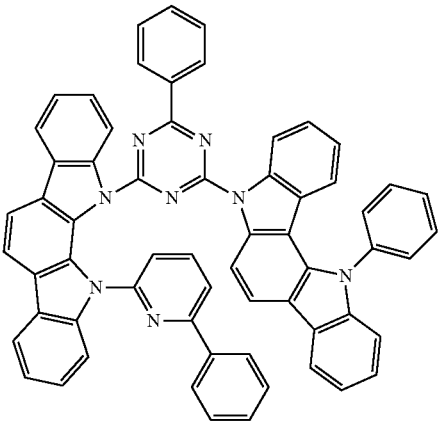
2-23
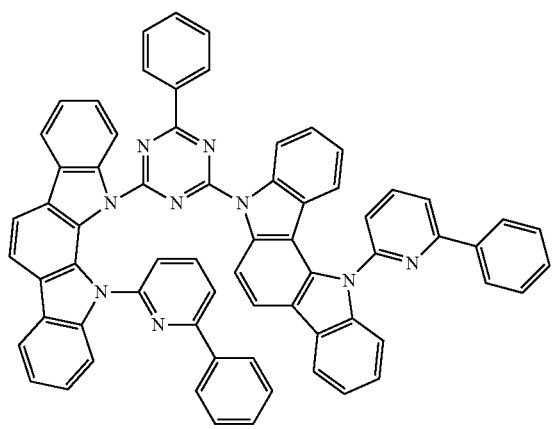
2-24
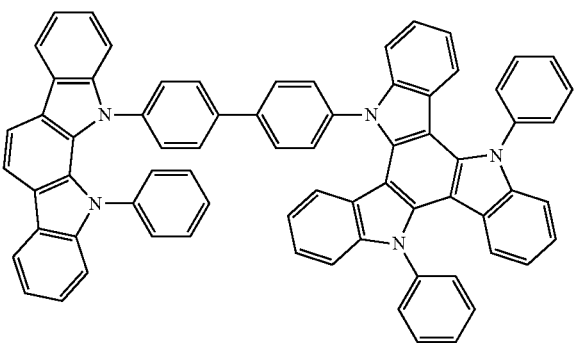

-continued
2-25
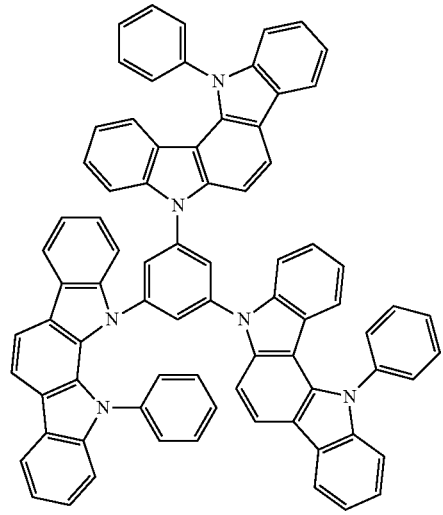
2-26
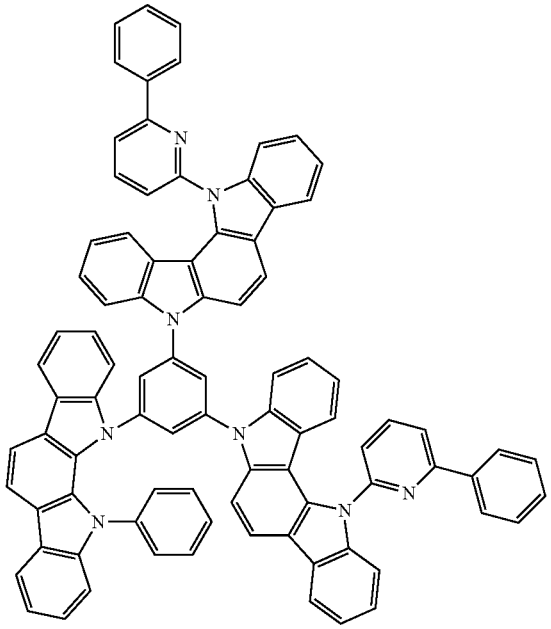
2-27
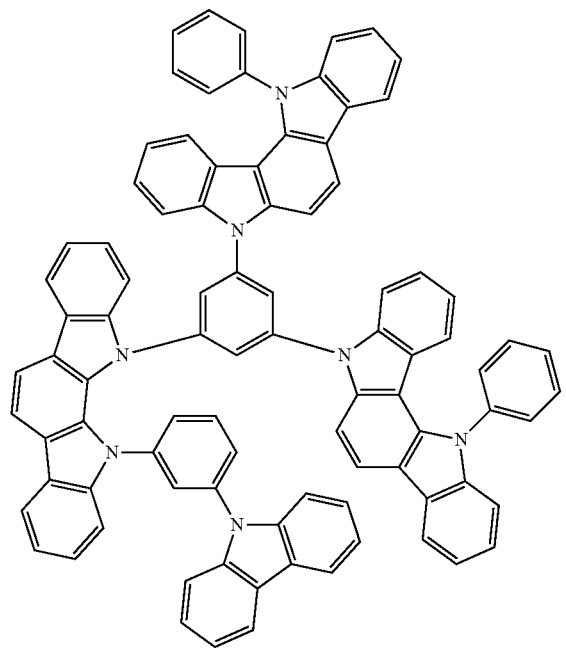
2-28
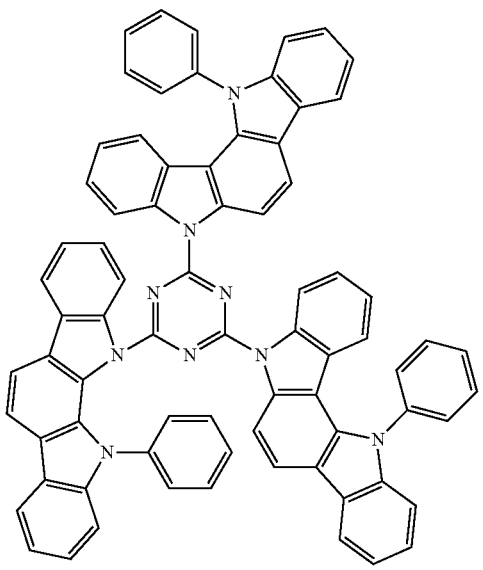

2-29
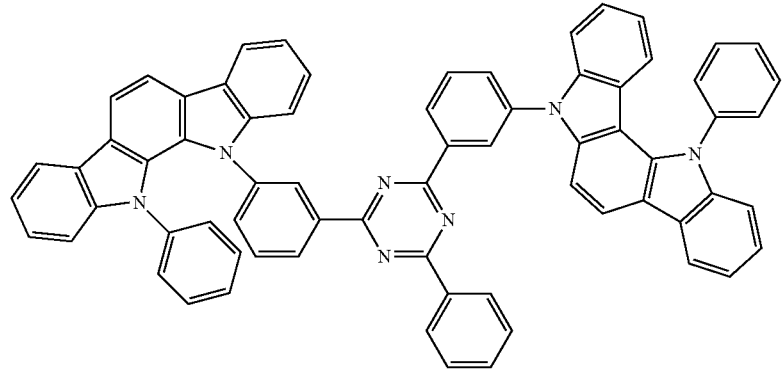
2-30
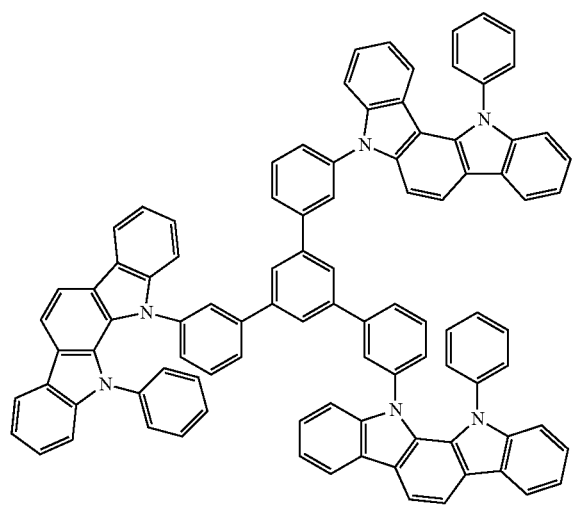
2-31
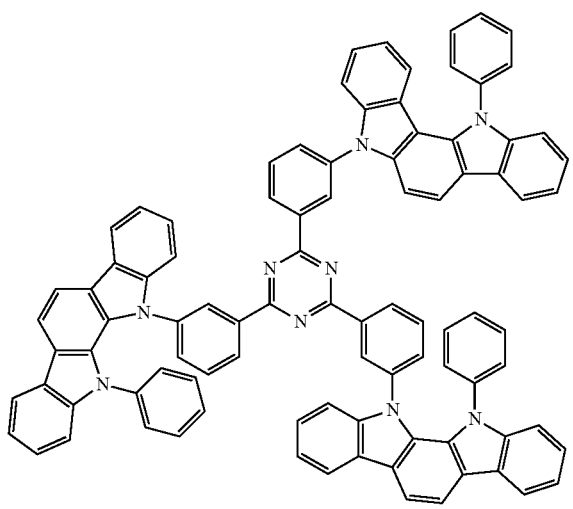
3-1
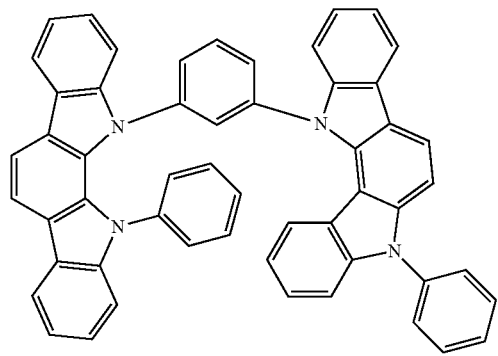
3-2
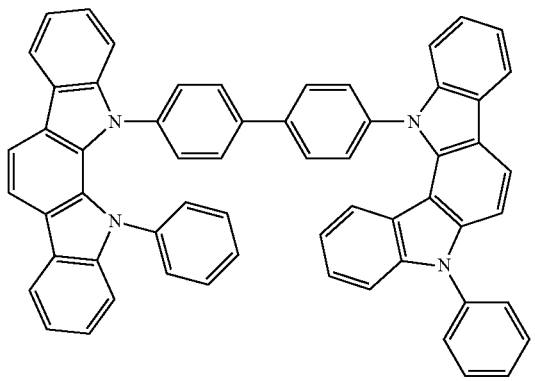

3-3
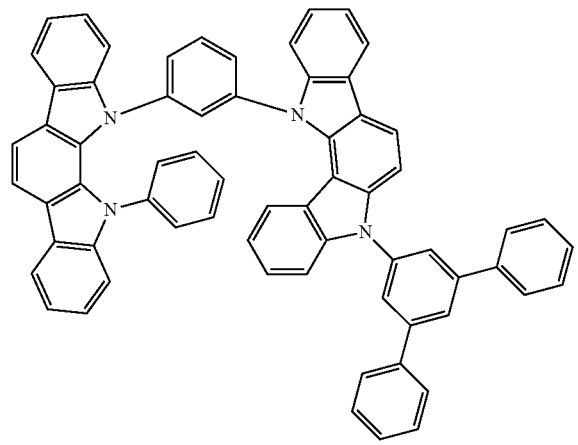
3-4
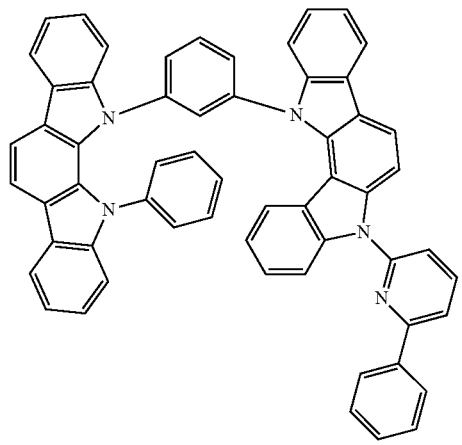
3-5
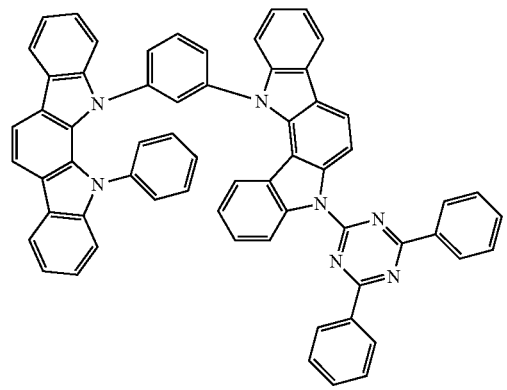
3-6
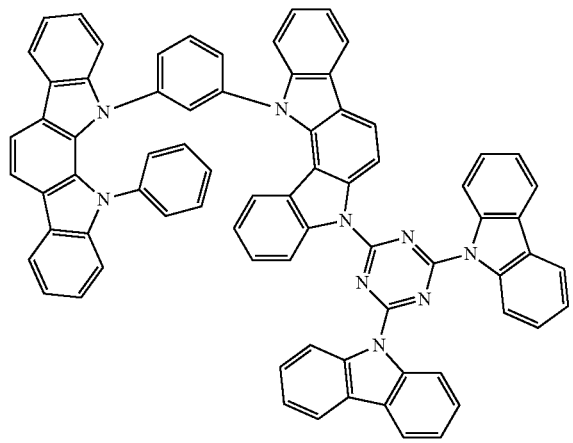
3-7
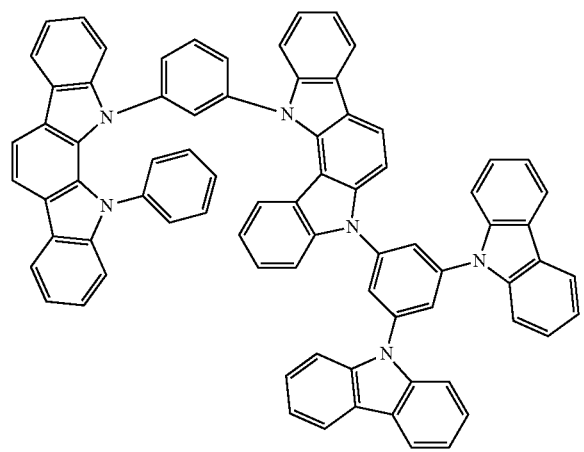
3-8
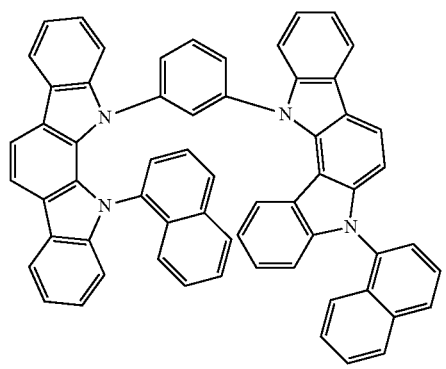

3-9
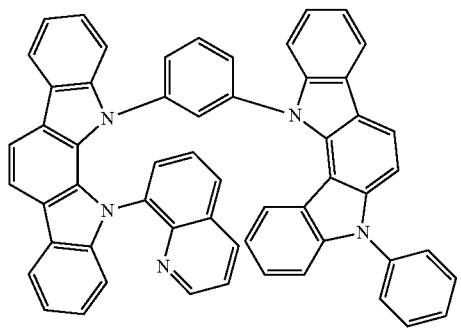
3-10
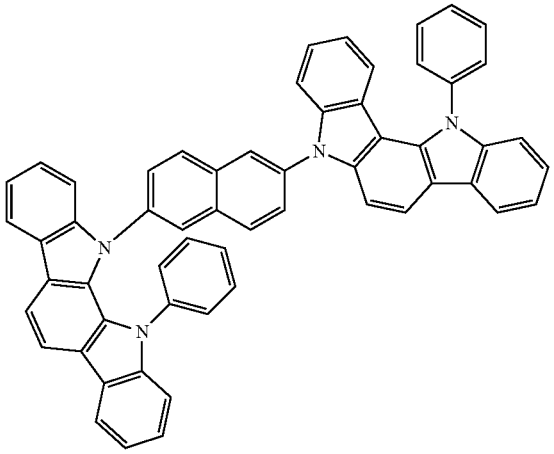
3-11
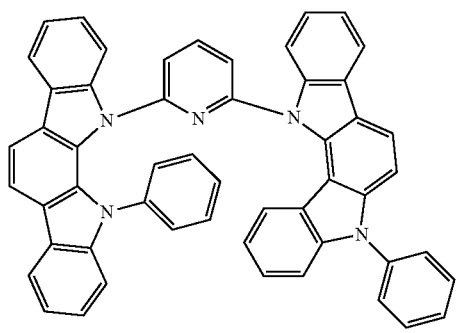
3-12
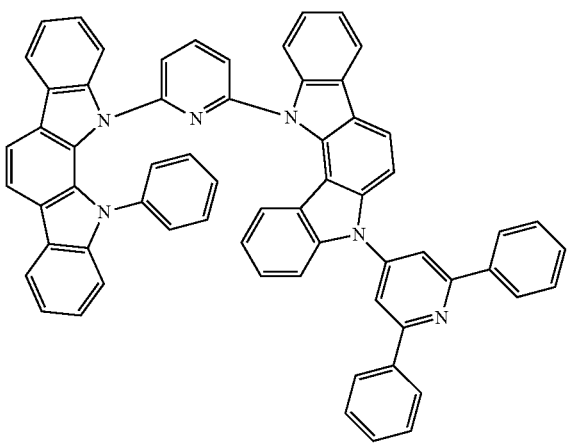
3-13
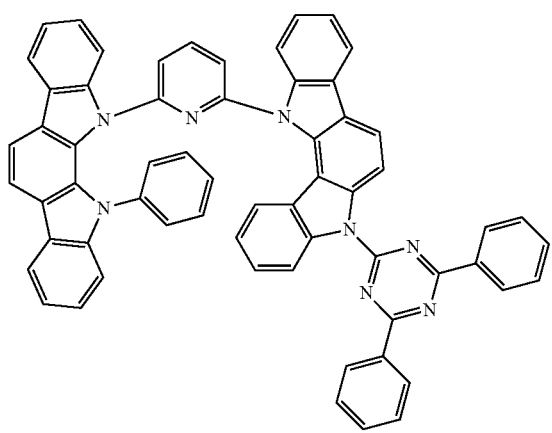
3-14
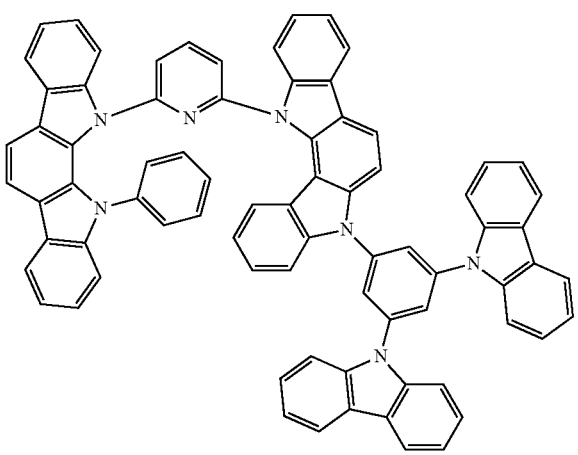

-continued
3-15
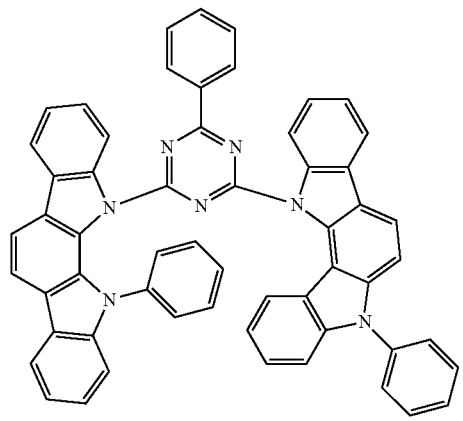
3-16
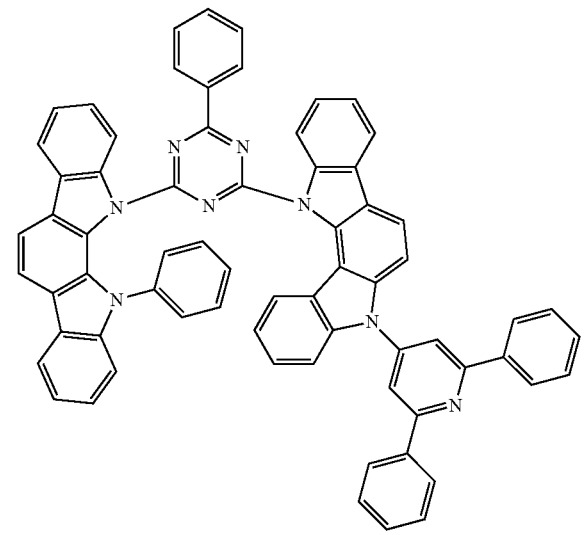
3-17
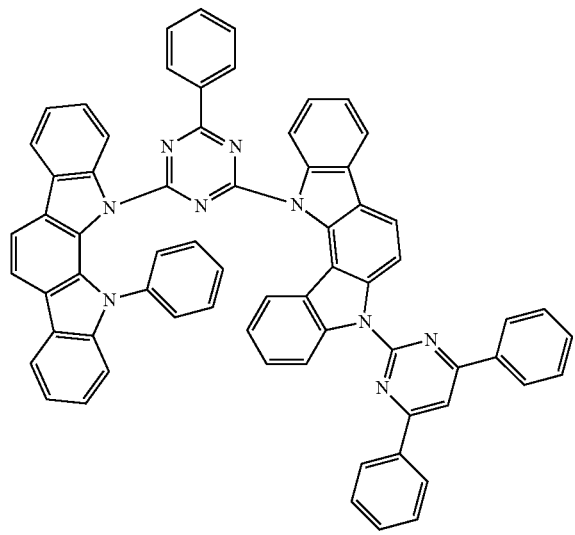
3-18
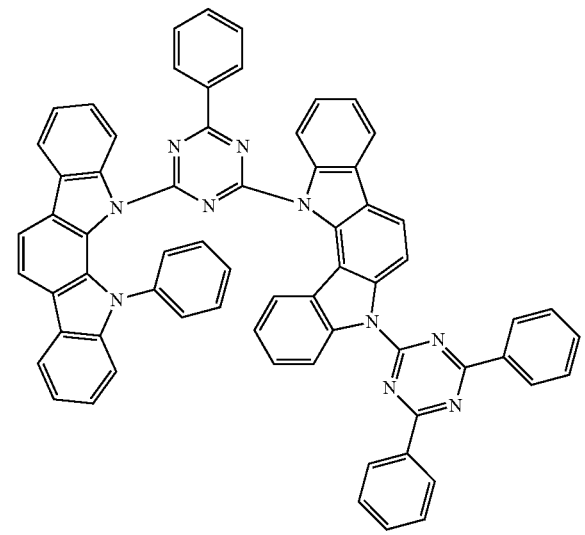
3-19
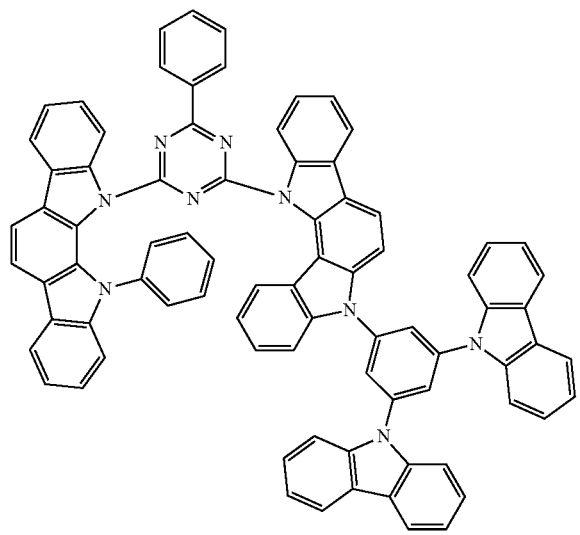
3-20
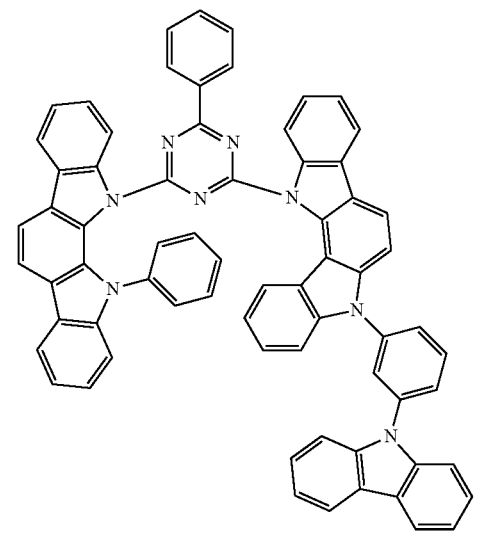

3-21
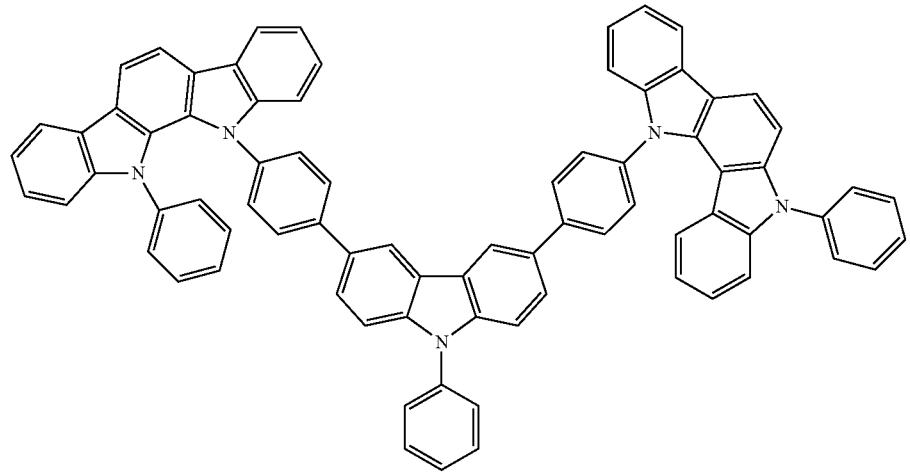
3-22
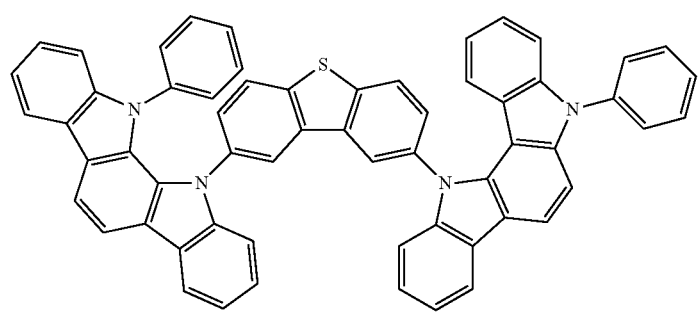
3-23
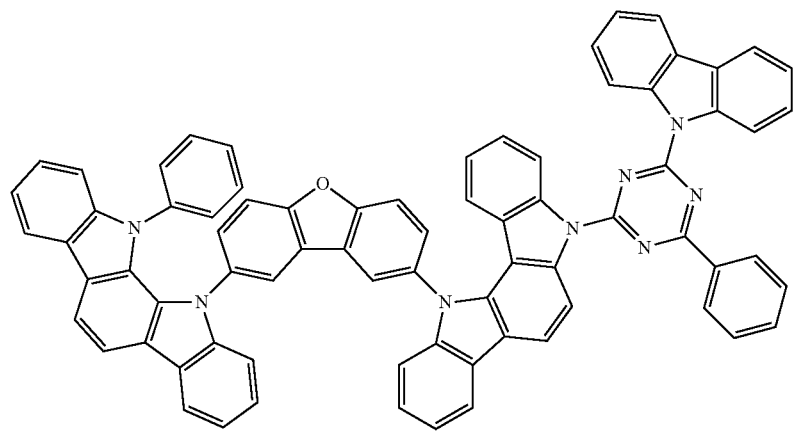
4-1
4-2
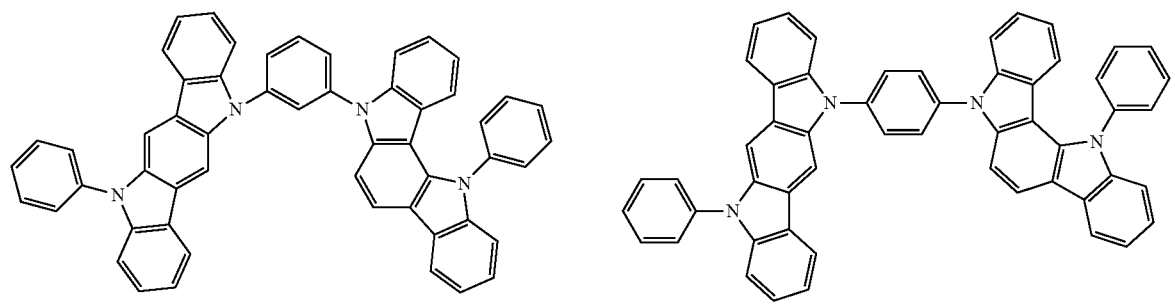

-continued
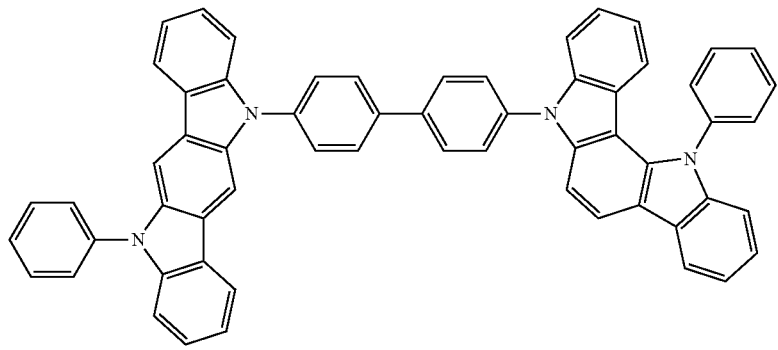
4-3
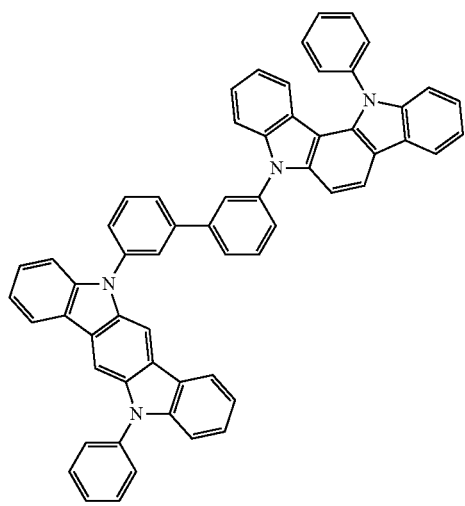
4-4
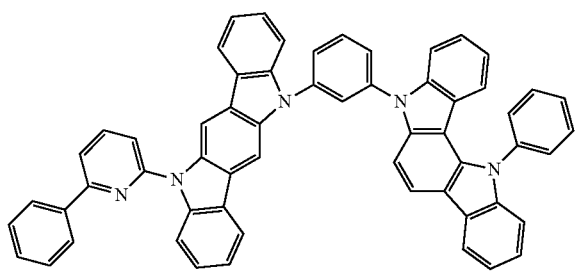
4-5
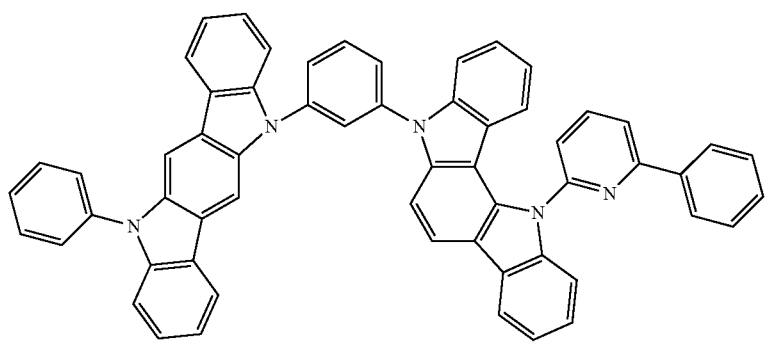
4-6
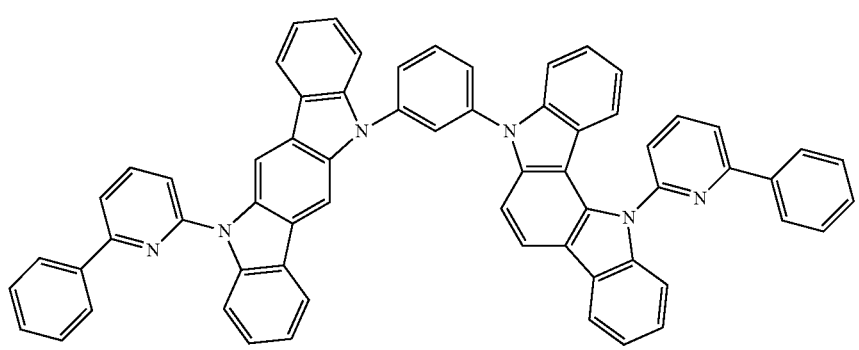
4-7

4-8
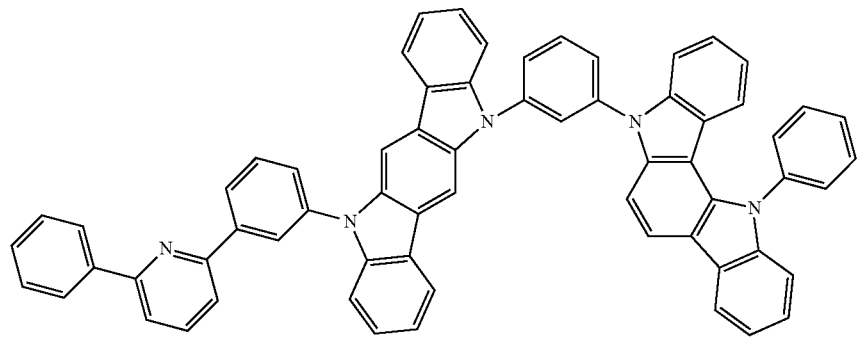
4-9
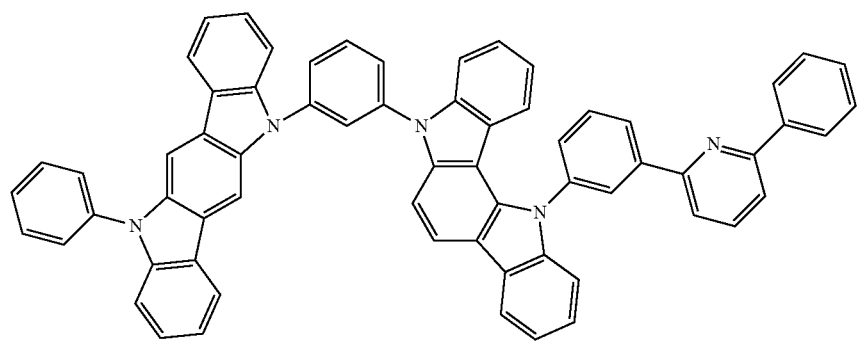
4-10
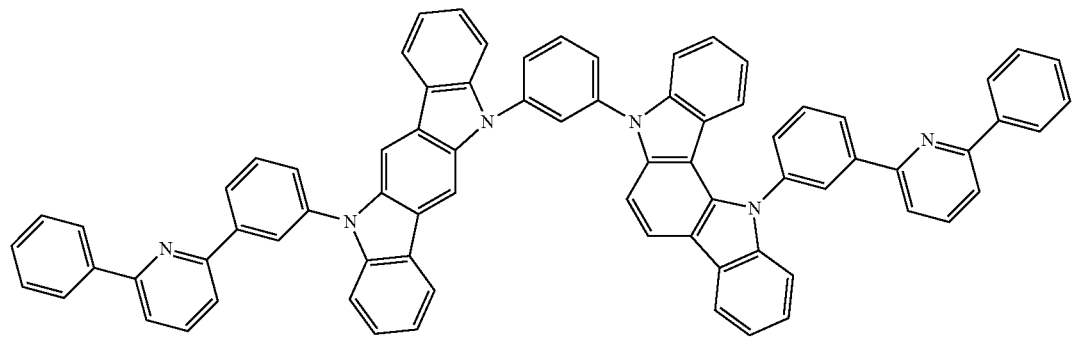
4-11
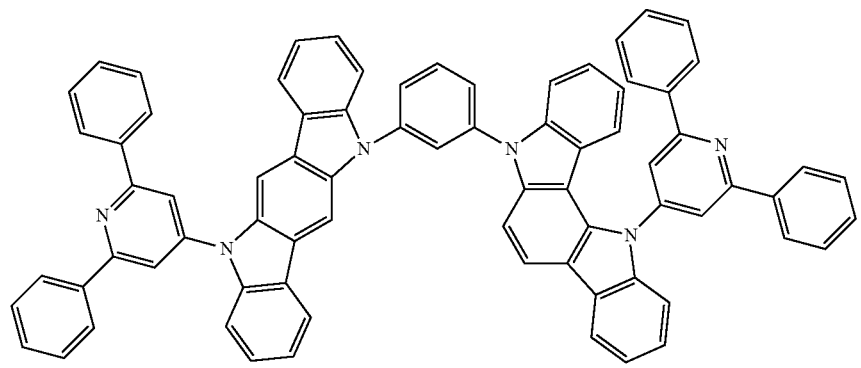

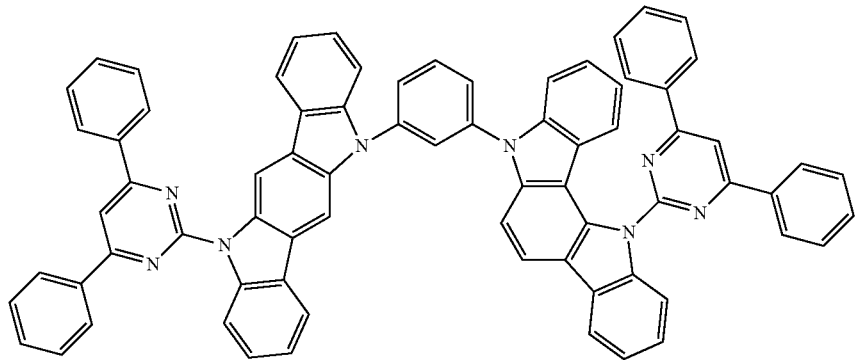
4-12
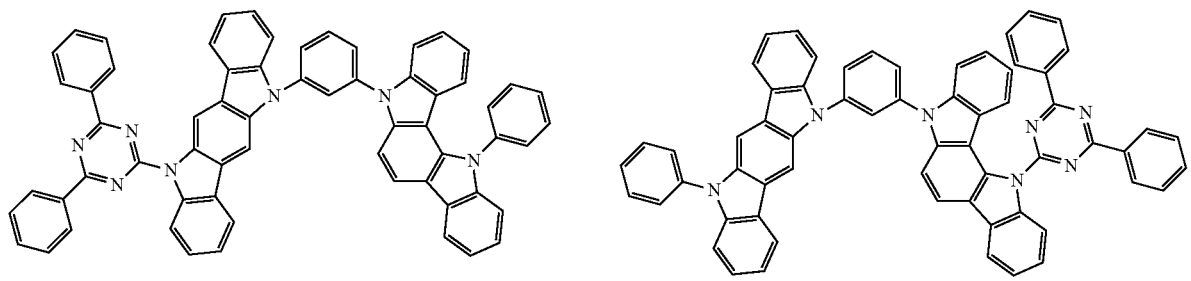
4-13    4-14
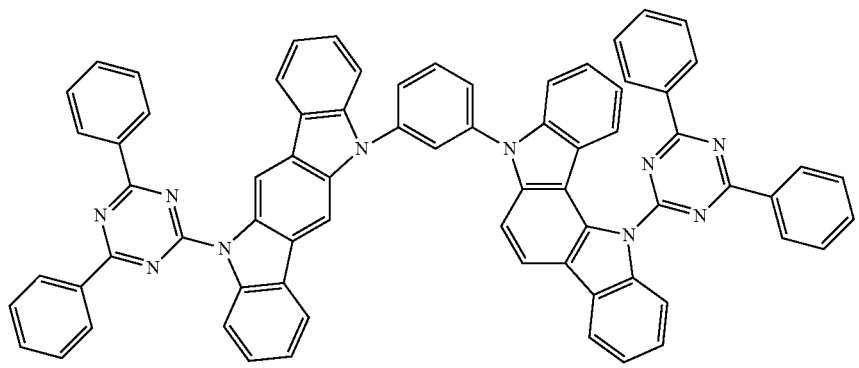
4-15
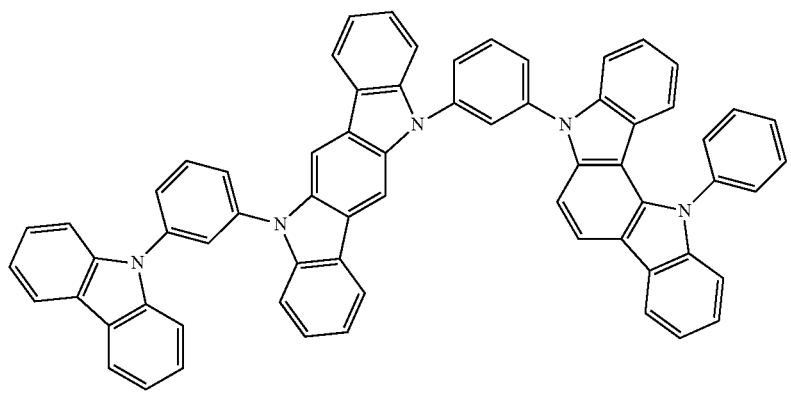
4-16

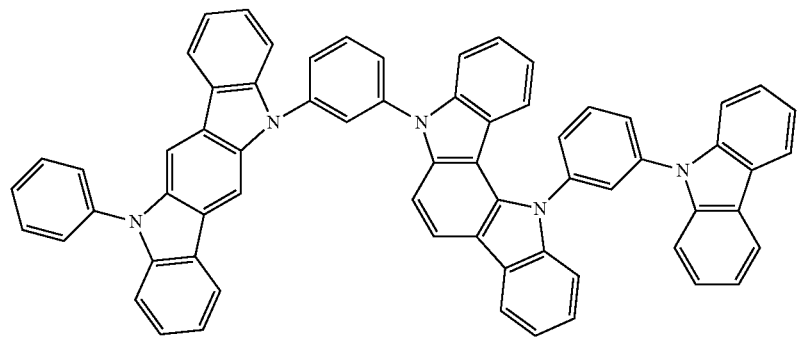
4-17
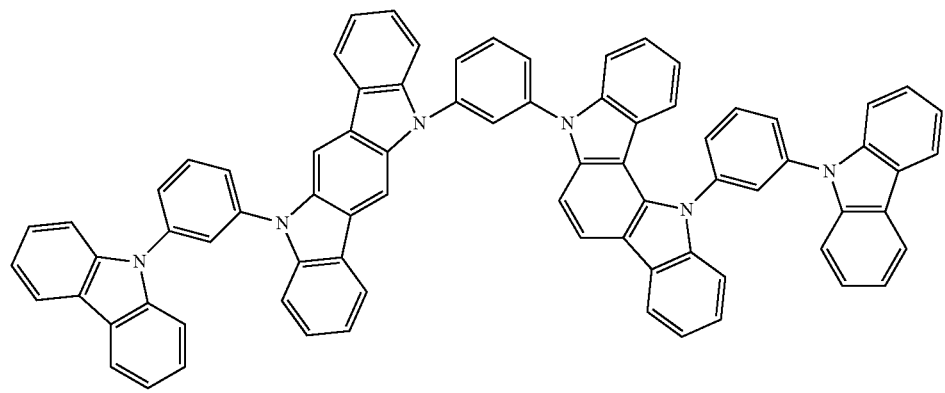
4-18
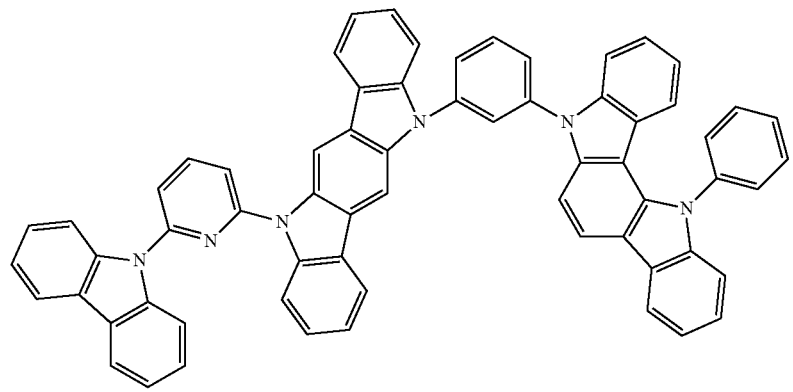
4-19
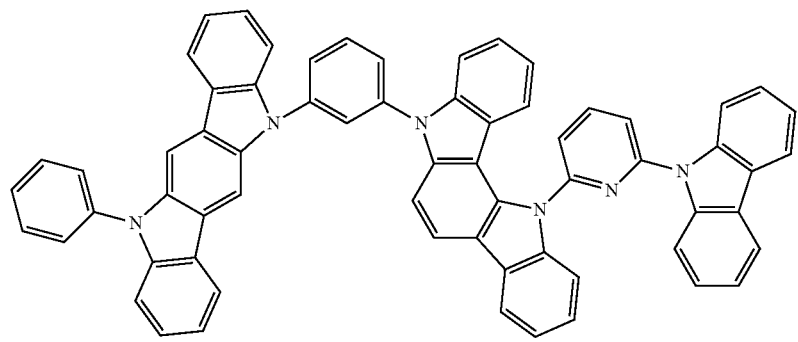
4-20

4-21
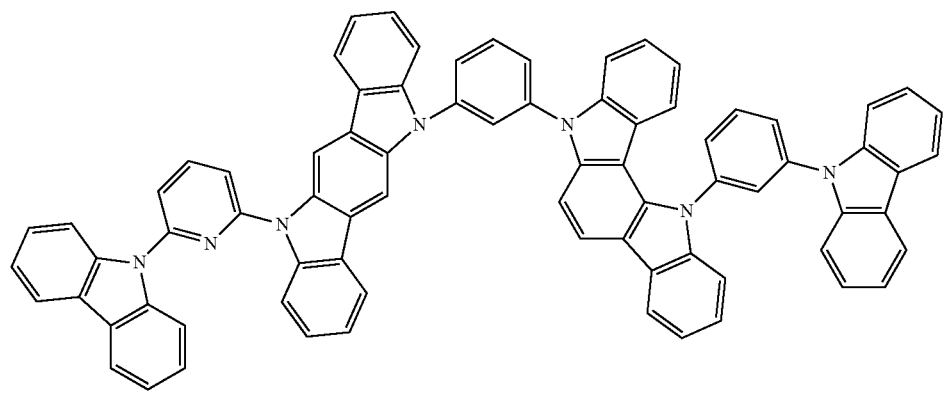
4-22
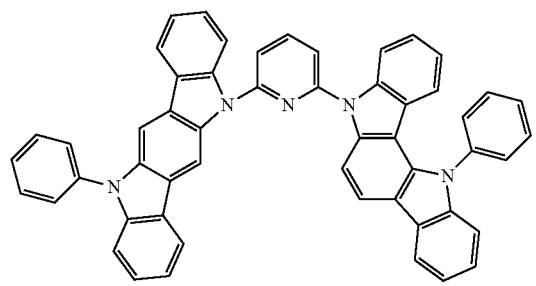
4-23
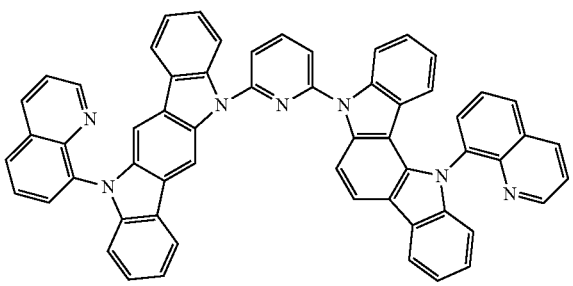
4-24
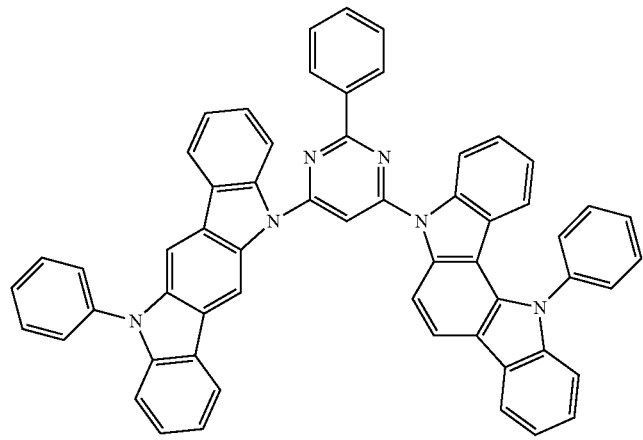
4-25
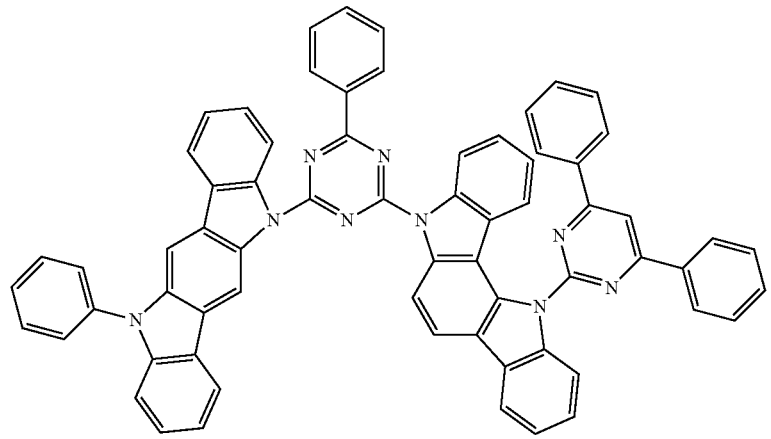

-continued
4-26
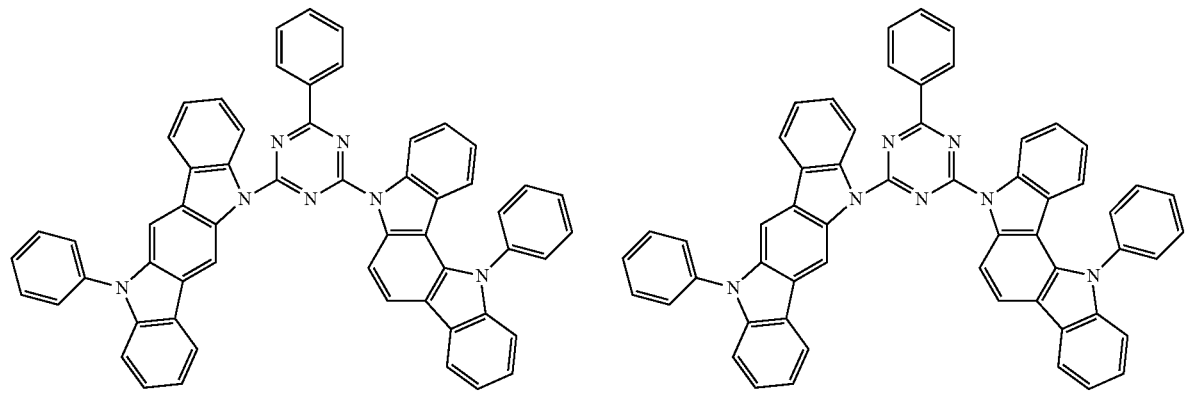
4-27
4-28
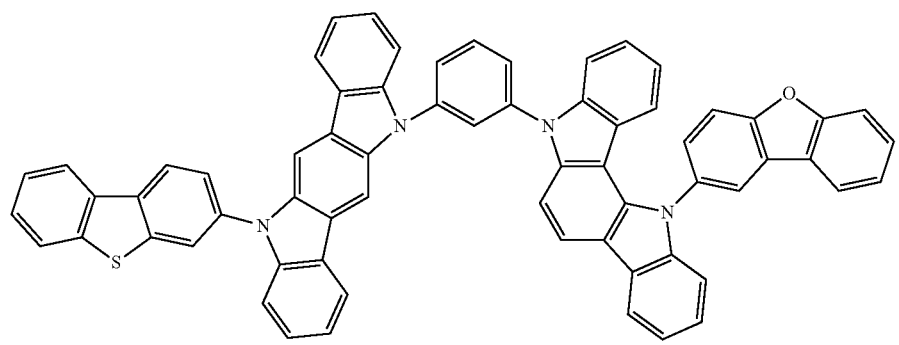
5-1
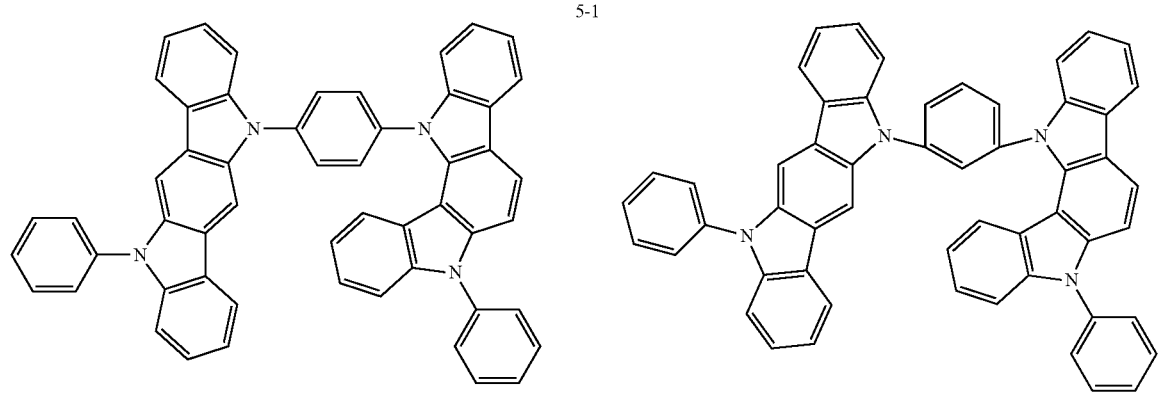
5-2
5-3
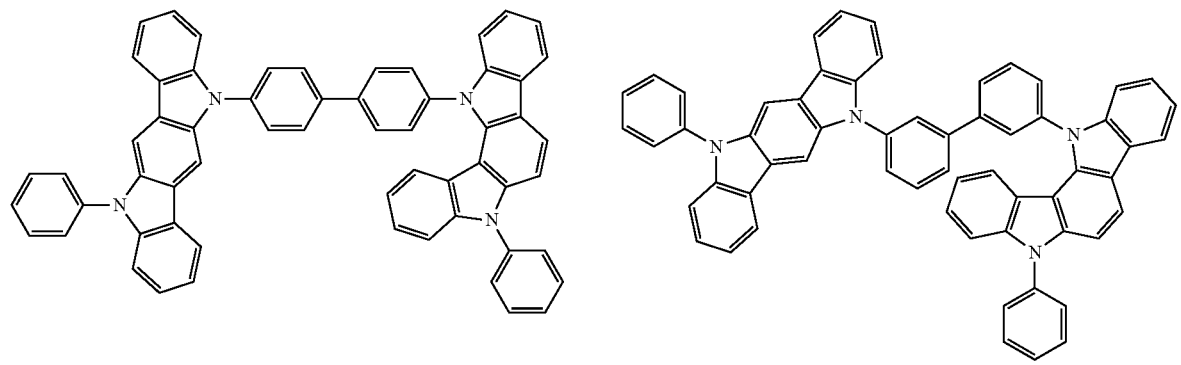
5-4

5-5
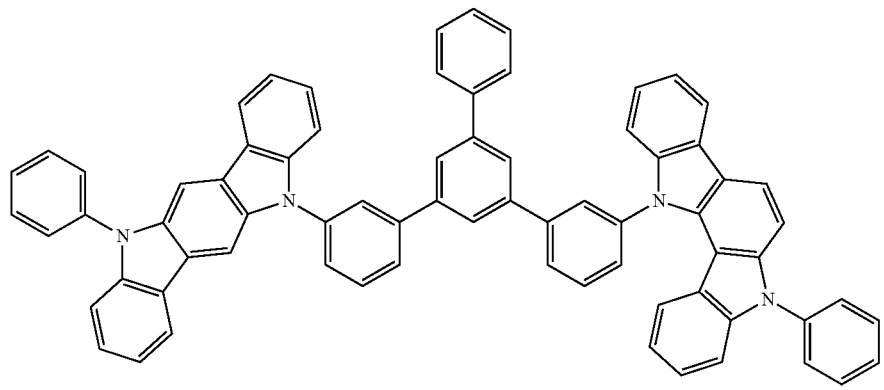
5-6
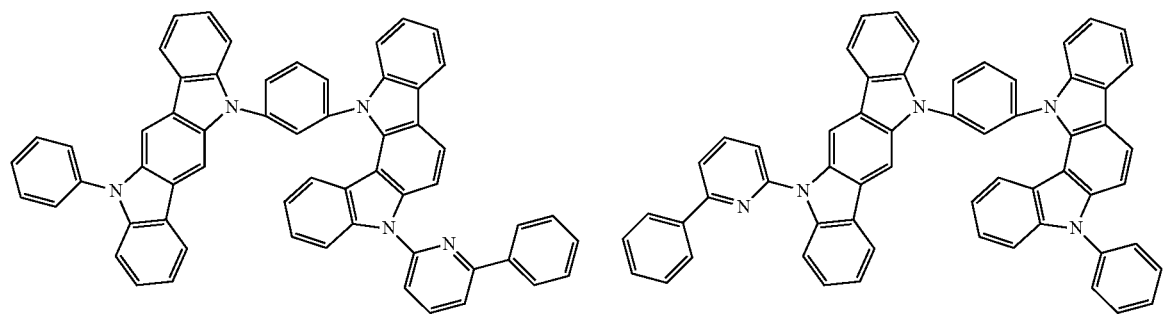
5-7
5-8
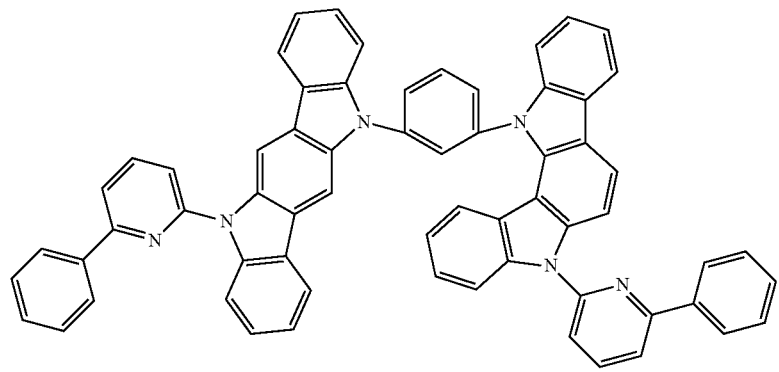
5-9
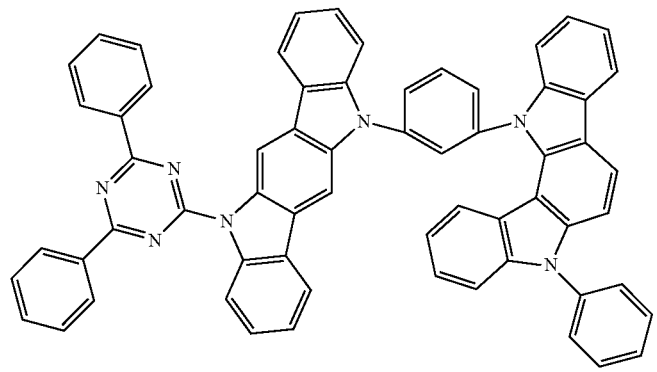

5-10
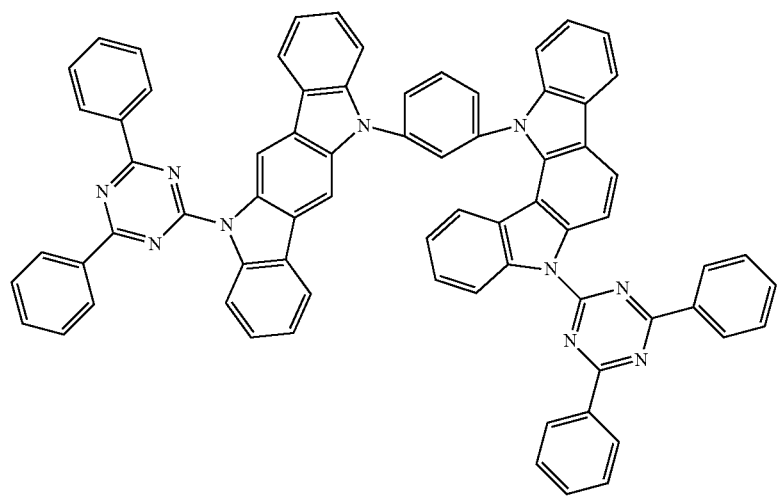
5-11
5-12
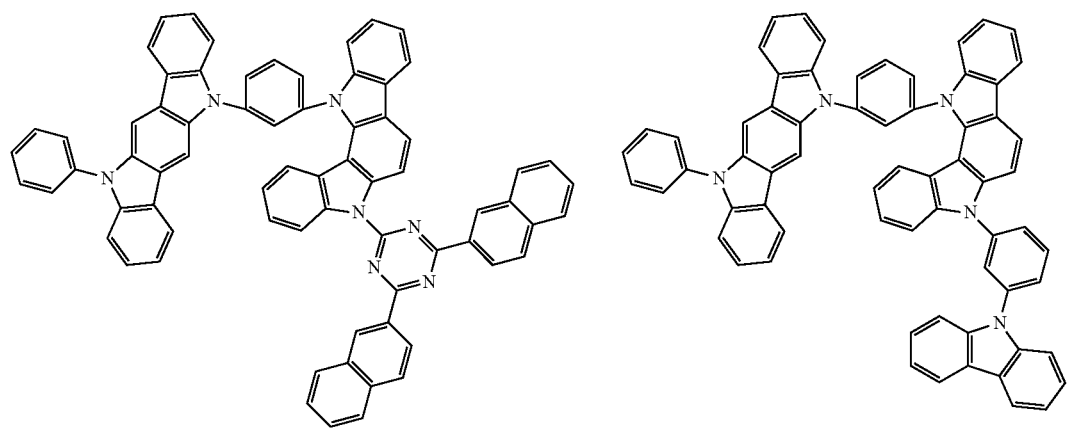
5-13
5-14
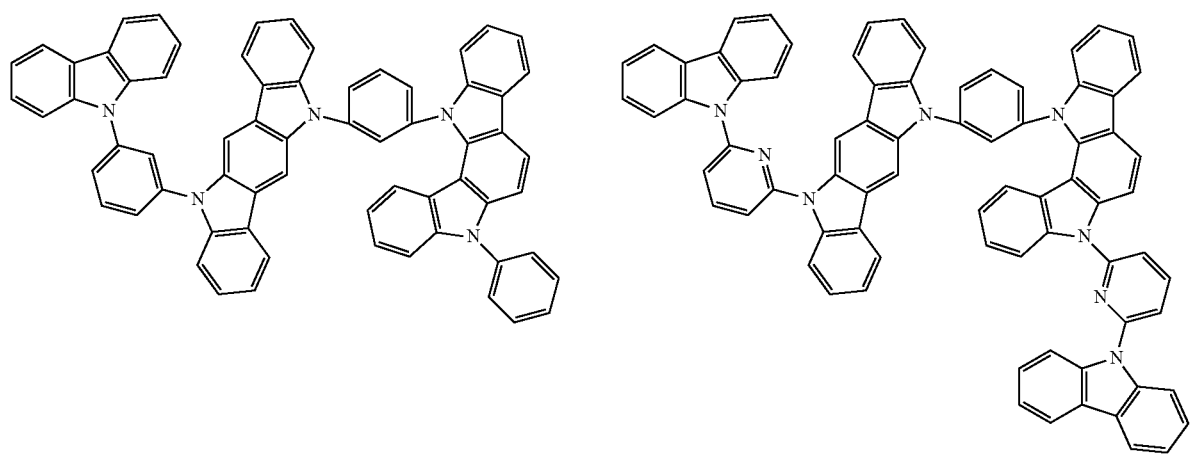

-continued
5-15
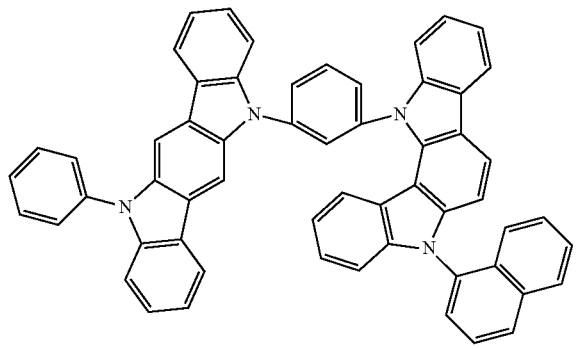
5-16
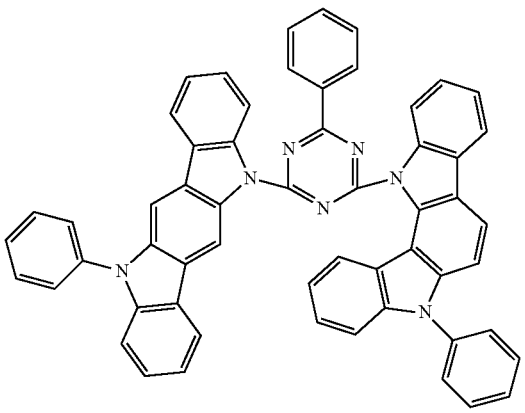
5-17
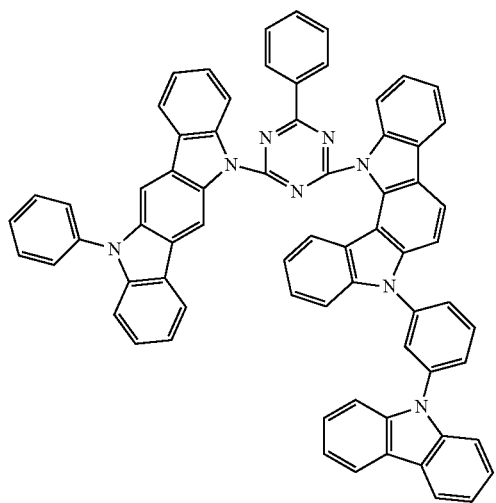
5-18
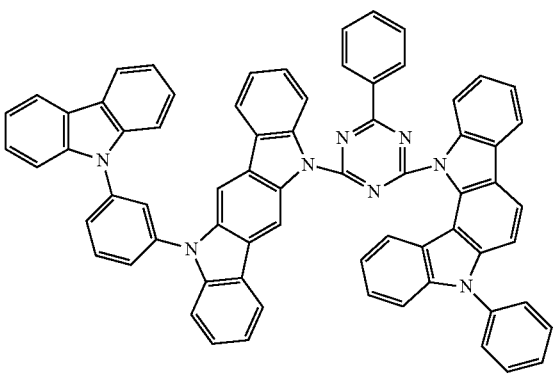
5-19
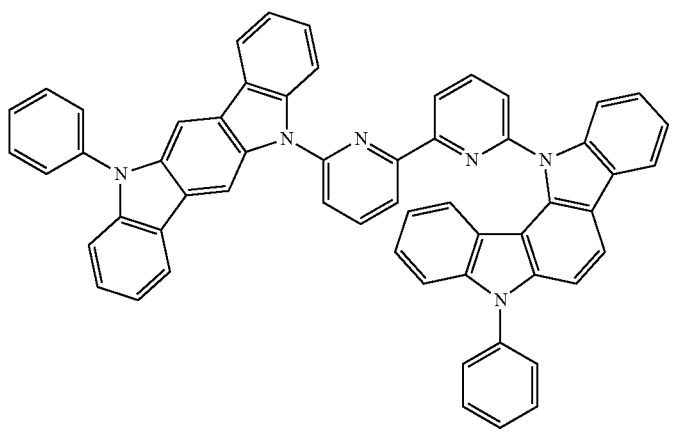

-continued
5-20
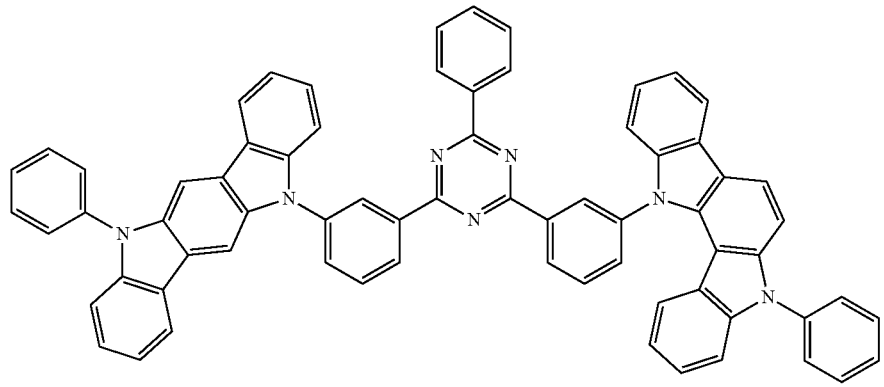
5-21
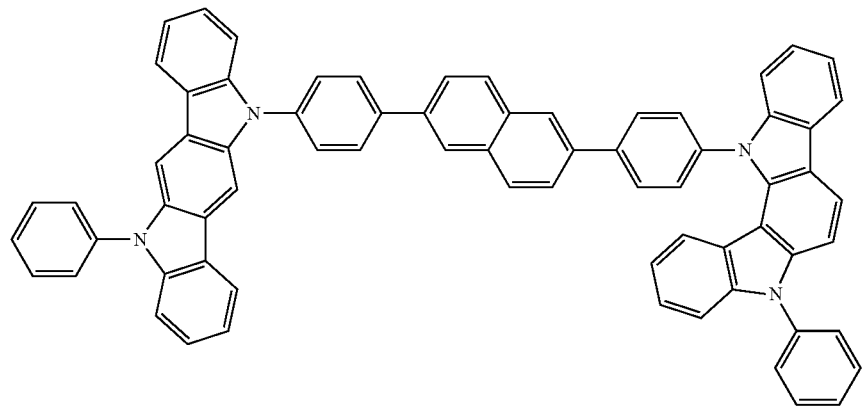
5-22
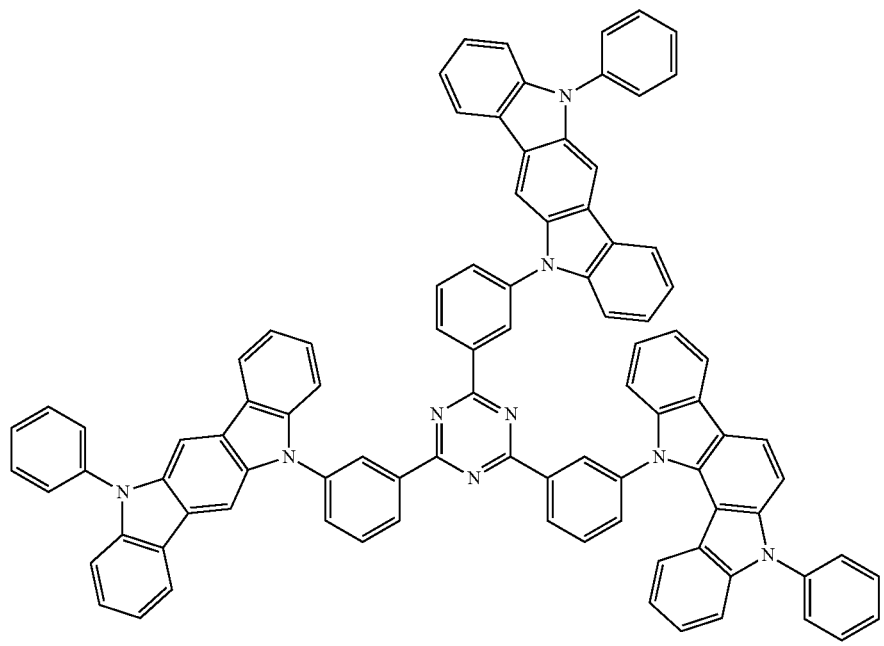

-continued
6-1
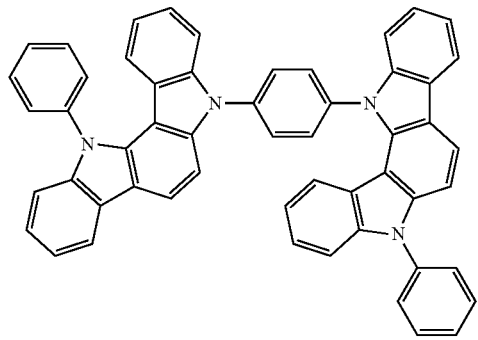
6-2
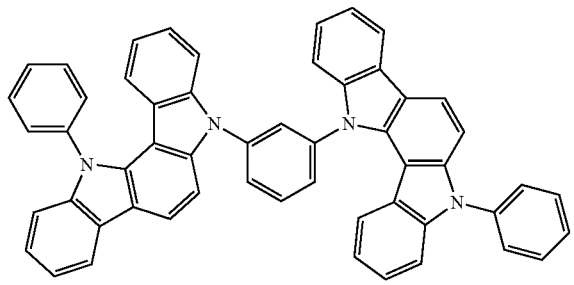
6-3
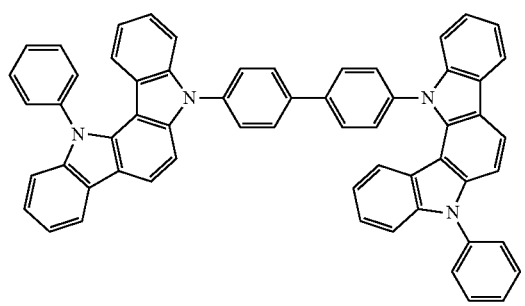
6-4
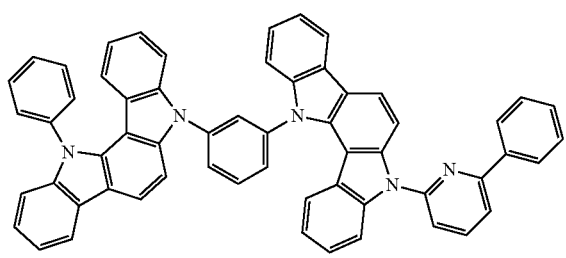
6-5
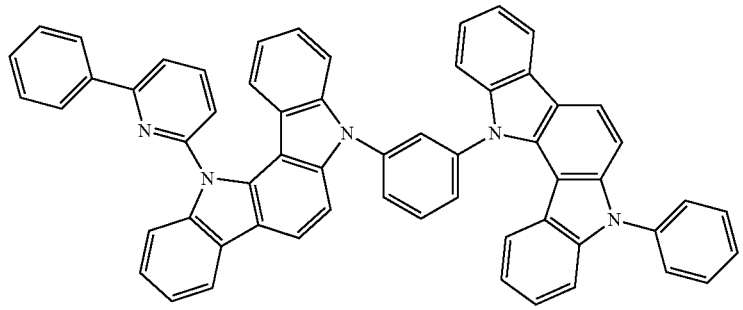
6-6
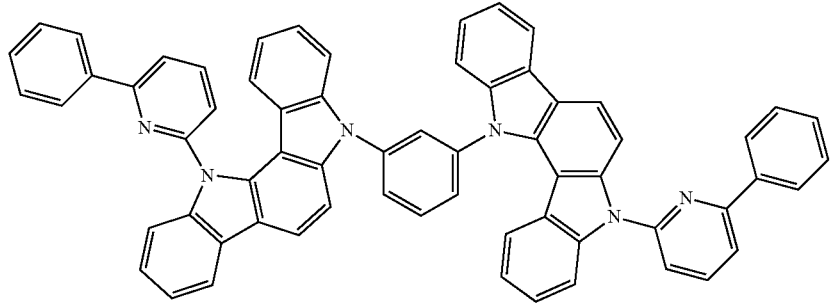
6-7
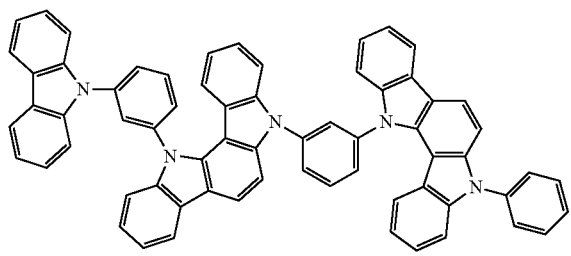
6-8
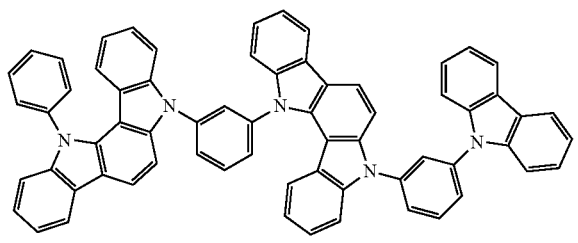

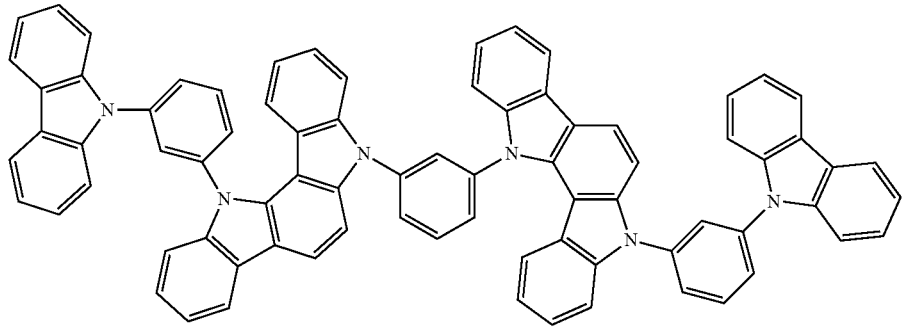
6-9
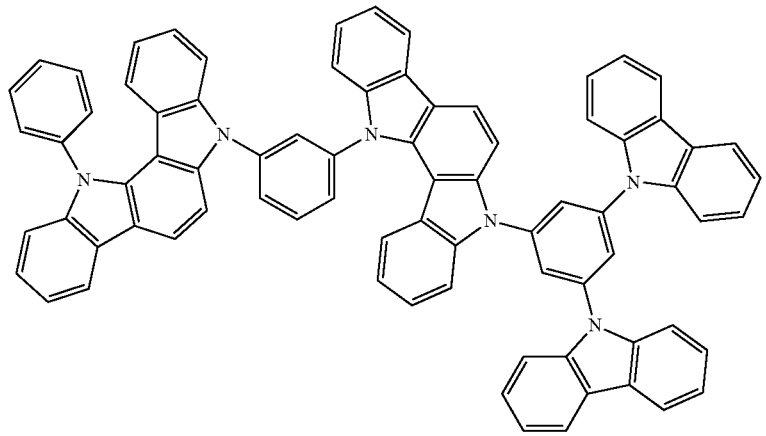
6-10
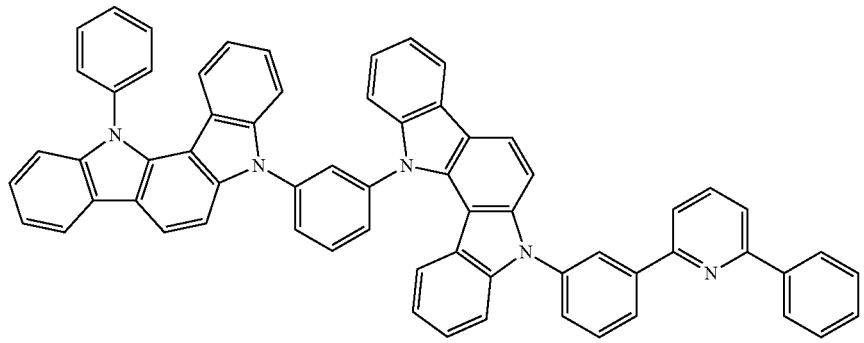
6-11
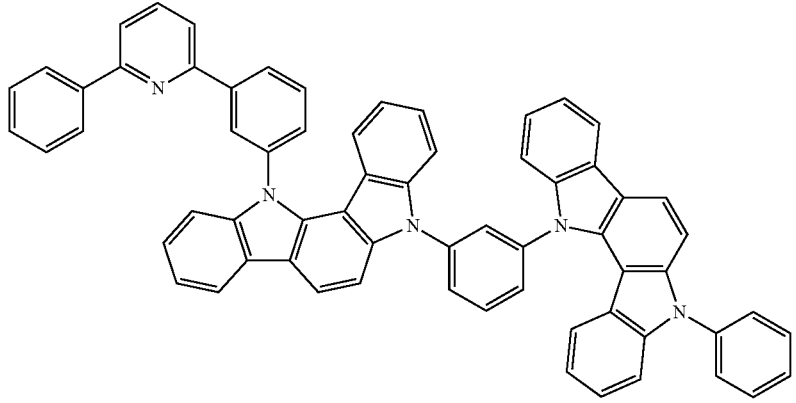
6-12

6-13
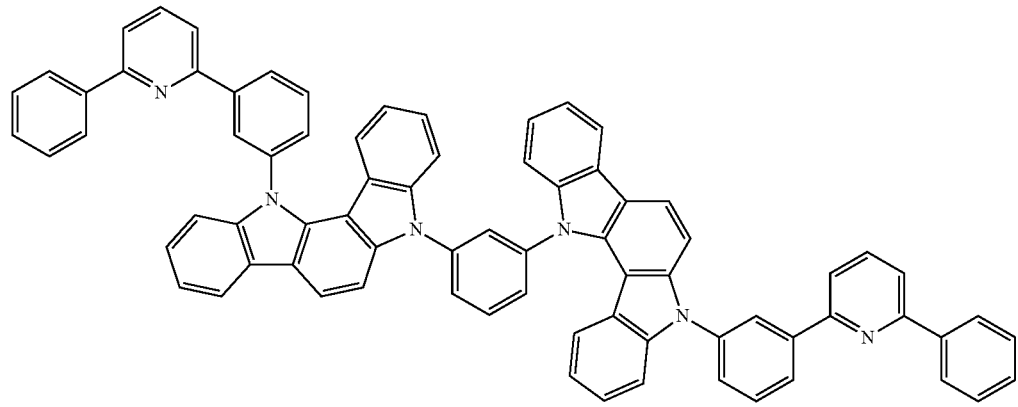
6-14 6-15
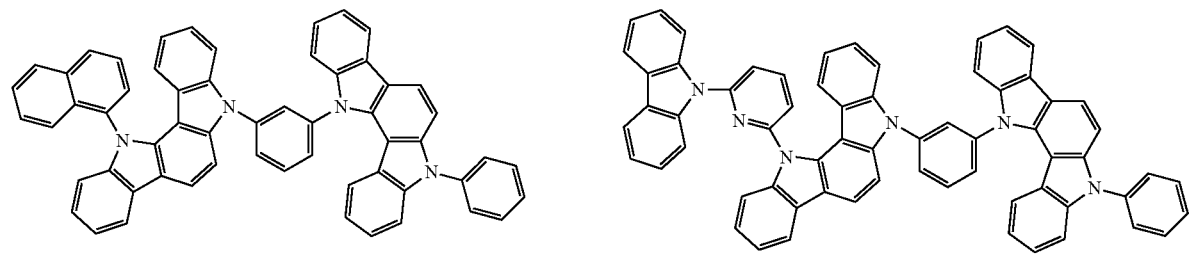
6-16
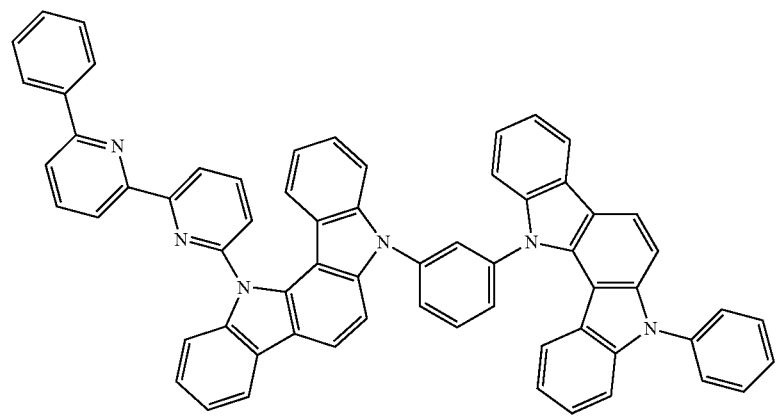
6-17 6-18
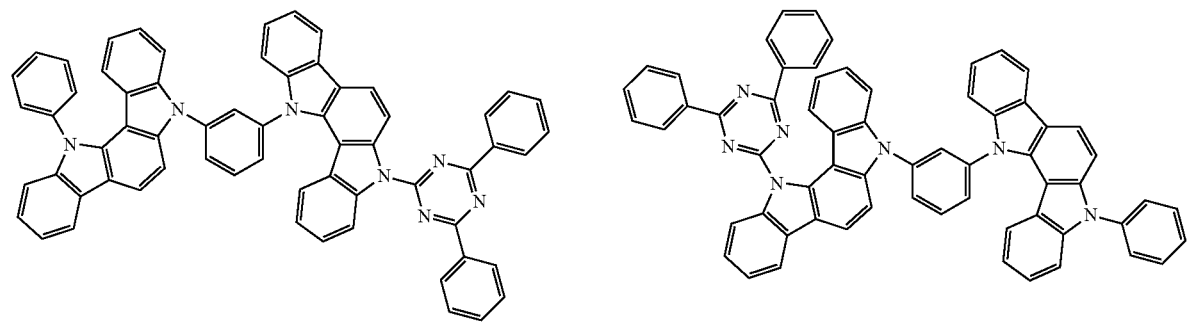

-continued
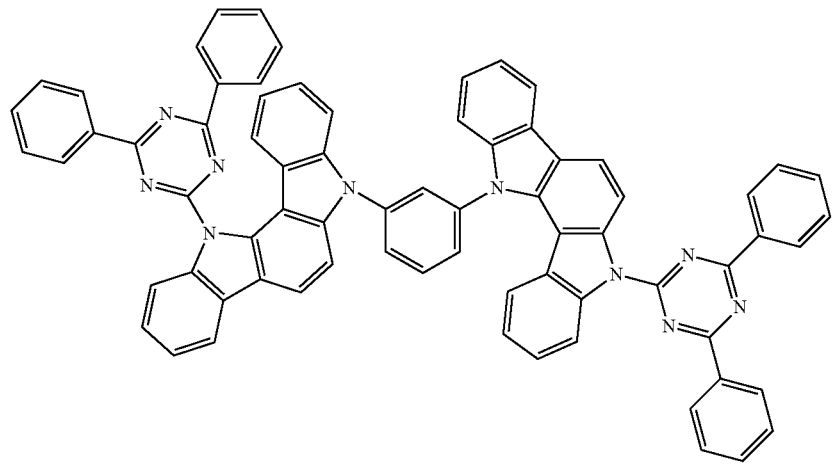
6-19
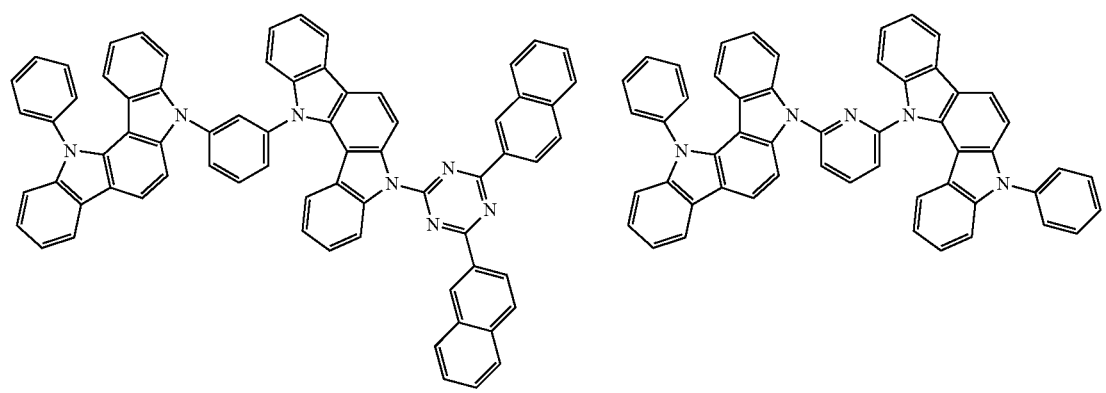
6-20
6-21
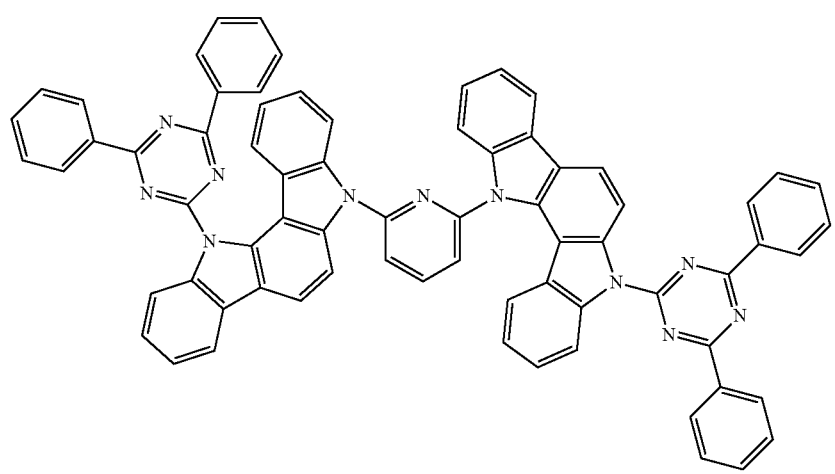
6-22

-continued
6-23
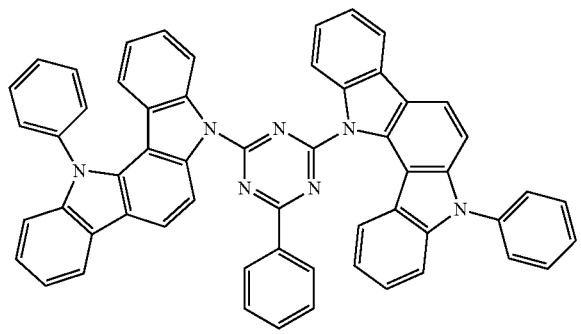
6-24
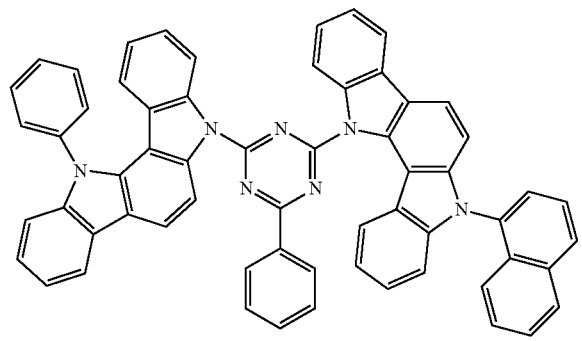
6-25
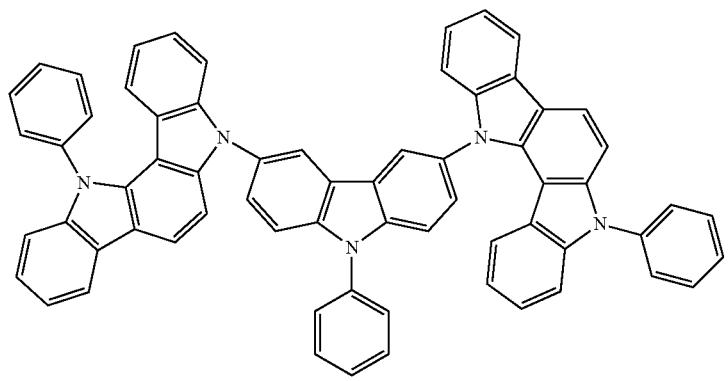
6-26
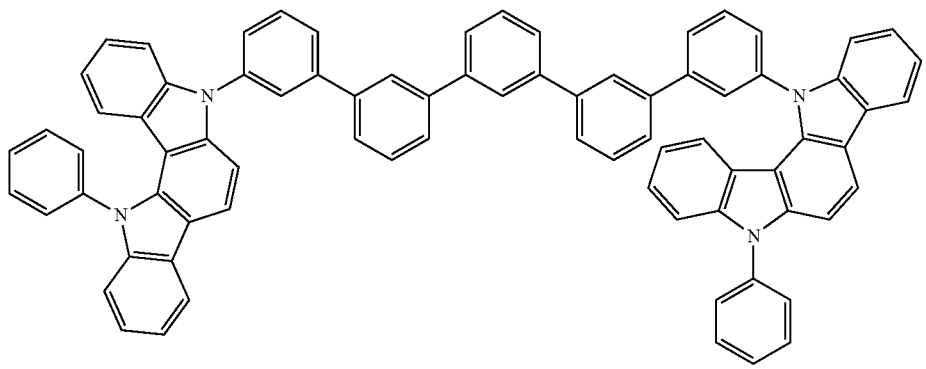
6-27
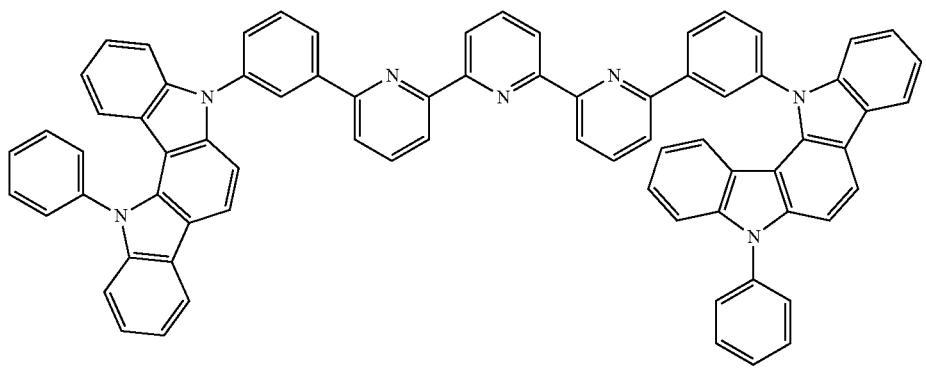

6-28
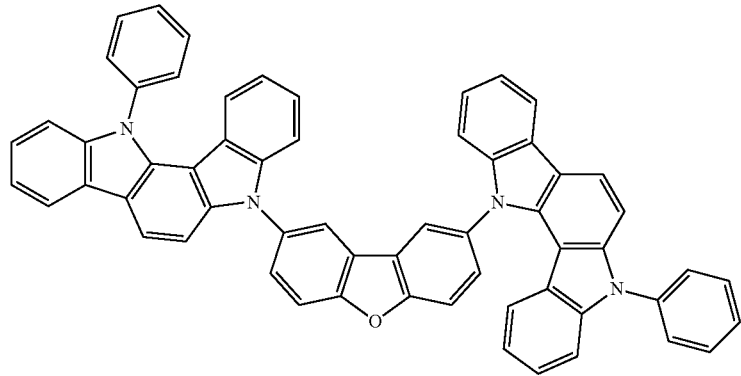
6-29
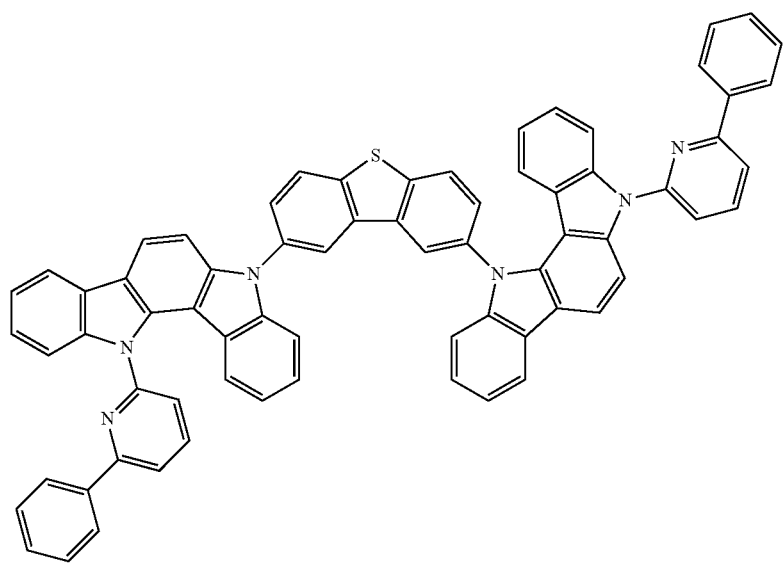
6-30
6-31
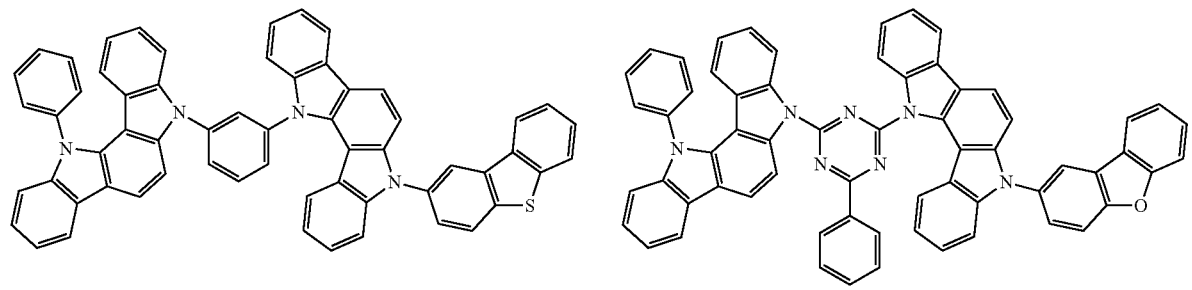

-continued
6-32
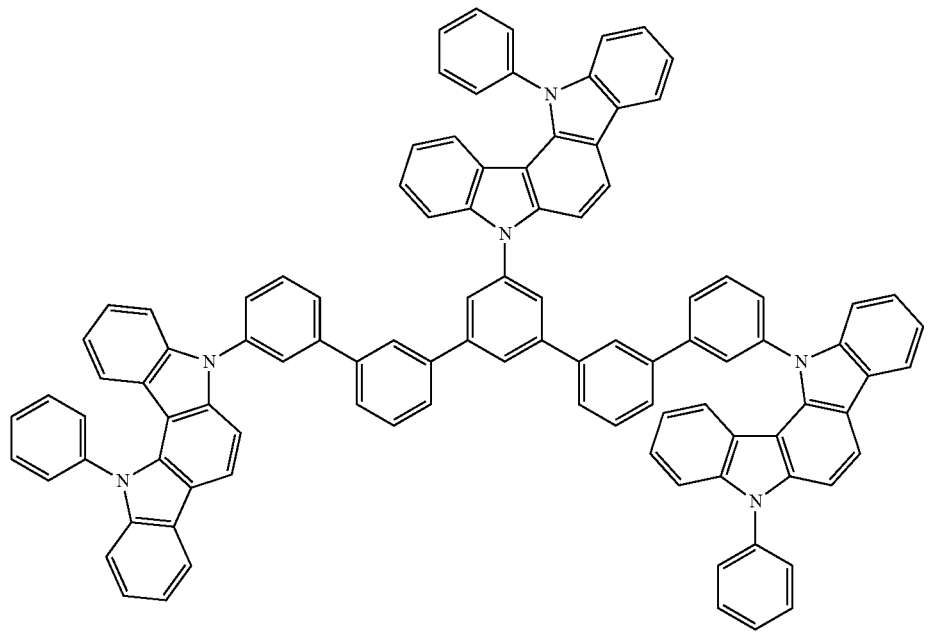
6-33
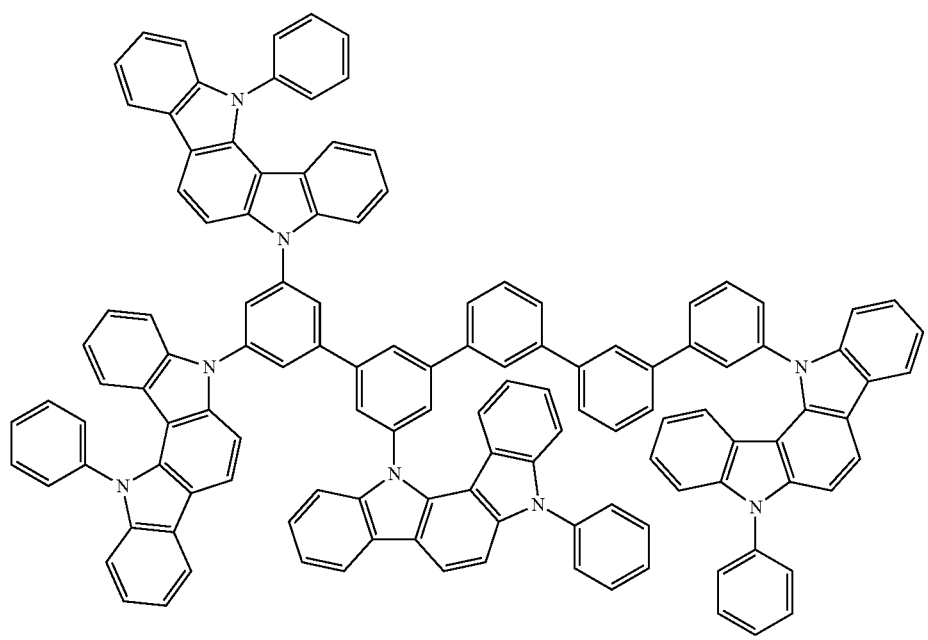
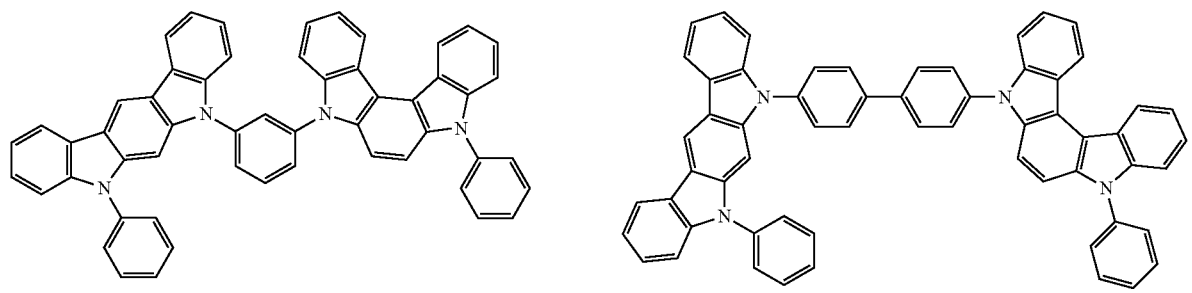
7-1
7-2

7-3
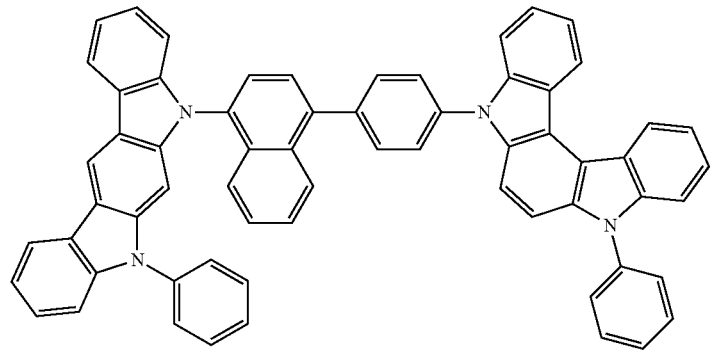
7-4
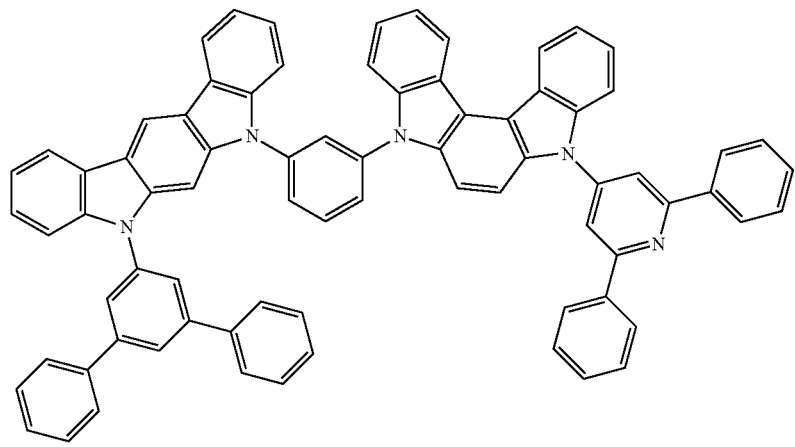
7-5
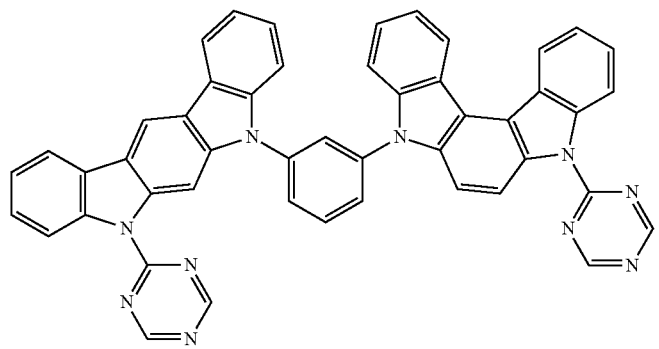
7-6
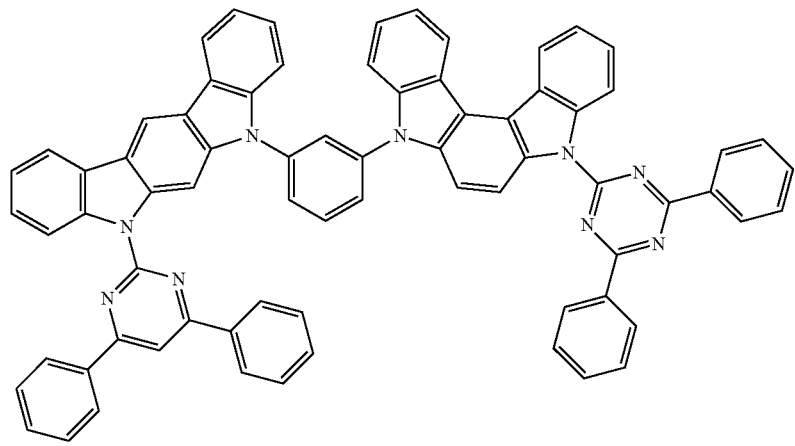

7-7
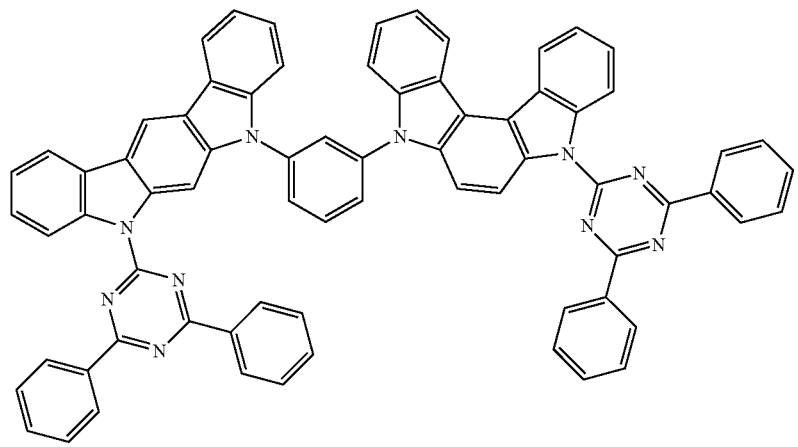
7-8
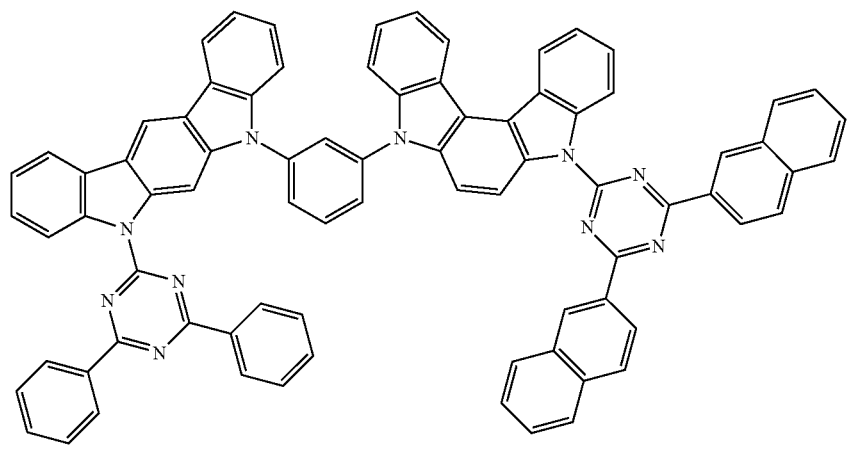
7-9
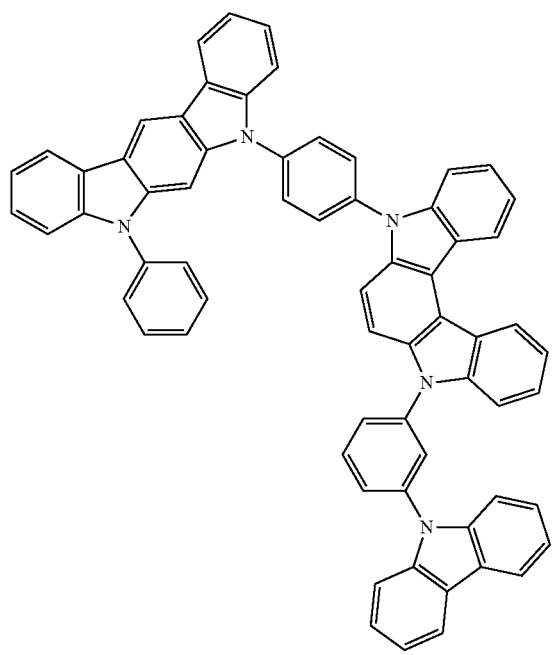

7-10
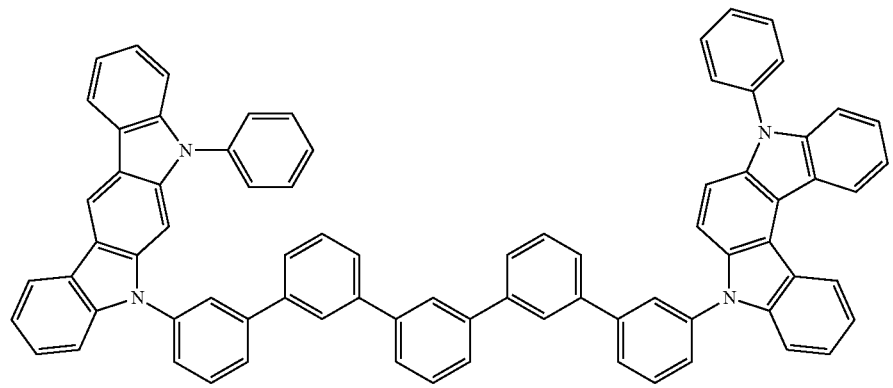
7-11
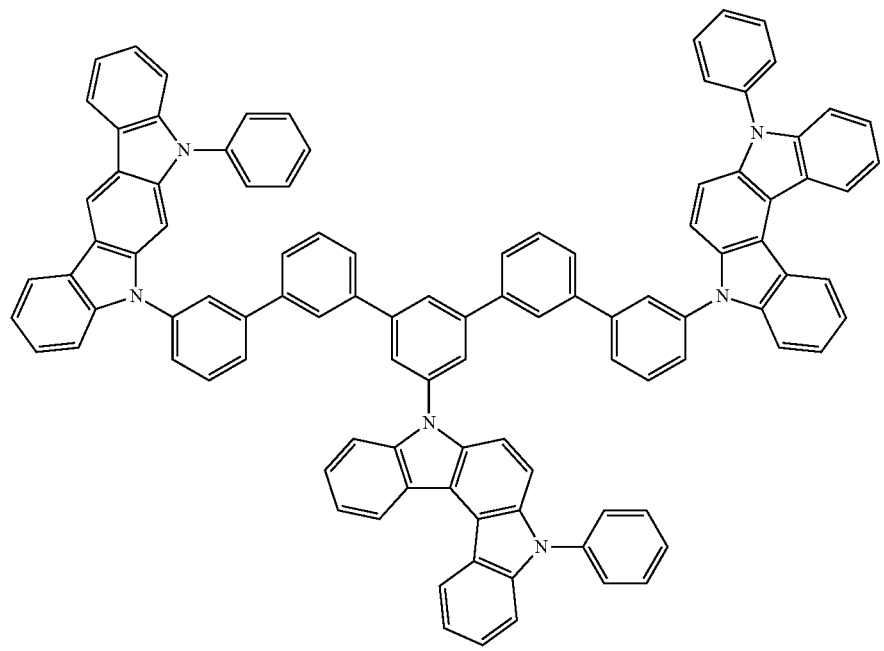
7-12 7-13
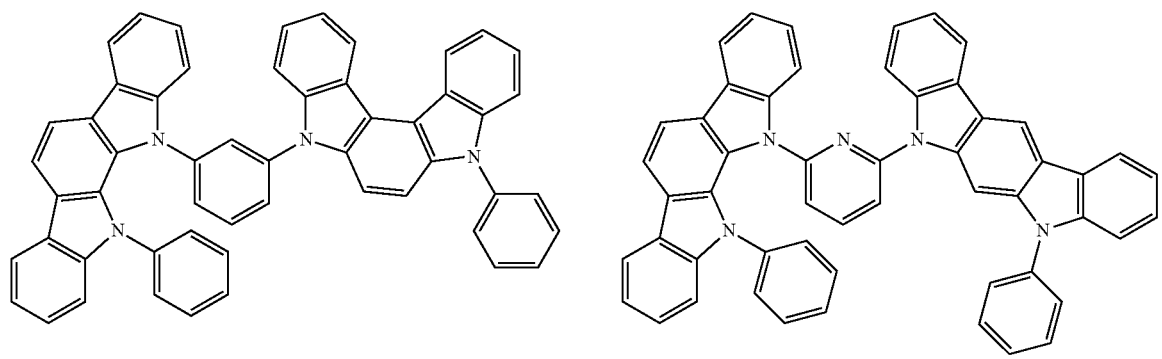

7-14
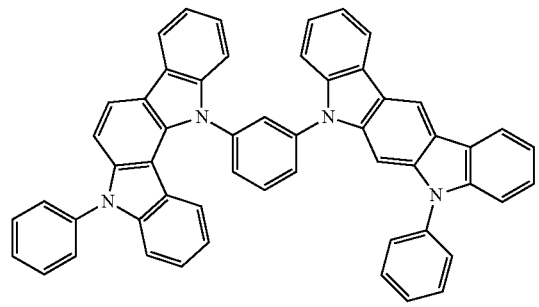
7-15
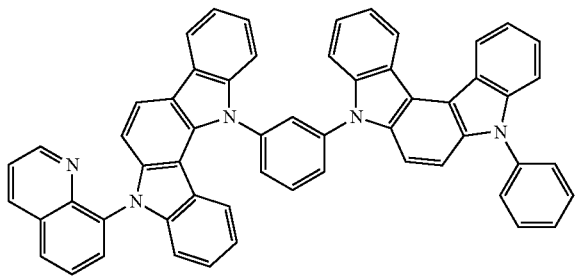
7-16
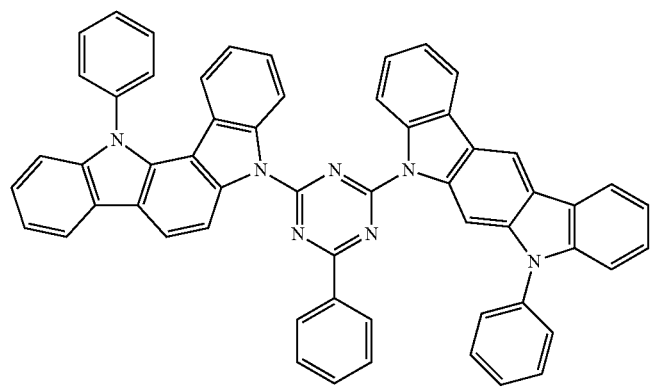
7-17
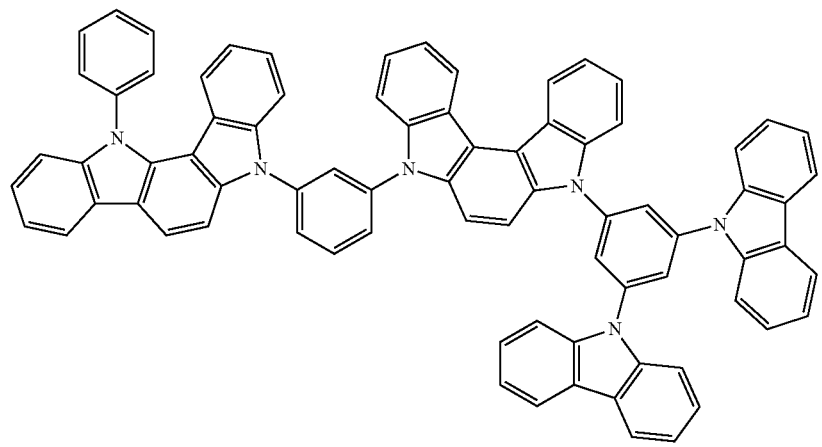
7-18
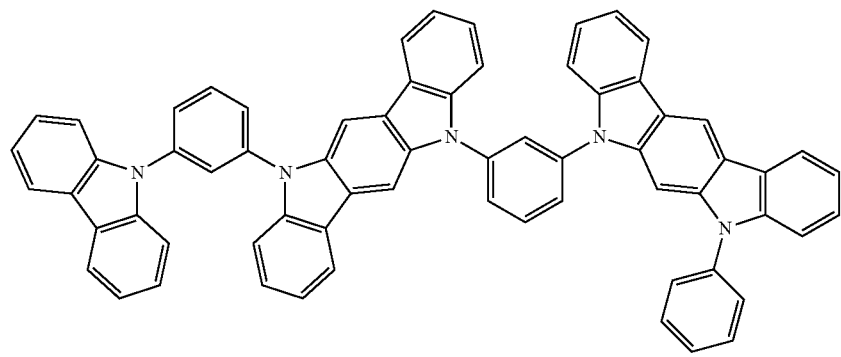

7-19
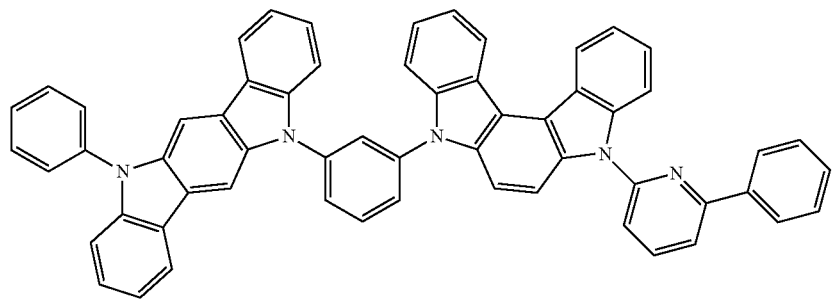
8-1
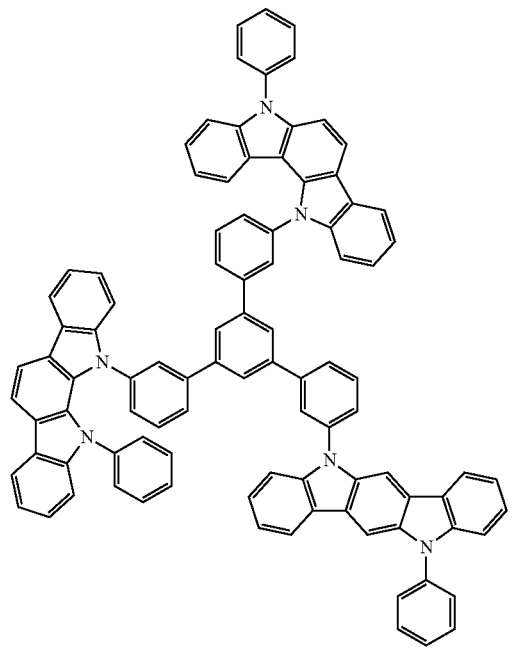
7-17
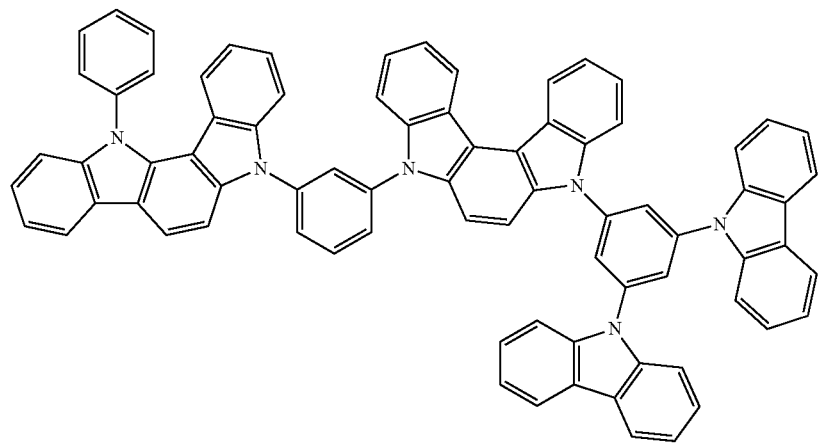

-continued
8-2
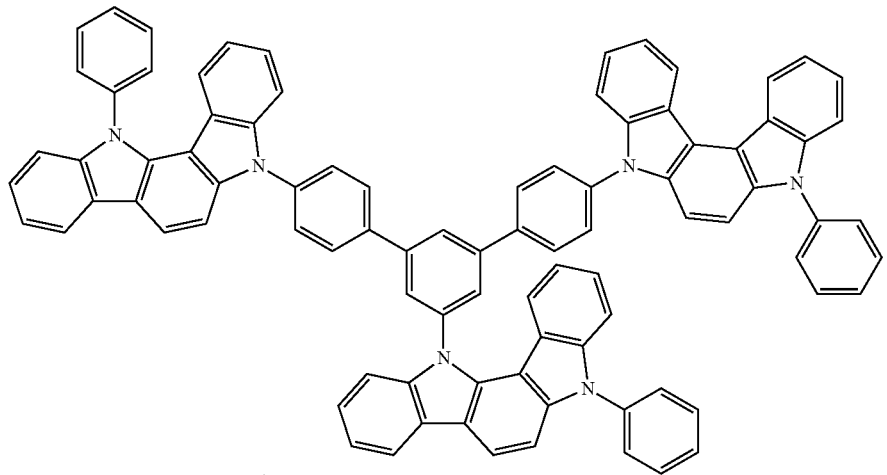
8-3
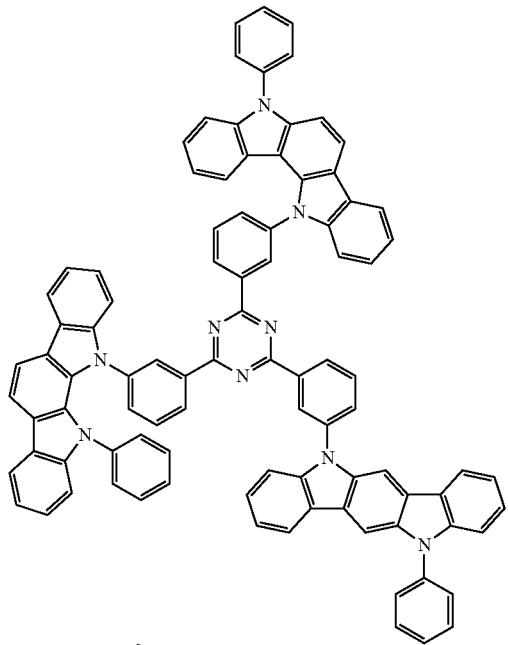
8-4
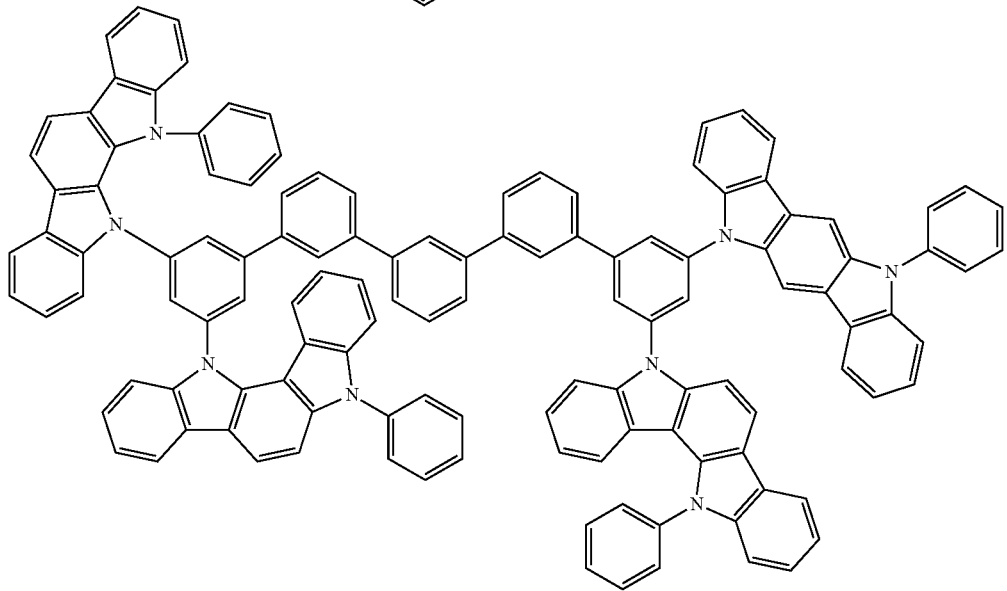

-continued

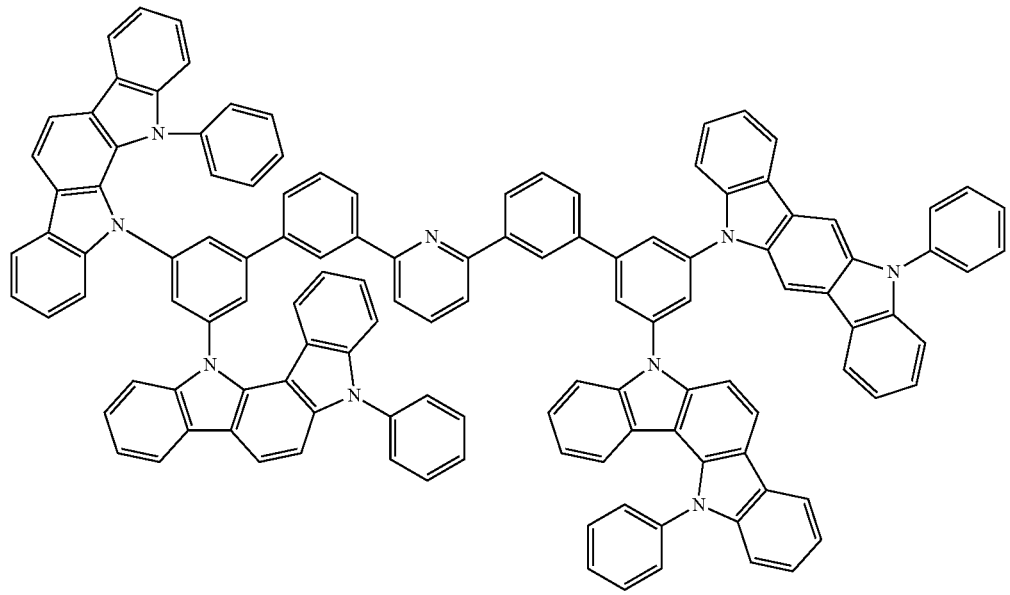

Provided that an organic EL device comprises an anode, a plurality of organic layers, and a cathode piled one upon another on a substrate, incorporation of the indolocarbazole compound represented by the aforementioned general formula (1) in at least one of the organic layers helps to afford an excellent organic EL device. An organic layer suitable for this purpose is a light-emitting layer, a hole-transporting layer, an electron-transporting layer, or a hole-blocking layer. Preferably, the indolocarbazole compound is incorporated as a host material in a light-emitting layer containing a phosphorescent dopant.

The organic EL device of this invention is explained below.

The organic EL device of this invention comprises organic layers between an anode and a cathode piled one upon another on a substrate wherein at least one organic layer is a light-emitting layer and at least one organic layer contains the aforementioned indolocarbazole compound. Advantageously, the light-emitting layer contains a phosphorescent dopant and the aforementioned indolocarbazole compound.

The structure of the organic EL device of this invention is explained below with reference to the drawing, but it is not limited to the one illustrated in the drawing.

FIG. 1 schematically illustrates the cross section of an example of an organic EL device generally used in this invention and the numbers in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The organic EL device of this invention can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is also possible to add or omit a layer or layers according to the need.

Substrate

The organic EL device of this invention is preferably supported by a substrate. There is no specific restriction on the substrate and any of the substrates which have been used customarily in organic EL devices can be used. A substrate made from a material such as glass, transparent plastic, and quartz may be used.

Anode

The anode in an organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CuI, indium tin oxide (ITO), $SnO_2$, and ZnO. Further, a material such as IDIXO ($In_2O_3$—ZnO) which is amorphous and formable into a transparent electrically conductive film may be used. The anode can be formed by preparing a thin film from any of these electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance to be used is an electrically conductive organic compound which is applicable by a coating method, a wet film-forming process such as printing and coating may be employed. When emitted light is taken out from the anode, the transmittance is desirably set at 10% or more and the sheet resistance as the anode is preferably several hundred Ω/□ or less. Further, the thickness of the film is normally selected from the range of 10 to 1,000 nm, preferably 10 to 200 nm, although it varies with the film-forming material.

Cathode

Meanwhile, the cathode is made from an electrode substance having a low work function (4 eV or less) such as a metal, an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation and the like, a mixture of an electron-injecting metal and a second metal which is higher in work function and more stable than the electron-injecting metal is suitable for an electrode substance and examples thereof include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of these electrode substances by a method such as vapor deposition and sputtering. The sheet resistance as the cathode is preferably several hundred Ω/□ or less and the thickness of the film is selected from the range of 10 nm to 5 μm, preferably 50 to 200 nm. Further, an organic EL device wherein either the anode or the cathode is made transparent or translucent in order to transmit emitted light advantageously shows an increase in the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to the fabrication of a device in which both the anode and the cathode display good transmittance properties.

Light-Emitting Layer

The light-emitting layer is a phosphorescent light-emitting layer and contains a phosphorescent dopant and a host material. Preferred as a phosphorescent dopant material is an organic metal complex containing at least one metal selected from ruthenium, rhodium, palladium, silver, rhenium, osmium, iridium, platinum, and gold. The organic metal complexes of this kind are known in the aforementioned prior art technical documents and elsewhere and a suitable organic metal complex may be selected from them and used.

Preferable examples of the phosphorescent dopant include a complex containing a noble metal element such as Ir in the center, typically Ir(ppy)$_3$, a complex such as (Bt)$_2$Iracac, and a complex such as (Btp)Ptacac. Specific examples of these complexes are illustrated below, but the complexes useful for this invention are not limited thereto.

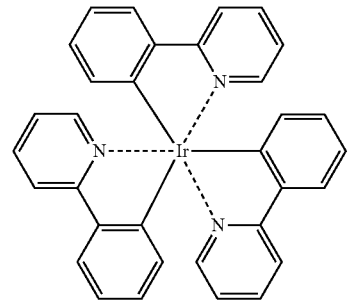

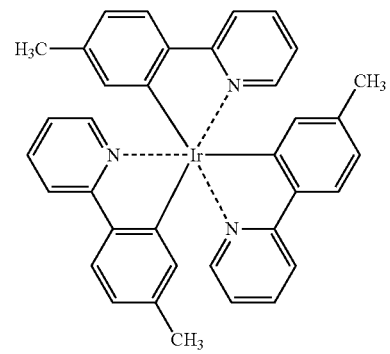

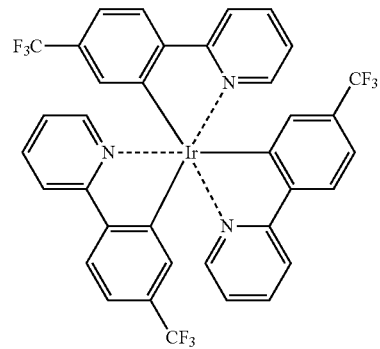

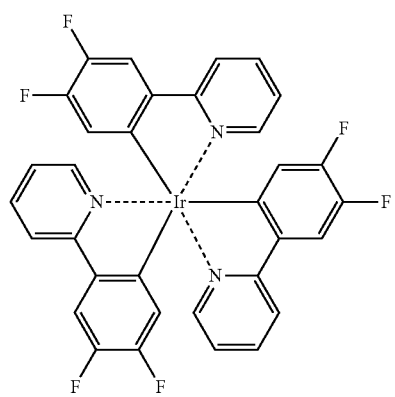

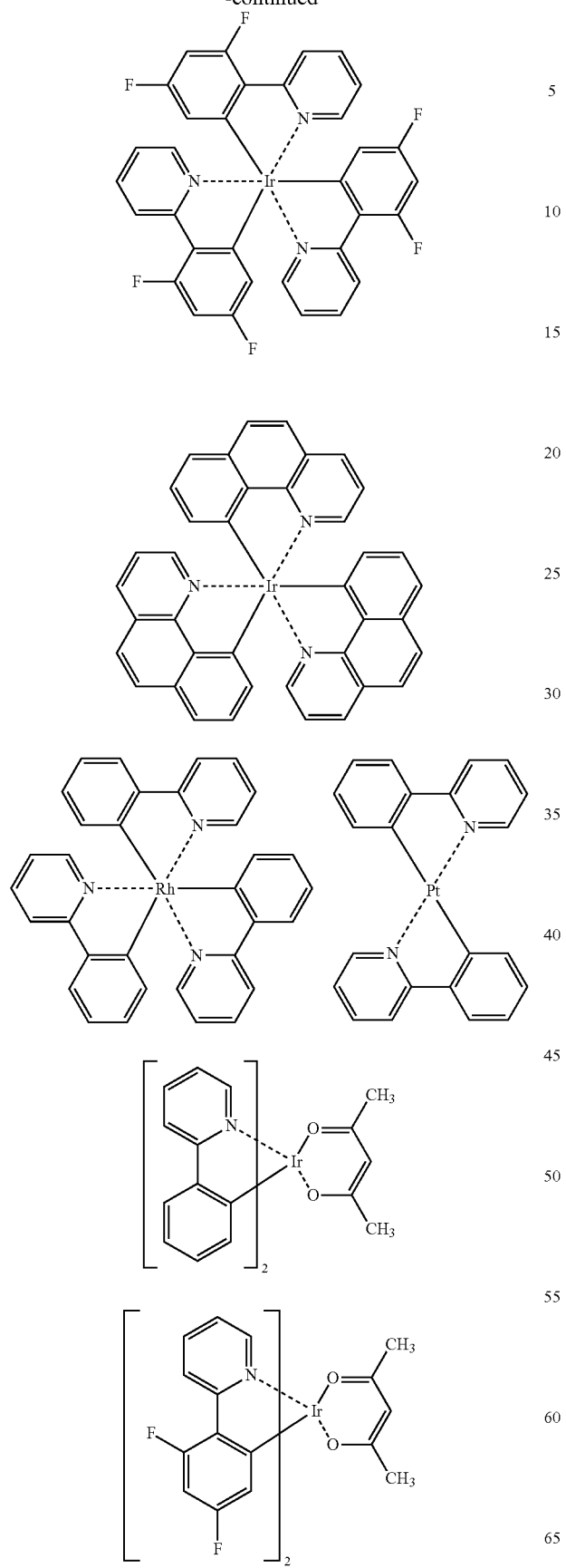
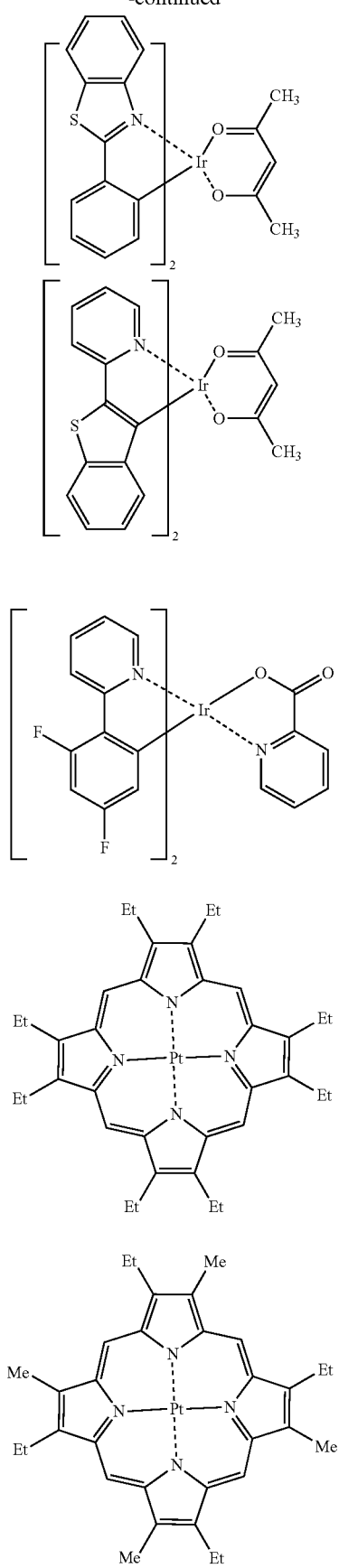

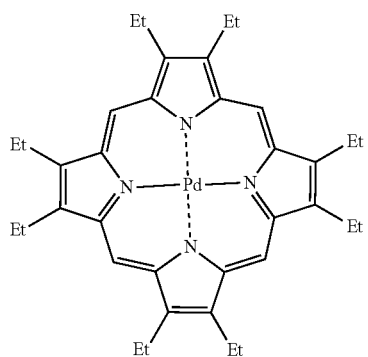

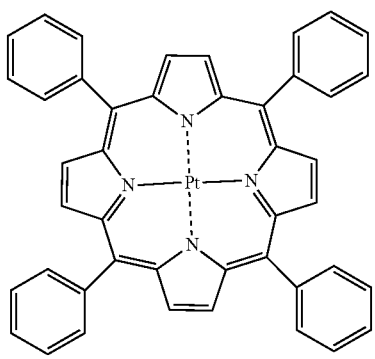

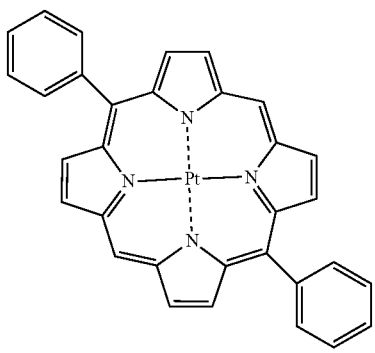

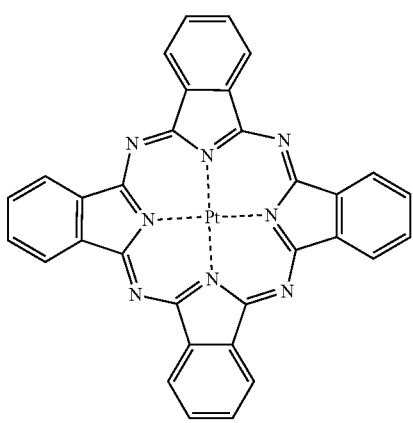

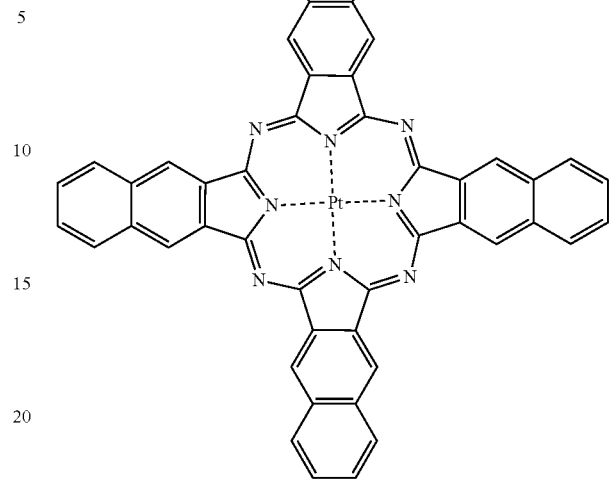

The content of the aforementioned phosphorescent dopant in the light-emitting layer is preferably in the range of 5 to 30 wt %.

It is preferable to use the indolocarbazole compound represented by the aforementioned general formula (1) as a host material in the light-emitting layer. However, in the case where the said indolocarbazole compound is used in any organic layer other than the light-emitting layer, the material to be used in the light-emitting layer may be a host material other than the indolocarbazole compound. The indolocarbazole compound may be used together with other host material. Further, several kinds of known host materials may be used together.

Among the known host compounds, those which are suitable for use preferably have hole-transporting and electron-transporting abilities, can prevent the wavelength of emitted light from shifting to longer wavelengths, and have a high glass transition temperature.

Such known host materials are recorded in a large number of patent documents and elsewhere and a suitable material may be selected from them. Specific examples include, but are not limited to, indole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, dip henylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyp henylenevinylene derivatives, and polyfluorene derivatives.

Injecting Layer

The injecting layer is a layer which is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need.

Hole-Blocking Layer

The hole-blocking layer has a function of the electron-transporting layer in a broad sense and is composed of a hole-blocking material which has an extremely poor ability to transport holes while having a function of transporting electrons. The hole-blocking layer can improve the probability of recombination of electrons and holes by transporting electrons while blocking holes.

It is preferable to use the indolocarbazole compound represented by general formula (1) in the hole-blocking layer. However, in the case where the indolocarbazole compound is used in any organic layer other than the hole-blocking layer, a known hole-blocking material layer may be used instead. Further, one of the materials for the hole-transporting layer to be described later on may be used here as a hole-blocking material according to the need.

Electron-Blocking Layer

The electron-blocking layer is composed of a material which has an extremely poor ability to transport electrons while having a function of transporting holes and can improve the probability of recombination of electrons and holes by transporting holes while blocking electrons.

The indolocarbazole compound represented by general formula (1) of this invention may be used as a material for the electron-blocking layer. Alternatively, one of the materials for the hole-transporting layer to be described later on may be used here according to the need. The thickness of the electron-blocking layer is preferably 3 to 100 nm, more preferably 5 to 30 nm.

Exciton-Blocking Layer

The exciton-blocking layer is a layer for blocking excitons that are generated by the recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and cathode sides.

The indolocarbazole compound represented by general formula (1) may be used as a material for the exciton-blocking layer. Other materials may also be used and examples thereof include 1,3-dicarbazolylbenzene (mCP) and bis(2-methyl-8-quinolinolato)-4-phenylphenolatoaluminum (III) (BAlq).

Hole-Transporting Layer

The hole-transporting layer is made from a hole-transporting material which has a function of transporting holes and it may be provided in a single layer or a plurality of layers.

The hole-transporting layer has either a property of injecting or transporting holes or a property of constituting a barrier to electrons and it may be an organic material or an inorganic material. It is preferable to use the indolocarbazole compound represented by general formula (1) in the hole-transporting layer. However, a suitable selection may be made from the known compounds. Examples of known compounds suitable for use as hole-transporting materials include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Preferable examples include porphyrin compounds, aromatic tertiary amine compounds, and styrylamine compounds and more preferable examples include aromatic tertiary amine compounds.

Electron-Transporting Layer

The electron-transporting layer is formed from a material which has a function of transporting electrons and may be provided in a single layer or a plurality of layers.

An electron-transporting material (serving also as a hole-blocking material in some cases) may be an arbitrary material so long as it has a function of transporting electrons that are injected from the cathode to the light-emitting layer. It is preferable to use the material represented by general formula (1) of this invention in the electron-transporting layer. However, a suitable selection may be made from the known compounds. Examples of such known compounds include nitro-substituted fluorene derivatives, diphenylquinone derivatives, thiopyran dioxide derivatives, carbodimides, fluorenylidenemethane derivatives, anthraquinodimethan derivatives, anthrone derivatives, and oxadiazole derivatives. Further, thiadiazole derivatives which are derived from the aforementioned oxadiazole derivatives by substituting a sulfur atom for the oxygen atom of the oxadiazole ring and quinoxaline derivatives having a quinoxaline ring which is known as an electron-withdrawing group may be used as electron-transporting materials. Further, polymer materials which contain any of these materials in the polymer chain or polymer materials whose backbone is constituted of any of these materials may be used.

EXAMPLES

This invention is explained in more detail hereinafter with reference to the examples. However, this invention is not limited to the examples and can be reduced to practice in various modes unless such a practice exceeds the gist of this invention.

The indolocarbazole compounds were synthesized according to the routes shown below. The compound numbers correspond to the numbers assigned to the aforementioned chemical formulas.

Synthetic Example 1

Synthesis of Compound 3-15

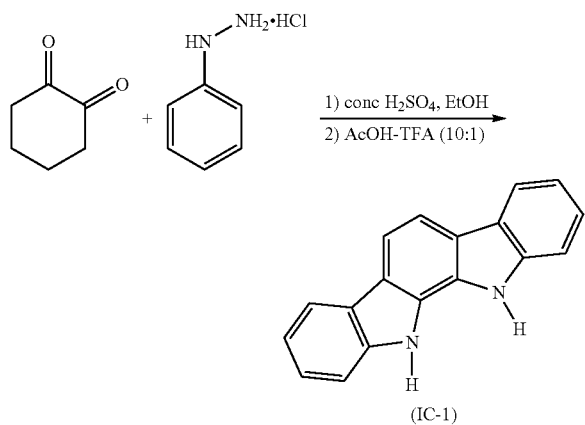

(IC-1)

Under a nitrogen atmosphere, 33.3 g (0.30 mol) of 1,2-cyclohexanedione, 86.0 g (0.60 mol) of phenylhydrazine hydrochloride, and 1,000 ml of ethanol were stirred at room temperature, 3.0 g (0.031 mol) of concentrated sulfuric acid was added dropwise over 5 minutes with stirring, and then the resulting solution was heated at 65° C. with stirring for 4 hours. The reaction solution was cooled to room temperature and the precipitated crystal was collected by filtration and washed with ethanol (2×500 ml) to give 80.0 g of a purplish brown crystal. This crystal, weighing 72.0 g (0.26 mol), was heated with 72.0 g of trifluoroacetic acid and 720.0 g of acetic acid at 100° C. with stirring for 15 hours. The reaction solution was cooled to room temperature and the precipitated crystal was collected by filtration, washed with acetic acid (200 ml), and purified by reslurrying to give 30.0 g (45% yield) of 5,12-dihydroindolo[2,3-a]carbazole (Compound IC-1) as a white crystal.

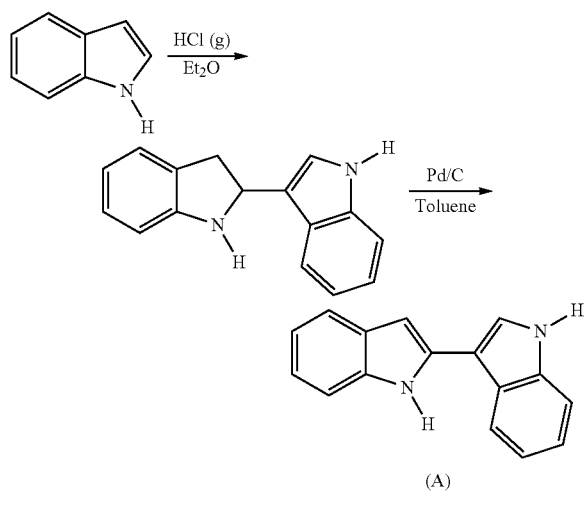

(A)

Under a nitrogen atmosphere, a hydrogen chloride gas generated by adding dropwise 112.0 g (1.10 mol) of concentrated hydrochloric acid to 211.7 g (2.16 mol) of concentrated sulfuric acid over 1 hour was blown into a solution of 20.0 g (0.17 mol) of indole in 300 ml of dehydrated diethyl ether with stirring at room temperature. The reaction solution was stirred at room temperature for 15 hours and, thereafter, 121.0 g of ethyl acetate and 303.2 g of a saturated aqueous sodium hydrogen carbonate solution were added. The aqueous layer was extracted with ethyl acetate (2×100 ml) and then the organic layer was washed with a saturated aqueous sodium hydrogen carbonate solution (100 ml) and distilled water (2×100 ml). The organic layer was dried over anhydrous magnesium sulfate, the magnesium sulfate was separated by filtration, and the solvent was distilled off under reduced pressure. The residue was dissolved in 150 ml of toluene, 2.5 g of palladium/activated carbon was added, and the mixture was heated under reflux at 111° C. with stirring for 3 hours. The reaction solution was cooled to room temperature, the palladium/activated carbon was separated by filtration, and the solvent was distilled off under reduced pressure. The residue was purified by recrystallization to give 14.7 g (37% yield) of Intermediate A as a white crystal.

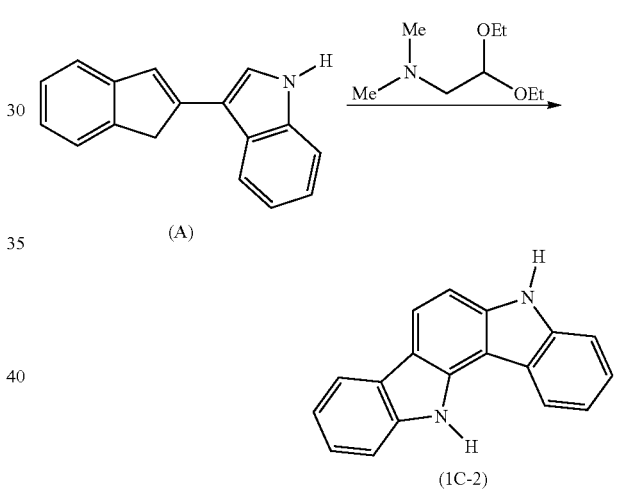

(A)

(IC-2)

Under a nitrogen atmosphere, 14.1 g (0.061 mol) of Intermediate A, 11.4 g (0.071 mol) of N,N-dimethylaminoacetaldehyde diethyl acetal, and 110.0 g of acetic acid were heated under reflux at 118° C. with stirring for 8 hours. The reaction solution was cooled to room temperature and the precipitated crystal was collected by filtration and washed with acetic acid (30 ml). The crystal thus obtained was purified by reslurrying to give 10.4 g (67% yield) of 5,12-dihydroindolo[3,2-a]carbazole (Compound IC-2) as a white crystal.

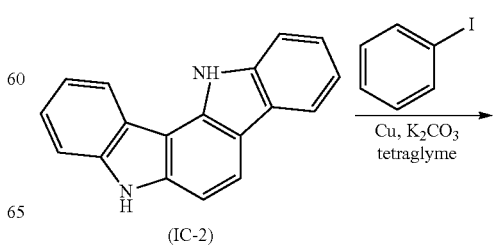

(IC-2)

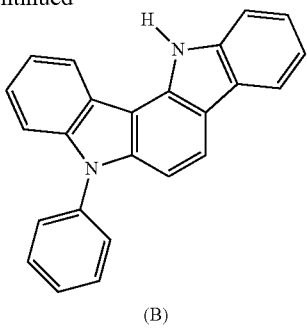

(B)

Under a nitrogen atmosphere, 10.0 g (0.039 mol) of Compound IC-2, 39.8 g (0.20 mol) of iodobenzene, 6.2 g (0.098 mol) of copper, 8.1 g (0.059 mol) of potassium carbonate, and 200 ml of tetraglyme were stirred, then heated to 190° C., and stirred at this temperature for 24 hours. The reaction solution was cooled to room temperature and the copper and an inorganic matter were separated by filtration. To the filtrate was added 200 ml of distilled water, the mixture was stirred, and the precipitated crystal was collected by filtration. The crystal was dried under reduced pressure and purified by column chromatography to give 9.7 g (0.029 mol, 75% yield) of Intermediate B as a white powder.

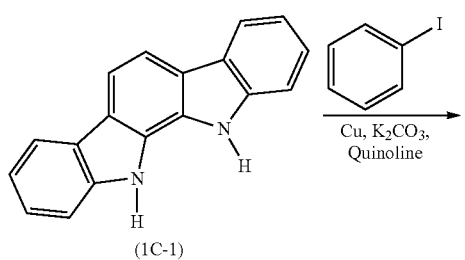

(1C-1)

Under a nitrogen atmosphere, 26.0 g (0.10 mol) of Compound IC-1, 122.7 g (0.60 mol) of iodobenzene, 54.7 g (0.29 mol) of copper iodide, 66.7 g (0.48 mol) of potassium carbonate, and 800 ml of quinoline were heated at 190° C. with stirring for 72 hours. The reaction solution was cooled to room temperature and distilled water (500 ml) and dichloromethane (500 ml) were added with stirring. The precipitated crystal was collected by filtration and the organic layer was washed with distilled water (3×500 ml). The organic layer was dried over anhydrous magnesium sulfate, the magnesium sulfate was separated by filtration, and the solvent was distilled off under reduced pressure. The residue was purified by silica gel column chromatography to give 13.7 g (41% yield) of Intermediate C as a white solid.

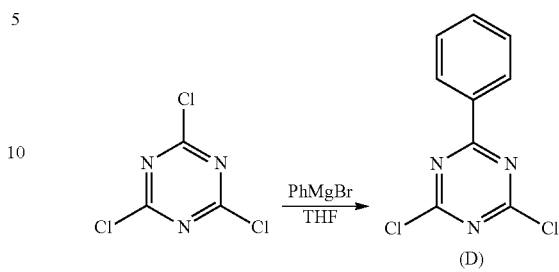

(D)

Under a nitrogen atmosphere, 85.4 g (0.46 mol) of cyanuric chloride and 500 ml of dehydrated tetrahydrofuran were mixed with stirring. To the resulting solution was added dropwise 600 ml of a tetrahydrofuran solution of phenylmagnesium bromide (1.1 mold) over 1 hour while maintaining the temperature of the reaction solution at −20° C. or below and then the stirring was continued for 1.5 hours. Then, 300 ml of toluene and 500 ml of 2N HCl were added while maintaining the temperature of the reaction solution at 5° C. or below. The reaction solution was separated into an organic layer and an aqueous layer and the organic layer was washed with distilled water (2×300 ml), further washed once with a saturated aqueous sodium chloride solution, and dehydrated over magnesium sulfate. The magnesium sulfate was separated by filtration and the solvent was distilled off under reduced pressure. To the viscous liquid thus obtained was added 1,000 g of n-hexane and the mixture was heated with stirring. Thereafter, the mixture was filtered while hot and an insoluble matter was removed. The filtrate was cooled and the precipitated needle crystal was collected by filtration and dried to give 73.3 g (0.32 mol, 75% yield) of Intermediate D.

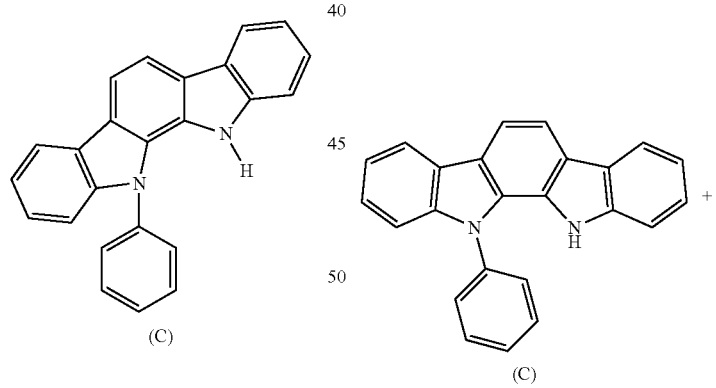

(C)

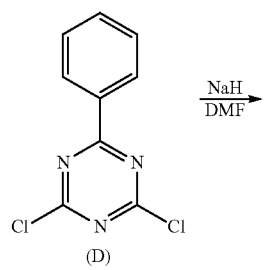

(D)

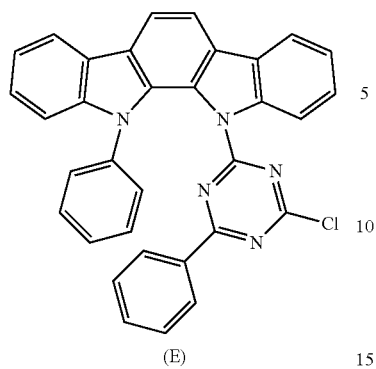

(E)

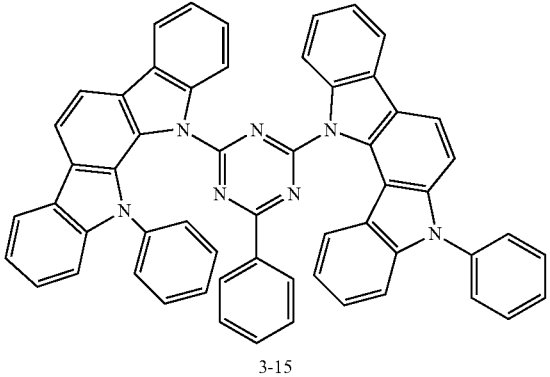

3-15

Under a nitrogen atmosphere, 1.6 g of sodium hydride (56% dispersion) and 50 ml of dehydrated N,N-dimethylformamide were stirred, a solution of 10.0 g (0.030 mol) of Intermediate C in 60 ml of dehydrated N,N-dimethylformamide was added dropwise over 30 minutes, and the stirring was continued for 1 hour. Then, a solution of 7.0 g (0.031 mol) of Intermediate D in 60 ml of dehydrated N,N-dimethylformamide was added dropwise over 30 minutes and, thereafter, the stirring was continued overnight. To the flask was added 300 g of distilled water and the precipitated yellow crystal was collected by filtration. The yellow crystal thus collected was purified by reslurrying and dried to give 15.0 g (0.029 mol, 96% yield) of Intermediate E.

APCI-TOFMS: m/z 523 [M+H]$^+$.

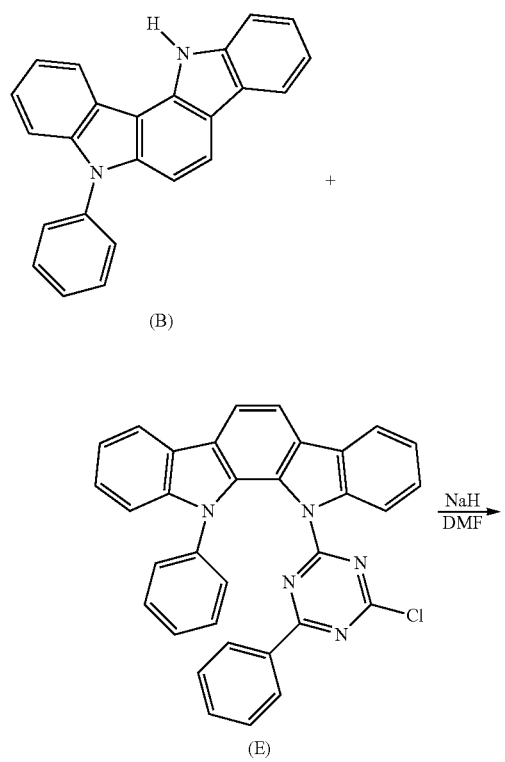

Under a nitrogen atmosphere, 2.4 g of sodium hydride (56% dispersion) and 130 ml of dehydrated N,N-dimethylformamide were stirred, a solution of 15.4 g (0.046 mol) of Intermediate B in 154 ml of dehydrated N,N-dimethylformamide was added dropwise over 30 minutes, and the stirring was continued for 1 hour. Then, a solution of 22.0 g (0.042 mol) of Intermediate E in 220 ml of dehydrated N,N-dimethylformamide was added dropwise over 30 minutes and, thereafter, the stirring was continued for 4 hours. To the flask was added 500 g of distilled water and the precipitated yellow crystal was collected by filtration. The yellow crystal thus collected was reslurried, dried, and then purified by a silica gel column to give 9.2 g (0.011 mol, 27% yield) of Compound 3-15.

Figure 2:
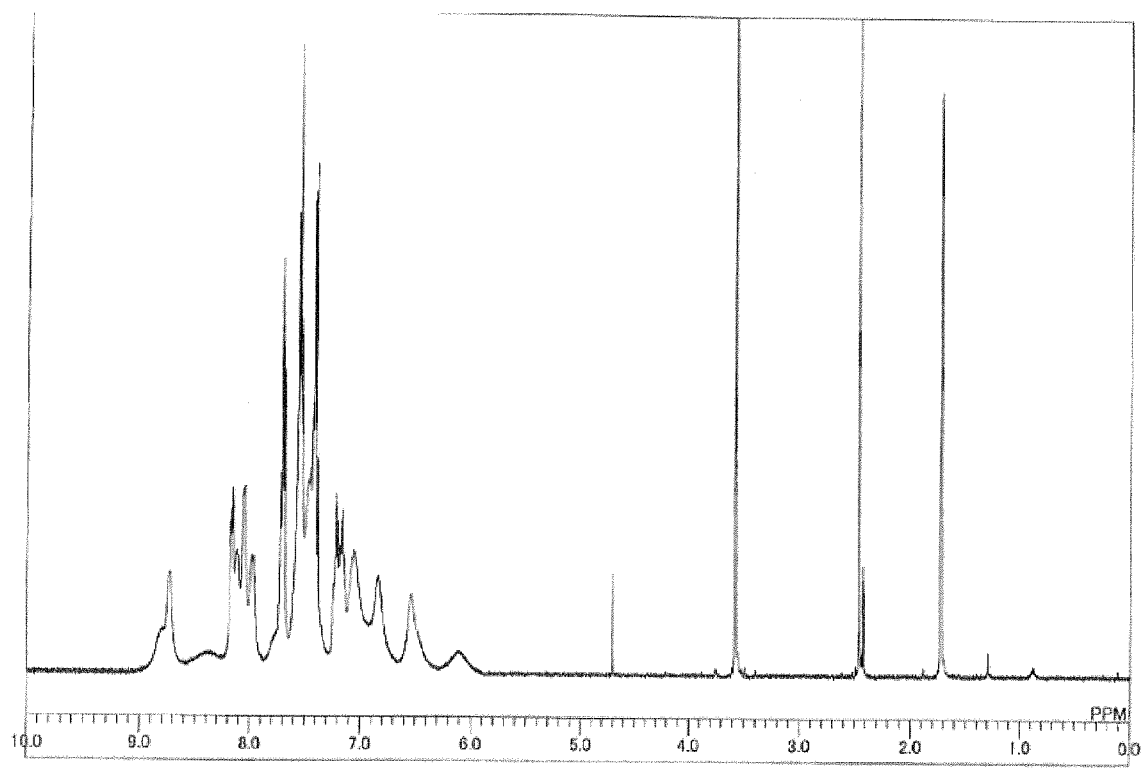
FIG. 2 shows a $^1$H-NMR chart of Compound 3-15.

APCI-TOFMS: m/z 818 [M+H]$^+$. The results of $^1$H-NMR measurement (solvent: THF-d8) are shown in FIG. 2.

In the same manner as described above, Compounds 1-31, 2-3, 3-22, 5-19, 6-11, 6-17, and 6-30 were synthesized.

Example 1

The constituent layers were deposited in thin film by the vacuum deposition process at a degree of vacuum of $4.0 \times 10^{-5}$ Pa one upon another on a glass substrate on which a 110 nm-thick ITO anode had been formed. First, copper phthalocyanine (CuPc) was deposited on the ITO anode to a thickness of 25 nm. Then, 4,4'-bis[N-(1-naphthyl)-N-phenylamino]biphenyl (NPB) was deposited to a thickness of 40 nm as a hole-transporting layer. Next, Compound 3-15 obtained in Synthetic Example 1 as a host material and tris(2-phenylpyridine)iridium(III) (Ir(ppy)$_3$) as a phosphorescend dopant were co-deposited from different deposition sources to a thickness of 40 nm as a light-emitting layer. The concentration of Ir(ppy)$_3$ in the light-emitting layer was 10.0 wt %. Next, tris(8-hydroxyquinolinolato)aluminum(III) (Alq3) was deposited to a thickness of 20 nm as an electron-transporting layer. Then, lithium fluoride (LiF) was deposited on the electron-transporting layer to a thickness of 1.0 nm as an electron-injecting layer. Finally, aluminum (Al) was deposited on the electron-injecting layer to a thickness of 70 nm as an electrode to complete the fabrication of an organic EL device.

The organic EL device thus fabricated was connected to an external power source and, when direct current voltage was applied, the device was confirmed to have the luminous characteristics shown in Table 1. In Table 1, the values of the luminance, voltage, and luminous efficiency are values obtained when the device was driven at 10 mA/cm$^2$. The luminance half-life was evaluated by driving the device by constant current at 40 mA/cm$^2$ and the results were converted to the case where the initial luminance was 1,000 cd/m$^2$. The peak wavelength of the spectrum of light emitted from the device is 520 nm and this proves that light is emitted from Ir(ppy)$_3$.

Example 2

An organic EL device was fabricated as in Example 1 except that Compound 1-31 was used as the host material in the light-emitting layer.

Example 3

An organic EL device was fabricated as in Example 1 except that Compound 2-3 was used as the host material in the light-emitting layer.

Example 4

An organic EL device was fabricated as in Example 1 except that Compound 3-22 was used as the host material in the light-emitting layer.

Example 5

An organic EL device was fabricated as in Example 1 except that Compound 5-19 was used as the host material in the light-emitting layer.

Example 6

An organic EL device was fabricated as in Example 1 except that Compound 6-11 was used as the host material in the light-emitting layer.

Example 7

An organic EL device was fabricated as in Example 1 except that Compound 6-17 was used as the host material in the light-emitting layer.

Example 8

An organic EL device was fabricated as in Example 1 except that Compound 6-30 was used as the host material in the light-emitting layer.

Comparative Example 1

An organic EL device was fabricated as in Example 1 except that Compound H-1 shown below was used as the host material in the light-emitting layer.

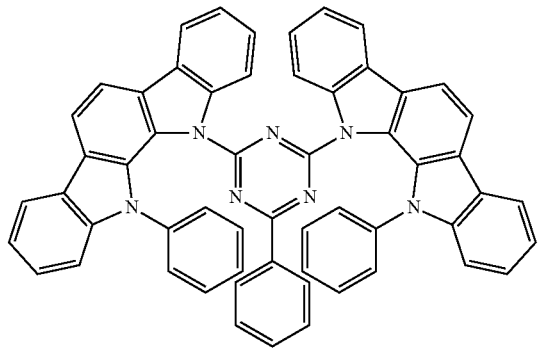 [SMILES: c1ccc(-c2nc(-n3c4ccccc4c4ccc5c6ccccc6n(-c6ccccc6)c5c43)nc(-n3c4ccccc4c4ccc5c6ccccc6n(-c6ccccc6)c5c43)n2)cc1]

The peak wavelength of the spectrum of emitted light is 520 nm for each of the organic EL devices fabricated in Examples 2 to 8 and Comparative Example 1 and this proves that light is emitted from Ir(ppy)$_3$. The luminous and life characteristics are shown in Table 1.

TABLE 1

|  | host material | initial characteristics (@10 mA/cm$^2$) | | | life characteristics (@1000 cd/m$^2$) |
| --- | --- | --- | --- | --- | --- |
|  |  | luminance (cd/m$^2$) | voltage (V) | luminous efficiency (lm/W) | luminance half-life (hours) |
| Example |  |  |  |  |  |
| 1 | 3-15 | 3250 | 6.25 | 16.3 | 7250 |
| 2 | 1-31 | 3020 | 7.00 | 13.6 | 8060 |
| 3 | 2-3 | 3310 | 7.06 | 14.7 | 7310 |
| 4 | 3-22 | 3380 | 6.90 | 15.4 | 8220 |
| 5 | 5-19 | 2950 | 6.90 | 13.4 | 8200 |
| 6 | 6-11 | 3320 | 6.85 | 15.2 | 7580 |
| 7 | 6-17 | 3110 | 6.15 | 15.9 | 8150 |
| 8 | 6-30 | 3410 | 7.00 | 15.3 | 7840 |
| Comparative Example 1 | H-1 | 2350 | 6.10 | 12.1 | 5300 |

Each of the organic EL devices fabricated in Examples 1 to 8 is improved in initial characteristics and life characteristics in comparison with the device of Comparative Example 1. This indicates that the use of a material containing different indolocarbazole skeletons in the molecule as the main component of the light-emitting layer improves the characteristics of an organic EL device.

INDUSTRIAL APPLICABILITY

The indolocarbazole compound to be used in the organic electroluminescent device of this invention has two or more different isomeric indolocarbazole skeletons in the molecule or has identical isomeric indolocarbazole skeletons linked together in such a mode as to form an unsymmetrical molecular structure. This makes it possible to adjust finely the transfer rates of holes and electrons and control the values of a variety of energies such as IP, EA, and T1. As a result, an organic EL device using the said indolocarbazole compound can realize an optimal balance of carriers in the light-emitting layer and improve the luminous characteristics sharply. Further, this indolocarbazole compound is capable of improving the stability in the activated state such as oxidation, reduction, and excitation and, at the same time, it exhibits good characteristics in the amorphous state. Thus, the indolocarbazole compound can realize an organic EL device of long driving life and high curability. Still further, the use of this compound makes it possible to design materials which are provided with a function such as improved solubility and offer materials better suited to a wet process.

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:

1. An organic electroluminescent device comprising an anode, organic layers comprising a phosphorescent light-emitting layer, and a cathode piled one upon another on a substrate wherein at least one organic layer selected from the group consisting of a phosphorescent light-emitting layer, a hole-transporting layer, an electron-transporting layer, and a hole-blocking layer contains an indolocarbazole compound represented by general formula (1);

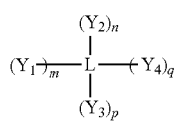
(1)

In general formula (1), L is an (m+n+p+q)-valent aromatic hydrocarbon group of 6 to 50 carbon atoms or an (m+n+p+q)-valent aromatic heterocyclic group of 3 to 50 carbon atoms; each of $Y_1$ to $Y_4$ is a monovalent group which has an indolocarbazole skeleton represented by any one of formulas (1a-1) to (1a-6) and at least one of them is different isomeric indolocarbazole skeletons from the others; m is an integer of 1 to 3, n is an integer of 1 to 3, p is an integer of 0 to 3, q is an integer of 0 to 3, and m+n+p+q is an integer of 2 to 6;

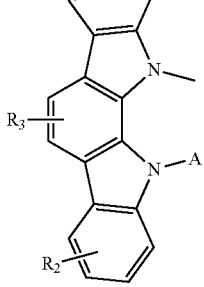
(1a-1)

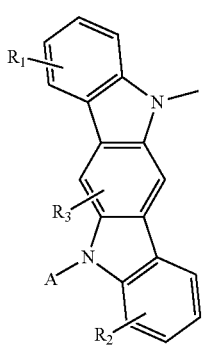
(1a-2)

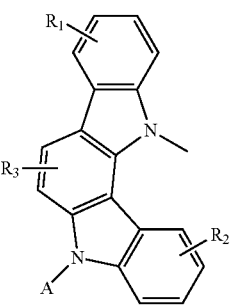
(1a-3)

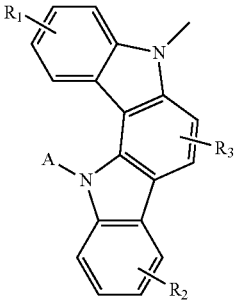
(1a-4)

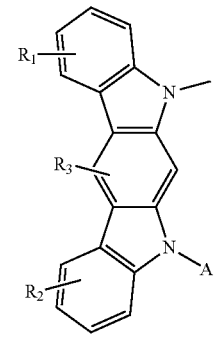
(1a-5)

(1a-6)

In formulas (1a-1) to (1a-6), each A is independently an alkyl group of 1 to 10 carbon atoms, a cycloalkyl group of 3 to 11 carbon atoms, an aromatic hydrocarbon group of 6 to 50 carbon atoms, or an aromatic heterocyclic group of 3 to 50 carbon atoms; each of $R_1$ to $R_3$ is independently a hydrogen atom, an alkyl group of 1 to 10 carbon atoms, a cycloalkyl group of 3 to 11 carbon atoms, an aromatic hydrocarbon group of 6 to 12 carbon atoms, or an aromatic heterocyclic group of 3 to 12 carbon atoms; however, in formulas (1a-2), (1a-4), and (1a-6), $R_3$ may form a fused ring together with the six-membered ring to which $R_3$ is linked.

2. An organic electroluminescent device as described in claim 1 wherein the indolocarbazole compound represented by general formula (1) is an indolocarbazole compound represented by any one of general formulas (2) to (7);

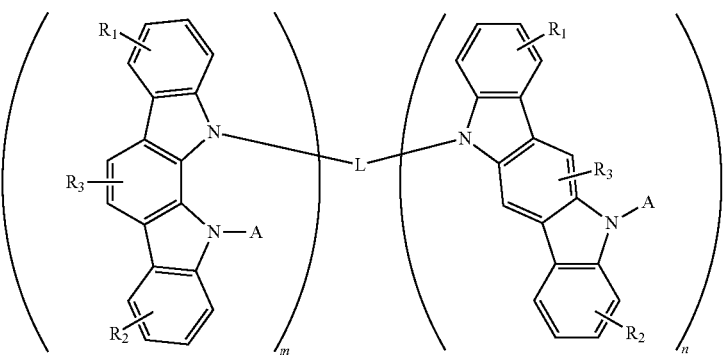
(2)
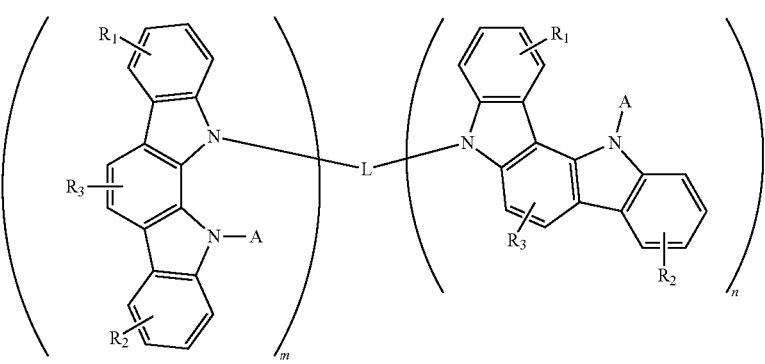
(3)
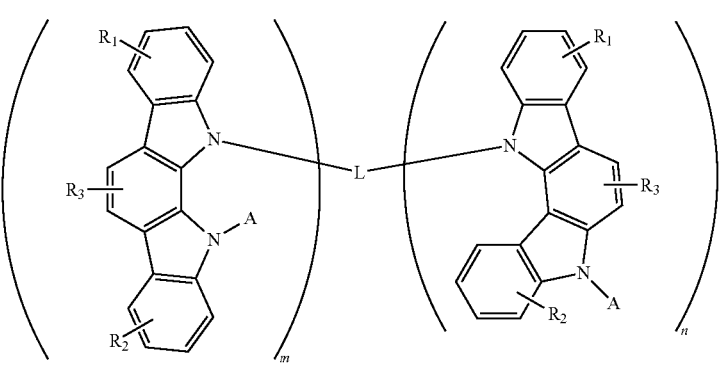
(4)
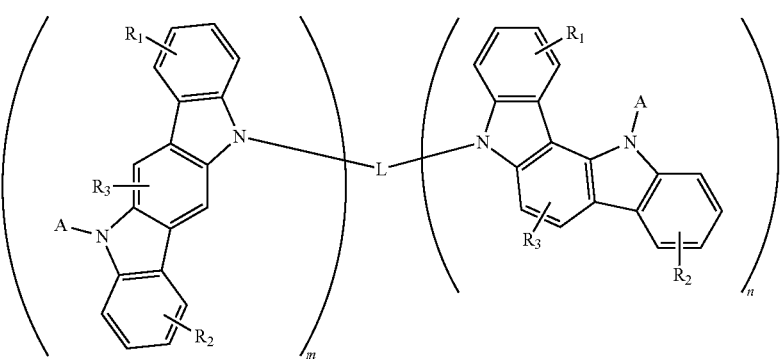
(5)

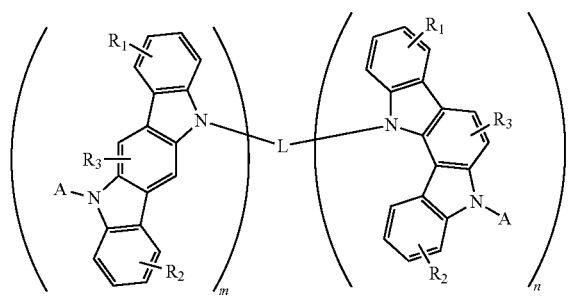 (6)

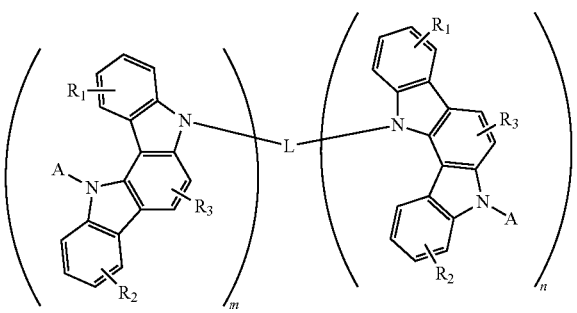 (7)

In general formulas (2) to (7), L, A, $R_1$ to $R_3$, m, and n have the same meaning as those in general formula (1) and formulas (1a-1) to (1a-6).

3. An organic electroluminescent device as described in claim 2 wherein, in the indolocarbazole compounds represented by general formulas (2) to (7), m and n are respectively 1 and each of R1 to R3 is independently a hydrogen atom, an alkyl group of 1 to 10 carbon atoms, a cycloalkyl group of 3 to 11 carbon atoms, an aromatic hydrocarbon group of 6 to 12 carbon atoms, or an aromatic heterocyclic group of 3 to 12 carbon atoms.

4. An organic electroluminescent device as described in claim 1 wherein the organic layer containing the indolocarbazole compound is the light-emitting layer containing a phosphorescent dopant.

5. An organic electroluminescent device as described in claim 2 wherein the organic layer containing the indolocarbazole compound is the light-emitting Layer containing a phosphorescent dopant.

6. An organic electroluminescent device as described in claim 3 wherein the organic layer containing the indolocarbazole compound is the light-emitting layer containing a phosphorescent dopant.

* * * * *